United States Patent [19]

Hawley-Nelson et al.

[11] Patent Number: 6,051,429
[45] Date of Patent: *Apr. 18, 2000

[54] PEPTIDE-ENHANCED CATIONIC LIPID TRANSFECTIONS

[75] Inventors: Pamela Hawley-Nelson, Silver Spring; Jianqing Lan, Germantown; PoJen Shih, Columbia; Joel A. Jessee, Mt. Airy; Kevin P. Schifferli, Germantown; Gulilat Gebeyehu, Silver Spring, all of Md.

[73] Assignee: Life Technologies, Inc., Rockville, Md.

[ * ] Notice: This patent is subject to a terminal disclaimer.

[21] Appl. No.: 08/818,200

[22] Filed: Mar. 14, 1997

Related U.S. Application Data

[63] Continuation-in-part of application No. 08/658,130, Jun. 4, 1996, Pat. No. 5,736,392, which is a continuation-in-part of application No. 08/477,354, Jun. 7, 1995, abandoned.

[51] Int. Cl.$^7$ .......................... C12N 15/64; C12N 15/63; C12N 7/00; C12N 15/11
[52] U.S. Cl. .................. 435/458; 435/235.1; 435/320.1; 536/23.1
[58] Field of Search ...................... 428/402.2; 435/172.3, 435/235.1, 320.1, 458; 536/23.1

[56] References Cited

U.S. PATENT DOCUMENTS

| | | | |
|---|---|---|---|
| 4,946,787 | 8/1990 | Eppstein et al. | 264/4.1 |
| 5,166,320 | 11/1992 | Wu et al. | 530/395 |
| 5,266,106 | 11/1993 | Winnik et al. | 106/31.58 |
| 5,338,532 | 8/1994 | Tomalia et al. | 424/1.49 |
| 5,354,844 | 10/1994 | Beug et al. | 530/345 |
| 5,527,524 | 6/1996 | Tomalia et al. | 424/1.33 |
| 5,560,929 | 10/1996 | Hedstrand et al. | 424/486 |
| 5,574,142 | 11/1996 | Meyer, Jr. et al. | 536/23.1 |
| 5,578,475 | 11/1996 | Jessee | 435/456 |
| 5,587,441 | 12/1996 | Frechet et al. | 526/238 |
| 5,587,446 | 12/1996 | Fretchet et al. | 526/3.33 |
| 5,589,392 | 12/1996 | Short | 435/320.1 |
| 5,658,776 | 8/1997 | Flotte et al. | 435/457 |
| 5,661,025 | 8/1997 | Szoka, Jr. et al. | 435/458 |
| 5,736,387 | 4/1998 | Paul et al. | 435/320.1 |
| 5,759,805 | 6/1998 | Feldhaus et al. | 435/69.1 |
| 5,795,587 | 8/1998 | Gao et al. | 424/450 |

FOREIGN PATENT DOCUMENTS

| | | |
|---|---|---|
| B-26526/92 | 9/1992 | Australia . |
| 0 359 347 | 3/1990 | European Pat. Off. . |
| 0 544 292 | 11/1992 | European Pat. Off. . |
| WOA91/16024 | 10/1991 | WIPO . |
| WO92/13570 | 8/1992 | WIPO . |
| WO93/07282 | 4/1993 | WIPO . |
| WO93/07283 | 4/1993 | WIPO . |
| WO93/19768 | 10/1993 | WIPO . |
| WO94/04696 | 3/1994 | WIPO . |
| WO94/23751 | 10/1994 | WIPO . |
| WO9423751 | 10/1994 | WIPO . |
| WO95/02397 | 1/1995 | WIPO . |
| WO95/24221 | 9/1995 | WIPO . |
| WO95/31557 | 11/1995 | WIPO . |
| WO96/01841 | 1/1996 | WIPO . |
| WO 96/05218 | 2/1996 | WIPO . |
| WO96/05218 | 2/1996 | WIPO . |
| WO96/10038 | 4/1996 | WIPO . |
| WO96/22765 | 8/1996 | WIPO . |

OTHER PUBLICATIONS

Curiel, D.T. et al. (1991), "Adenovirus enhancement of transferrin–polylysine–mediated gene delivery," Proc. Natl. Acad. Sci. USA 88:8850–8854.

Liljistrom, P. and Garoff, H. (1991), "A New Generation of Animal Cell Expression Vectors Based on the Semliki Forest Virus Replicon," Biotech. 9:1356–1361.

Phalen et al. (1991), "Cholesterol is Required for Infection by Semliki Forest Virus," J. Cell Biol. 112(4):615–623.

Murata et al. (1991), "Modification of the N–Terminus of Membrane Fusion–Active Peptides Blocks the Fusion Activity," Biochem. Biophys. Res. Commun. 179(2):1050–1055.

Cotton et al. (1992), "High–efficiency receptor–mediated delivery of small and large 48 kilobase gene constructs using the endosome–disruption activity of defective or chemically inactivated adenovirus particles," Proc. Natl. Acad. Sci. USA 89:6094–6098.

Curiel, D.T. et al. (1992), "High–Efficiency Gene Transfer Mediated by Adenovirus Coupled to DNA–Polylysine Complexes," Hum. Gene Therapy 3:147–154.

Wagner, E. et al. (1992), "Coupling of adenovirus to transferrin–polylysine/DNA complexes greatly enhances receptor–mediated gene delivery and expression of transfected genes," Proc. Natl. Acad. Sci. USA 89:6099–6103.

Wagner, E. et al. (1992), "Influenza virus hemagglutinin HA–2 N–terminal fusogenic peptides augment gene transfer by transferrin–polylysine–DNA complexes: Toward a synthetic virus–like gene–transfer vehicle, " Proc. Natl. Acad. Sci. USA 89:7934–7938.

Epand et al. (1992), "Peptide models for the membrane destabilizing actions of viral fusion proteins," Biopolymers 32:309.

(List continued on next page.)

*Primary Examiner*—John S. Brusca
*Attorney, Agent, or Firm*—Greenlee, Winner and Sullivan, P.C.

[57] ABSTRACT

The present invention provides compositions useful for transfecting eukaryotic cells comprising nucleic acid complexes with peptides, wherein the peptide is optionally covalently coupled to a nucleic acid-binding group, and cationic lipids or dendrimers as transfection agents. The invention also provides transfection compositions in which a peptide is covalently linked to the transfection agent (lipid, cationic lipid or dendrimer). Inclusion of peptides or modified-peptides in transfection compositions or covalent attachment of peptides to transfection agents results in enhanced transfection efficiency. Methods for the preparation of transfection compositions and methods of using these transfection compositions as intracellular delivery agents and extracellular targeting agents are also disclosed.

95 Claims, 12 Drawing Sheets

OTHER PUBLICATIONS

Walker et al. (1992), "Cationic lipids direct a viral glycoprotein into the class I major histocompatibility complex antigen–presentation pathway," Proc. Natl. Acad. Sci. USA 89:7915–7918.

Ciccarone et al. (1993), "Cationic Liposome–Mediated Transfection of Eukaryotic Cells: High Efficiency Nucleic Acid Delivery with Lipofectin, Lipofectace™, and Lipofectamine™ Reagents," FASEB J., Abstracts, 7(7):A1131, Abstract No. 454.

Yoshimura et al. 91993), "Adenovirus–mediated Augmentation of Cell Trnasfection with Unmodified Plasmid Vectors," J. Biol. Chem. 268:2300.

"Transfection Reagent," Genet. Eng. News (Jun. 15, 1993), p. 12, col. 4.

Kamata, H. et al. (1994), "Amphiphilic peptides enhance the efficiency of liposome–mediated DNA transfection," Nucl. Acids Res. 22(3):536–537.

Remy et al. (1995), "Targeted gene transfer into hepatoma cells with lipopolyamine–condensed DNA particles presenting galactose ligands: A stage toward artificial viruses," Proc. Natl. Acad. Sci. USA 92:1744–1748.

Grant, D.S. et al. (1989), "Two Different Laminin Domains Mediate the Differentiation of Human Endothelial Cells into Capillary–like Structures In Vitro," Cell 58:933–943.

Gardner, J.M. and Hynes, R.O. (1985), "Interaction of Fibronectin with Its Receptor on Platelets," Cell 42:439–448.

Wickham, T.J. et al. (1995), "Targeting of adenovirus penton base to new receptors through replacement of its RGD motif with other receptor–specific peptide motifs," Gene Therapy 2:750–756.

Pierschbacher, M.D. and Ruoslahti, E. (1987), "Influence of Stereochemistry of the Sequence Arg–Gly–Asp–Xaa on Binding Specificity in Cell Adhesion," J. Biol. Chem. 262(36):17294–17298.

Mason, P.W. et al. (1994), "RGD sequence of foot-and-mouth disease virus is essential for infecting cells via the natural receptor but can be bypassed by an antibody–dependent enhancement pathway," Proc. Natl. Acad. Sci. USA 91:1932–1936.

Ruoslahti, E. and Pierschbacher, M.D. (1987), "New Perspectives in Cell Adhesion: RGD and Integrins," Science 238:491–497.

Pierschbacher, M.D. and Ruoslahti, E. (1984), "Cell attachment activity of fibronectin can be duplicated by small synthetic fragments of the molecule," Nature 309:30–33.

Dedhar, S. et al. (1987), "A Cell Surface Receptor Complex for Collagen Type I Recognizes the Arg–Gly–Asp Sequence," J. Cell Biol. 104:585–593.

Friedlander, D.R. et al. (1988), "Functional Mapping of Cytotactin: Proteolytic Fragments Active in Cell–Substrate Adhesion," J. Cell Biol. 107:2329–2340.

Humphries, M.J. et al. (1986), "Identification of an Alternatively Spliced Site in Human Plasma Fibronectin That Mediates Cell Type–specific Adhesion," J. Cell Biol. 103:2637–2647.

Suzuki, S. et al. (1985), "Complete amino acid sequence of human vitronectin deduced from cDNA. Similarity of cell attachment sites in vitronectin and fibronectin," EMBO J. 4(10):2519–2524.

Wayner, E.A. et al. (1989), "Identification and Characterization of the T Lymphocyte Adhesion Receptor for an Alternative Cell Attachment Domain (CS–1) in Plasma Fibronectin," J. Cell Biol. 109:1321–1330.

Lawler, J. et al. (1988), "Cell Attachment to Thrombospondin: The Role of Arg–Gly–Asp, Calcium, and Integrin Receptors," J. Cell Biol. 107:2351–2361.

Haverstick, D.M. et al. (1986), "Inhibition of Platelet Adhesion to Fibronectin, Fibrinogen, and von Willebrand Factor Substrates by a Synthetic Tetrapeptide Derived From the Cell–Binding Domain of Fibronectin," Blood 86(4):946–952.

Humphries, M.J. et al. (1987), "Identification of Two Distinct Regions of the Type III Connecting Segment of Human Plasma Fibronectin That Promote Cell Type–specific Adhesion," J. Biol. Chem. 262(14):6886–6892.

Zhou, X. and Huang, L. (1994), "DNA transfection mediated by cationic liposomes containing lipopolylysine: characterization and mechanism of action," Biochim. Biophys. Acta 1189:195–203.

Stegmann, T. et al. (1989), "Protein–mediated membrane fusion," Ann. Rev. Biophys. Biophys. Chem. 18:187–211.

Aumailley, M. et al. (1989), "Cell Attachment Properties of Collagen Type VI and Arg–Gly–Asp Dependent Binding to its $\alpha 2(VI)$ and $\alpha 3(VI)$ Chains," Exp. Cell Res. 181:463–474.

Kamata et al. (1994), "Amphiphilic peptides enhance the efficiency of liposome–mediated DNA transfection," Nucl. Acids Res. 22:536–537.

Life Technologies Catalog, (1993) pp. 9–19.

Hagstrom, J.E. et al. (1996), "Complexes of non–cationic liposomes and histone H1 mediate efficient transfection of DNA without encapsulation," Biochim. Biophys. Acta 1284:47–55.

Dingwall, C. and Laskey, R.A. (1991), "Nuclear targeting sequences—a consensus?" TIBS 16:478–481.

Bielinska, A. et al. (1996), "Regulation of in vivo gene expression using antisense oligonucleotides or antisense expression plasmids transfected using starburst PAMAM dendrimers," Nucl. Acids Res. 24(11):2176–2182.

Kukowska–Latallo, J.F. et al. (1996), "Efficient transfer to genetic material into mammalian cells using Starburst polyamidoamine dendrimers," Proc. Natl. Acad. Sci. USA 93:4897–4902.

Rihs, H.–P. et al. (1991), "The rate of nuclear cytoplasmic protein transport is determined by the casein kinase II site flanking the nuclear localization sequence of the SV40 T–antigen," EMBO J. 10(3):633–639.

DeRoberts et al. (1978),"Intracellular migration of nuclear proteins in *Xenopus oocytes,*" Nature 272:254–256.

Väänänen et al., (1980), "Fusion and Haemolysis of Erthrocytes Caused by Three Togaviruses: Semiki Forest, Sindbis, and Rubella," J. Gen. Virology 46:467–475.

Carrasco, L. et al. (1982),"Modification of Membrane Permeability in Vaccinia Virus–Infected Cells," J. Virol. 117:62–69.

Eytan, G.D. (1982), "Use of Liposomes for Reconstitution of Biological Functions," Biochem. Biophys. Acta 694:185–202.

Young et al. (1983), "Interaction of Enveloped Viruses with Planar Bilayer Membranes: Observations on Sendai, Influenza, Vesicular Stomatitis, and Simiki Forest Viruses," Virology 128:186–194.

Marsh et al. (1983), "Interactions of Simiki Forest Virus Spike Glycoprotein Rosettes and Vesicles with Cultured Cells," J. Cell Biol. 96:455–461.

Schlegel, R. et al. (1983), "Inhibition of VSV Binding and Infectivity by Phosphatidylserine: Is Phosphatidylserine a VSV–Binding Site?" Cell 32:639–646.

Ciccarone et al. DMRIE–C reagent for transfection of suspension cells and for RNA transfections. Focus vol. 17 pp. 84–87, 1995.

Promega Catalog p. 251, 1993.

Braunlin et al. Equilibrium dialysis studies of polyamine binding to DNA. Biopolymers vol. 21 pp. 1301–1314, 1982.

Gao, X. and Huang, L. (1996), "Potentiation of Cationic Liposome–Mediated Gene Delivery of Polycations," Biochemistry 35:1027–1036.

Kalderon et al. (1984), "A Short Amino Acid Sequence Able to Specify Nuclear Location," Cell 39:499–509.

Kraaijeveld, S.A. et al. (1984), "The Effect of liposomal charge on the neutralizing antibody response against inactivated encephaloymocarditis and Simiki Forest Viruses," Clin. Exp. Immunol. 56:509–514.

Schlegel, R and Wade, M. (1985), "Biologically Active Peptides of the Vesicular Stomatitus Virus Glycoprotein," J. Virol. 53(1):319–323.

Klappe, K. et al. (1986), "Parameters Affecting Fusion Between Sendai Virus and Liposomes. Role of Viral Proteins, Liposome Composition, and pH," Biochemistry 25:8252–8260.

Sands, J.A. (1986), "Virucidal Activity of Cetyltrimethylammonium Bromide Below the Critical Micelle Concentration," FEMS Microbiol. Lett. 36:261–263.

Scheule (1986), "Novel Preparation of Functional Sindbis Virosomes," Biochemistry 25:4223–4232.

Lanford et al. (1986), "Induction of Nuclear Transport with a Synthetic Peptide Homologous to the SV40 T Antigen Transport Signal," Cell 46:575–582.

Kaneda et al. (1987), "The Improved Efficient Method for Introducing Macromolecules into Cells Using HVJ (Sendai virus) Liposomes with Gangliosides," Exp. Cell Res. 173:56–69.

Otero, M.J. and Carrasco, L. (1987), "Proteins are Cointernalized with Virion Particles during Early Infection," J. Virol. 160:75–80.

Tikchonenko, T. et al. (1988), "Transfer to condensed viral DNA into eukaryotic cells using proteoliposomes," Gene 63:321–330.

Gould–Fogerite, S. et al. (1989), "Chimerasome–mediated gene transfer in vitro and in vivo," Gene 84:429–438.

Kaneda et al. (1989), "Introduction and Expression of the Human Insulin Gene in Adult Rat Liver," J. Biol. Chem. 264(21):1216–1219.

Neugebauer, J. (1990), "Detergents: An Overview," Meth. Enzymol. 182:239–253.

Lapidot et al. (1990), "Fusion–Mediated Microinjection of Liposome–Enclosed DNA into Cultured Cells with the Aid of Influenza Virus Glycoproteins," Exp. Cell Res. 189:241–246.

Konopka, K. et al. (1991), "Enhancement of human immunodeficiency virus type 1 infection by cationic liposomes: the role of CD4, serum and liposome–cell interactions," J. Gen. Virol. 72:2685–2696.

PEPTIDE-ENHANCED CATIONIC LIPID TRANSFECTIONS

CROSS-REFERENCE TO RELATED APPLICATIONS

This application is a continuation-in-part of U.S. application Ser. No. 08/658,130, filed Jun. 4, 1996, U.S. Pat. No. 5,736,392 which in turn is a continuation-in-part of U.S. application Ser. No. 08/477,354, filed Jun. 7, 1995 (now abandoned), both of which are incorporated by reference in their entirety herein.

FIELD OF THE INVENTION

Compositions containing peptides, optionally conjugated to nucleic acid-binding groups, to lipids or to dendrimers, and transfection agents, including cationic lipids and dendrimer polymers, useful for transfecting eukaryotic cells are disclosed. Also disclosed are methods of transfecting eukaryotic cells employing such compositions.

BACKGROUND OF THE INVENTION

Lipid aggregates such as liposomes can function to facilitate introduction of macromolecules, such as DNA, RNA, and proteins, into living cells. Lipid aggregates comprising cationic lipid components can be effective for delivery and introduction of large anionic molecules, such as nucleic acids, into certain types of cells. See Felgner, P. L. and Ringold, G. M. (1989) Nature 337:387–388 and Felgner, P. L. et al. (1987) Proc. Natl. Acad. Sci. USA 84:7413. Since the membranes of most cells have a net negative charge, anionic molecules, particularly those of high molecular weight, are not readily taken up by cells. Cationic lipids aggregate to and bind polyanions, such as nucleic acids, tending to neutralize the negative charge. The effectiveness of cationic lipids in transfection of nucleic acids into cells is thought to result from an enhanced affinity of cationic lipid-nucleic acid aggregates for cells, as well as the function of the lipophilic components in membrane fusion.

Dendrimers are a new type of synthetic polymers with regular, dendric branching with radial symmetry composed of an initiator core, interior layers (or generations) of repeating units, radially attached to the core and an exterior surface of terminal functional groups. See: D. A. Tomalia and H. D. Durst (1993) in E. Weber (ed.) Topics in Current Chemistry, Vol. 165: Supramolecular Chemistry I-Directed Synthesis and Molecular Recognition, Springer-Verlag, Berlin, pp.193–313. The size, shape and surface charge density of the dendrimer is controlled by choice of core, repeating unit, number of generations and terminal functional group. See: U.S. Pat. Nos. 5,527,524; 5,338,532; 4,694,064; 4,568,737; 4,507,466; and PCT patent applications; WO8801179; WO8801178; WO9524221; and WO9502397. "STARBURST" (Trademark, Dendritech, Inc.) or dense star polyamidoamine dendrimers have been reported to mediate efficient transfection of DNA into mammalian cells (J. F. Kukowska-Latolla et al. (1996) Proc. Natl. Acad. Sci. USA 93:4897–4902 and A. Bielinska et al. (1996) Nucleic Acids Res. 24(11):2176–2182). PCT patent application WO9524221 relates to bioactive or targeted dendrimer conjugates; PCT patent applications WO9319768 and WO9502397 relate to polynucleotide delivery systems comprising dendrimers.

Transfection agents, including cationic lipids and dendrimers, are not universally effective for transfection of all cell types. Effectiveness of transfection of different cells depends on the particular transfection agent composition and the type of lipid aggregate or dendrimer-complex formed. In general, polycationic lipids are more efficient than monocationic lipids in transfecting eukaryotic cells. Behr, J-P. et al. (1989) Proc. Natl. Acad. Sci. 86:6982–6986, Hawley-Nelson, P., et al. (1993) FOCUS 15:73 and U.S. Pat. No. 5,334,761 (Gebeyehu et al.). Behr et al. and EPO published application 304 111 (1990), for example, describe improved transfection using carboxyspermine-containing cationic lipids including 5-carboxyspermylglycine dioctadecyl-amide (DOGS) and dipalmitoylphosphatidylethanolamine 5-carboxyspermylamide (DPPES). Despite their relative effectiveness, however, successful transfection of eukaryotic cell cultures using polycationic lipid reagents often requires high dosages of nucleic acid (approximately $10^5$ DNA molecules per cell). For transfection, the optimal charge ratio of DNA/dendrimer was found to be between 1:5 and 1:50 and G5 (generation 5)-G10 dendrimers were reported capable of mediating transfection. Transfection efficiency of a given dendrimer varied with cell type, as has been observed with cationic lipid-mediated transfection (J. F. Kukowska-Latolla et al. (1996) Proc. Natl. Acad. Sci. USA 93:4897–4902).

Many biological materials are taken up by cells via receptor-mediated endocytosis. See: Pastan and Willingham (1981) Science 214:504–509. This mechanism involves binding of a ligand to a cell-surface receptor, clustering of ligand-bound receptors, and formation of coated pits followed by internalization of the ligands into endosomes. Both enveloped viruses, like influenza virus and alphaviruses, and non-enveloped viruses, like Adenovirus, infect cells via endocytotic mechanisms. See: Pastan, I. et al. (1986) in Virus Attachment and Entry into Cells, (Crowell, R. L. and Lonberg-Holm, K., eds.) Am. Soc. Microbiology, Washington, p. 141–146; Kielian, M. and Helenius, A. (1986) "Entry of Alphaviruses" in The Togaviridae and Flaviviridae, (Schlesinger, S. and Schlesinger, M. J., eds.) Plenum Press, New York p.91–119; FitzGerald, D. J. P. et al. (1983) Cell 32:607–617. Enhancement of dendrimer-mediated transfection of some cells by chloroquine (a lysosomotropic agent) suggests that endocytosis is involved in at least some dendrimer-mediated transfections.

The introduction of foreign DNA sequences into eukaryotic cells mediated by viral infection is generally orders of magnitude more efficient than transfection with cationic lipid or dendrimer transfection agents. Viral infection of all the cells in a culture requires fewer than 10 virus particles per cell. Although the detailed mechanism of fusion is not fully understood and varies among viruses, viral fusion typically involves specific fusagenic agents, such as viral proteins, viral spike glycoproteins and peptides of viral spike glycoproteins. Vesicular stomatitis virus (VSV) fusion, for example, is thought to involve interaction between the VSV glycoprotein (G protein) and membrane lipids (Schlegel, R. et al. (1983) Cell 32:639–646). The VSV G protein reportedly binds preferentially to saturable receptors such as acidic phospholipid phosphatidylserine (Schlegel, R. and M. Wade (1985) J. Virol. 53(1):319–323). Fusion of influenza virus involves hemagglutinin HA-2 N-terminal fusagenic peptides. See Kamata, H. et al. (1994) Nucl. Acids Res. 22(3):536–537.

Cell binding can also be enhanced, accelerated or made selective with peptides that bind cell receptors. For example, the penton-base protein of the Adenovirus coat contains the peptide motif RGD (Arg-Gly-Asp) which mediates binding to integrins and viral internalization via receptor-mediated endocytosis (Wickham, T. J. et al. (1995) Gene Therapy 2:750–756).

The efficiency of cationic lipid transfections has recently been shown to be enhanced by the addition of whole virus particles to the transfection mixture. See Yoshimura et al. (1993) J. Biol. Chem. 268:2300. Certain viral components may also enhance the efficiency of cationic lipid-mediated transfection. See: U.S. patent applications Ser. Nos. 08/090,290, filed Jul. 12, 1993, now abandoned; and 08/274,397, filed Jul. 12, 1994, now U.S. Pat. No. 5,578,475; incorporated by reference in their entirety herein. The use of peptides from viral proteins to enhance lipid-mediated transfections was also recently suggested by Kamata et al. (1994) Nucl. Acids Res. 22:536. Kamata et al. suggest that "LIPOFECTIN"-mediated transfections may be enhanced 3–4-fold by adding influenza virus hemagglutinin peptides to the transfection mixture. Despite these positive early indications, results vary as to the effectiveness of including fusagenic or nuclear localization peptides in lipidic transfection compositions. Remy et al. (1995) Proc. Natl. Acad. Sci. USA 92:1744 report that "[a]ddition of lipids bearing a fusagenic or a nuclear localization peptide head group to the (polycationic lipid-DNA complex) particles does not significantly improve an already efficient system."

SUMMARY OF THE INVENTION

The present invention is based on the discovery that peptide sequences from viral proteins and other sources can significantly enhance the efficiency of transfection of eukaryotic cells mediated by cationic lipids or by dendrimers. The compositions and methods of the invention comprise peptides, modified-peptides and peptide conjugates, including those of fusagenic, membrane-permeabilizing, receptor-ligand, and/or nuclear-localization peptides or peptides that localize to other sub-cellular locations (e.g., mitochondrial localization peptides), which significantly improve the efficiency of transfection when bound to nucleic acid prior to adding the transfection reagent. These fusagenic, receptor-ligand, nuclear localization or other peptides can form a noncovalent association or complex with the nucleic acid that is to be introduced into a cell. Complex formation can be enhanced by covalently coupling of the peptide to a DNA-binding group, which can bind to the nucleic acid through conformational or charge interactions and facilitate binding of the peptide to DNA. More generally, nucleic acid-peptide complex formation can be enhanced by covalent coupling of the peptide to a nucleic acid-binding group. Nucleic acids (DNA and RNA and variants thereof) are more efficiently transported into the cell by the transfection agent when bound to peptides of this invention and can with appropriate choice of peptide be directed to the cell nucleus or to other sub-cellular locations, thus requiring less nucleic acid starting material.

This invention also relates to the covalent coupling of peptides to the transfection agent, e.g., directly or via an appropriate linking or spacer group to a lipid of the cationic lipid transfection composition (a cationic or neutral lipid) or directly or via an appropriate linking or spacer group to a dendrimer. Of particular interest are conjugated lipids and dendrimers that are covalently linked to fusagenic peptides, membrane-permeabilizing peptides and receptor-ligand peptides.

The cationic lipid compositions of the present invention and the dendrimer compositions of this invention provide significant advantages over prior art compositions, including enhanced transformation frequency.

The present invention provides compositions and methods for transfecting eukaryotic cells, particularly higher eukaryotic cells, with nucleic acids. Nucleic acids, both DNA and RNA, are introduced into cells such that they retain their biological function. Compositions for transfecting eukaryotic cells comprising a peptide-nucleic acid complex and a transfection agent are provided. Transfection compositions of this invention include those in which the transfection agent is a cationic lipid, a mixture of cationic lipids and a mixture of cationic lipids and neutral lipids. Transfection compositions of this invention also include those in which the transfection agent is a dendrimer or mixture of dendrimers as well as mixtures of dendrimers and neutral or cationic lipids. Transfecting compositions comprise a peptide or modified-peptide, e.g. a peptide-conjugate, which binds nucleic acid and which is fusagenic, membrane-permeabilizing, functions for nuclear localization, or localization to another sub-cellular local, and/or as a receptor-ligand. Receptor-ligand peptides include those that bind to cell surface receptors, membrane receptors or cytosolic receptors and that can function for cell targeting or cell adhesion, and include those that trigger internalization or endocytosis. The peptide-nucleic acid complex is formed by interacting a peptide or modified-peptide with nucleic acid. Modified peptides include peptides covalently conjugated to nucleic acid-binding groups. Peptide-conjugates of this invention also include peptide-lipid and peptide dendrimer conjugates in which the peptide is covalently linked to the transfection agent or a component of the transfection agent.

For cationic lipid transfection, the peptide-nucleic acid complex is subsequently combined with cationic lipid (or a mixture of a cationic lipid and neutral lipid) to form a peptide-nucleic acid-lipid aggregate which facilitates introduction of the anionic nucleic acid through cell membranes, including the nuclear membrane, or targets the nucleic acid to a particular cell or sub-cellular location. Transfection compositions of this invention comprising peptide-nucleic acid complexes and cationic lipid can further include other non-peptide agents that are known to further enhance transfection.

For cationic lipid transfection employing a peptide-lipid conjugate, the peptide-lipid conjugate is combined with nucleic acid, as is conventional for cationic lipid transfection. The peptide-lipid conjugate may be first combined in a mixture of non-conjugated cationic and/or neutral lipids and then combined with nucleic acid to form a peptide-lipid-nucleic acid lipid aggregate which facilitates introduction of the anionic nucleic acid through cell membranes, including the nuclear membrane or targets the nucleic acid to a particular cell or to a sub-cellular location. Transfection compositions of this invention comprising peptide-lipid conjugates and nucleic acids can further include other non-peptide agents that are known to further enhance transfection.

In an alternative transfection method of this invention employing fusagenic peptides conjugated to lipids, the peptide-lipid conjugate is complexed with non-conjugated cationic lipids. A sub-cellular localization peptide, preferably a nuclear localization peptide, is complexed to the nucleic acid and the nucleic acid-peptide complex is admixed with the cationic lipid complex comprising covalently conjugated fusagenic peptides. The resulting mixture exhibits enhanced transfection efficiency.

For dendrimer transfection, the peptide-dendrimer conjugate is subsequently combined with nucleic acid, as is known in the art for dendrimer-mediated transfection, to form a peptide-dendrimer-nucleic acid aggregate that facilitates introduction of the anionic nucleic acid through cell membranes, including the nuclear membrane or targets the nucleic acid to a particular cell or sub-cellular location. When a peptide-dendrimer conjugate is employed, the peptide is believed, for the most part, to be concentrated at the outer surface of the dendrimer aggregate formed. Transfection compositions of this invention comprising peptide-dendrimer conjugates and nucleic acid can further include other non-peptide agents that are known to further enhance dendrimer transfection, for example dendrimer transfection can be enhanced by addition of DEAE-dextran.

In an alternative transfection method of this invention employing fusagenic peptides conjugated to dendrimers, the peptide-dendrimer conjugate is admixed with a nucleic acid that is itself complexed to a sub-cellular localization peptide, preferably a nuclear localization peptide. The new complex (e.g., Sp-NLS-nucleic acid complexed to VSVG or RGD or E5-dendrimer) is optionally admixed with non-conjugated dendrimers or optionally admixed with a cationic lipid composition. The resulting mixture exhibits enhanced transfection efficiency.

Peptides useful in transfection compositions include functional portions of proteins and or polypeptides that are fusagenic, function for nuclear or other sub-cellular localization, are receptor ligands, comprise cell-adhesive signals, cell-targeting signals, cell-internalization signals or endocytosis signals as well as peptides or functional portions thereof of viral fusagenic proteins, of viral nuclear localization signals, of receptor-ligands, of cell adhesion signals, of cell-targeting signals or of internalization- or endocytosis-triggering signals. Peptides useful in this invention include naturally-occurring peptides, and synthetic analogs or functional equivalents of naturally-occurring peptides. Peptides of this invention include those comprised of the twenty commonly-occurring amino acids as well as rare amino acids, such as homocysteine and ornithine. Transfection compositions comprising viral peptides or functional portions of viral peptides of influenza virus, vesicular stomatitis virus and simian virus 40 are of particular interest. Transfecting compositions containing viral peptides (as well as proteins and polypeptides) modified so that they are covalently conjugated to DNA-binding groups, for example, spermine or related polyamines, are also useful in the methods of this invention.

Inclusion of a peptide- or modified peptide-nucleic acid complex in a cationic lipid transfection composition can significantly enhance transfection (2-fold or more) of the nucleic acid compared to transfection of the nucleic acid mediated by the cationic lipid alone. Enhancement of transfection by peptides or modified peptides is pronounced in a wide variety of cell lines, including human primary cell lines and in cell lines that are generally considered by those in the art to be "hard-to-transfect.'

Monovalent or preferably polyvalent cationic lipids are employed in cationic lipid transfecting compositions. Preferred polyvalent cationic lipids are lipospermines, specifically DOSPA (2,3-dioleyloxy-N-[2(sperminecarboxamido)ethyl]-N,N-dimethyl-1-propanaminiumtrifluoro-acetate). Cationic lipids are optionally combined with non-cationic lipids, particularly neutral lipids, for example lipids such as DOPE (dioleoylphosphatidyl-ethanolamine). A cationic lipid composition composed of a 3:1 (w/w) mixture of DOSPA and DOPE is generally useful in transfecting compositions of this invention. Preferred transfection compositions are those which induce substantial transfection of a higher eukaryotic cell line.

Inclusion of a peptide- or modified peptide-nucleic acid complex in a dendrimer transfection composition can significantly enhance transfection (2-fold or more) of the nucleic acid compared to transfection of the nucleic acid mediated by the dendrimer alone or in combination with DEAE-dextran. Enhancement of transfection by peptides or modified peptides is pronounced in a wide variety of cell lines, including human primary cell lines and in cell lines that are generally considered by those in the art to be "hard-to-transfect."

In general, any dendrimer that can be employed to introduce nucleic acid into any cell, particularly into a eukaryotic cell, is useful in the improved transfection compositions and methods of this invention. Dendrimers of generation 5 or higher (G5 or higher) are preferred, with those of generation between G5–G10 being of particular interest. Dendrimers of this invention include those with $NH_3$ or ethylenediamine cores, $GX(NH_3)$ or $GX(EDA)$, where X=the generation number. Dendrimers where X=5–10 being preferred. Dendrimers of this invention include those in which the repeating unit of the internal layers is a amidoamine (to form polyamidoamines, i.e. PAMAMs). Dendrimers of this invention include those in which the terminal functional groups at the outer surface of the dendrimer provides a positive charge density, e.g., as with terminal amine functional groups. The surface charge and the chemical nature of the outer dendrimer surface can be varied by changing the functional groups on the surface, for example, by reaction of some or all of the surface amine groups. Of particular interest are dendrimers that are functionalized by reaction with cationic amino acids, such as lysine or arginine. Grafted dendrimers as described, for example in PCT applications WO 9622321 and WO9631549 and noted in U.S. Pat. No. 5,266,106, can be employed in the compositions and methods of this invention.

The methods of the present invention involve contacting a eukaryotic cell with a transfecting composition comprising peptide, including a fusagenic, membrane-permeabilizing, sub-cellular-localization, or receptor-ligand peptide, optionally conjugated to a nucleic acid-binding group, or optionally conjugated to the transfection agent (lipid or dendrimer) wherein said peptide or modified peptide is non-covalently associated with the nucleic acid. In one embodiment, a peptide-nucleic acid complex (where the peptide can be conjugated to a nucleic-acid binding group) is formed and then combined with a cationic lipid for transfection. In a related embodiment, a peptide-lipid conjugate is combined optionally with other lipids, including an appropriate cationic lipid, and then combined with nucleic acid for transfection. In a second embodiment, a peptide-nucleic acid complex (where the peptide can be conjugated to a nucleic-acid binding group) is formed and then combined with a dendrimer for transfection. In a related embodiment, a peptide-dendrimer conjugate is combined optionally with other dendrimers and then combined with nucleic acid for transfection. Dendrimers and/or peptide-conjugated dendrimers can be combined with cationic lipids and cationic lipid composition to obtain improved nucleic acid transfection compositions.

Methods of this invention employ among others, a viral peptide of influenza virus, vesicular stomatitis virus or simian virus 40 and more generally an RGD-peptide sequence, an NLS peptide sequence and/or a VSVG-peptide sequence and to modified peptides of each of the foregoing. Methods of this invention are applicable to transfection of adherent or suspension cell lines, in general to animal cell lines, specifically to mammalian, avian, reptilian, amphibian and insect cell lines and more specifically to animal primary cell lines, human primary cell lines, stem cell lines, and fibroblasts.

In one specific embodiment, a transfection-enhancing peptide is first bound to a nucleic acid to be introduced into a cell. The peptide-nucleic acid complexes are then admixed with transfection agent and the resulting mixture is employed to transfect cells. Preferred transfection agents are cationic lipid compositions, particularly polycationic lipid compositions, and more particularly "LIPOFECTAMINE", and dendrimer compositions, particularly G5–G10 dendrimers, including dense star dendrimers, PAMAM dendrimers, grafted dendrimers, and dendrimers known as dendrigrafts.

In a second specific transfection method, a transfection-enhancing peptide is conjugated to a nucleic acid-binding group, for example a polyamine and more particularly spermine, to produce a modified peptide which is then bound to the nucleic acid to be introduced into the cell. The modified peptide-nucleic acid complexes are then admixed with transfection agent and the resulting mixture is employed to transfect cells. In particular, the peptide is covalently conjugated to spermine, the spermine-modified peptide is complexed with nucleic acid and admixed with a cationic lipid. Preferentially, the transfection agent is a cationic lipid composition, more particularly, it is a polycationic lipid composition and more particularly, it is "LIPOFECTAMINE" and dendrimer compositions, particularly G5–G10 dendrimers, including dense star dendrimers, PAMAM dendrimers, grafted dendrimers, and including dendrimers known as dendrigrafts.

In a third specific embodiment, a mixture of one or more transfection-enhancing peptides, including fusagenic peptides, receptor-ligand peptides or nuclear localization peptides and/or their modified analogs (e.g., spermine modified peptides) is mixed with and complexed with nucleic acid to be introduced into a cell. The peptide-nucleic acid complexes are then admixed with transfection agent and the resulting mixture is employed to transfect cells.

In another specific embodiment, transfection agents (lipids, cationic lipids or dendrimers) are covalently conjugated to selected peptides directly or via a linking or spacer group. Of particular interest in this embodiment are peptides that are fusagenic, membrane-permeabilizing, or which function for cell-targeting. The peptide-transfection agent complex is combined with nucleic acid and employed for transfection.

The transfection methods of the present invention can be applied to in vitro and in vivo transfection of eukaryotic cells, particularly to transfection of higher eukaryotic cells including animal cells. The methods of this invention can be used to generate transfected cells which express useful gene products. The methods of this invention can also be employed as a step in the production of transgenic animals. The methods of this invention are useful as a step in any therapeutic method requiring introduction of nucleic acids into cells including methods of gene therapy and viral inhibition and for introduction of antisense or antigene nucleic acids or ribozymes or RNA regulatory sequences or related inhibitory or regulatory nucleic acids into cells. In particular, these methods are useful in cancer treatment, in in vivo and ex vivo gene therapy, and in diagnostic methods.

The transfection compositions of this invention comprising peptides, proteins, peptide fragments or modified-peptides, proteins or peptide fragments, can also be employed as research reagents in any transfection of eukaryotic cells done for research purposes. The transfection compositions can, with appropriate choice of physiologic medium, be employed in therapeutic and diagnostic applications.

Components of the transfection compositions of this invention can be provided in a reagent kit. In one embodiment comprising individual portions of cationic lipid and peptide or modified peptide. In a second embodiment comprising individual portions of dendrimer and peptide or modified peptide. Cationic lipid transfection kits can optionally include neutral lipid as well as other additives and the relative amounts of components in the kit may be adjusted to facilitate preparation of transfection compositions. Kit components can include appropriate medium or solvents for other kit components. Cationic lipid transfection kits can optionally include neutral lipid as well as other additives and the relative amounts of components in the kit may be adjusted to facilitate preparation of transfection compositions. Cationic lipid transfection kits comprising a polycationic lipid composition including a neutral lipid and a modified peptide are preferred. Dendrimer transfection kits can optionally include other transfection enhancing agents, such as DEAE-dextran and/or chloroquine, as well as other additives and the relative amounts of components in the kit may be adjusted to facilitate preparation of transfection compositions. Dendrimer transfection kits comprising a G5–G10 dendrimer or a Lys- or Arg-modified dendrimer or dendrigraft in combination with a peptide or a modified peptide are preferred. Kits provided by this invention include those comprising an individual portion of a polycationic lipid composition comprising DOSPA and DOPE and a portion of modified peptide, particularly a spermine-modified peptide. Kits provided by this invention include those comprising an individual portion of a dendrimer and a portion of a spermine-modified peptide.

In related embodiments, kits of this invention can comprise a peptide-lipid conjugate or a peptide-dendrimer conjugate in combination with non-conjugated lipids, non-conjugated dendrimers and other agents to facilitate transfection.

Nucleic acids that can be transfected by the methods of this invention include DNA and RNA of any size from any source comprising natural bases or non-natural bases, and include those encoding and capable of expressing therapeutic or otherwise useful proteins in cells, those which inhibit undesired expression of nucleic acids in cells, those which inhibit undesired enzymatic activity or activate desired enzymes, those which catalyze reactions (ribozymes), and those which function in diagnostic assays.

The compositions and methods provided herein can also be readily adapted in view of the disclosure herein to introduce biologically-active macromolecules other than nucleic acids including, among others, polyamines, polyamine acids, polypeptides and proteins into eukaryotic cells. Other materials useful, for example as therapeutic agents, diagnostic materials, research reagents, which can be bound to the peptides and modified peptides and introduced into eukaryotic cells by the methods of this invention.

BRIEF DESCRIPTION OF THE FIGURES

FIGS. 3A, C, E, and G: no Sp-NLSNLS; FIGS. 3B, D, F and H: 1–4 µg Sp-NLSNLS/well, precomplexed with DNA.

DETAILED DESCRIPTION OF THE INVENTION

Figure 1:
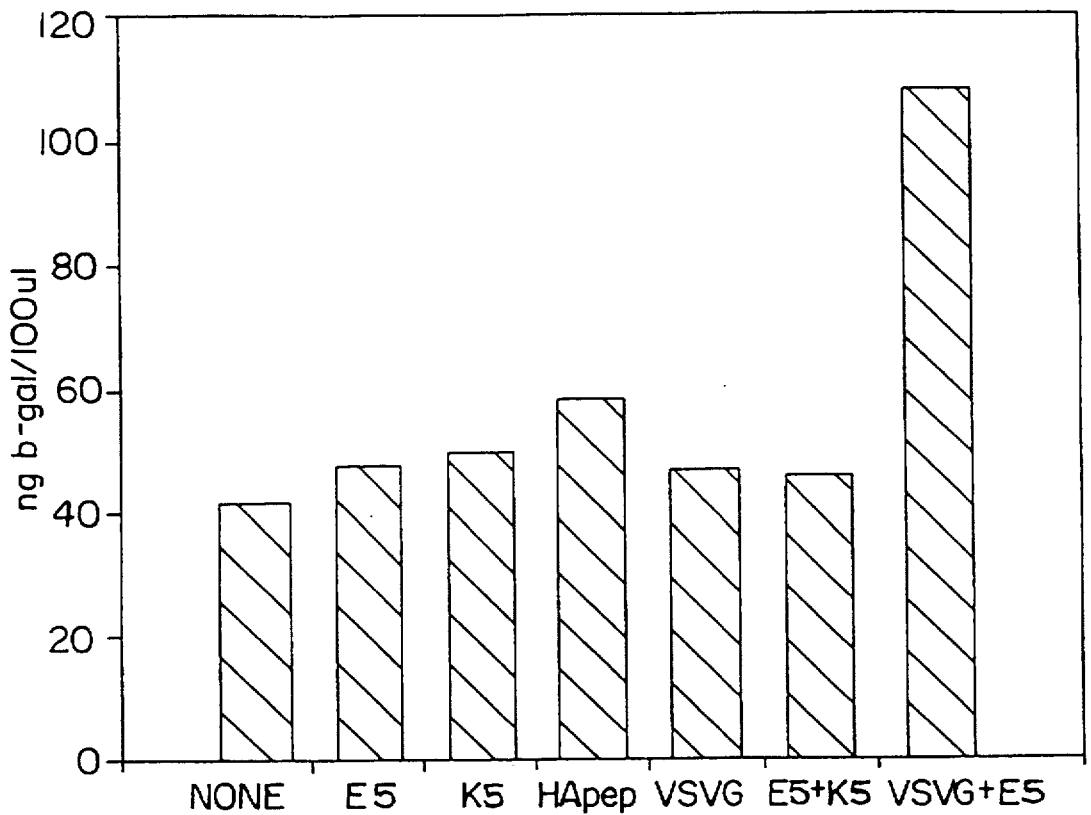
FIG. 1 is a bar graph showing enhancement of transfection of human fibroblast cells with various peptides added to "LIPOFECTAMINE"-DNA transfection mixtures.

The present invention provides improved methods for transfecting eukaryotic cells with nucleic acids by employing peptides or modified peptides in combination with transfection agents, e.g., cationic lipids and dendrimers. The improvement relates in one aspect to the use of a peptide-nucleic acid complex to enhance the efficiency of cationic lipid-mediated or dendrimer-mediated transfection. The peptide-nucleic acid complex comprises peptide bound to nucleic acid or a peptide modified to be covalently conjugated to a nucleic acid-binding group which is then bound to nucleic acid. This invention has significant advantages over prior art methods of transfection which employ cationic lipids or dendrimers for transfection. The peptides of this invention include fusagenic peptides, membrane-permeabilizing peptides, nuclear localization peptides, and receptor-ligand peptides, among others. Receptor-ligand peptides include among others cell-adhesion peptides, cell-targeting peptides, internalization-triggering peptides, and endocytosis-triggering peptides. Peptides useful in this invention can include peptide sequences functional for fusion (fusagenic sequences), sub-cellular localization or which mediate binding to a receptor. A peptide may be multi-functional comprising sequences with more than one of these functions. Peptides are optionally covalently coupled to a nucleic-binding group including a polyamine and form a complex with the nucleic acid. Peptide-complexed nucleic acids are more efficiently transported into the cells and the cell nucleus, thus enhancing the efficiency of cationic lipid- or dendrimer-mediated cell transfection. Because of the improved efficiency of transfection, considerably less nucleic acid is required for effective transfection. Transfection compositions of this invention, by virtue of complex formation between the nucleic acid and peptide or modified peptide, provide enhanced transfection as compared to prior art cationic lipid and dendrimer transfection compositions.

Another aspect this invention relates to improved efficiency of transfection using peptide conjugates in which a selected peptide is covalently linked to a dendrimer or to a lipid that will be a component in a cationic lipid transfection composition. The peptide conjugated transfection agent is then employed in transfections as is known in the art for the non-conjugated transfection agent.

The following definitions are employed in the specification and claims.

The term "transfection" is used herein generally to mean the delivery and introduction of biologically functional nucleic acid into a cell, e.g., a eukaryotic cell, in such a way that the nucleic acid retains its function within the cell. Transfection methods of this invention may be applied to cells in vitro or in vivo. The term transfection includes the more specific meaning of delivery and introduction of expressible nucleic acid into a cell such that the cell is rendered capable of expressing that nucleic acid. The term expression means any manifestation of the functional presence of the nucleic acid within a cell, including both transient expression and stable expression. Nucleic acids include both DNA and RNA without size limits from any source comprising natural and non-natural bases. Nucleic acids can have a variety of biological functions. They may encode proteins, comprise regulatory regions, function as inhibitors of gene or RNA expression (e.g., antisense DNA or RNA), function as inhibitors of proteins, function to inhibit cell growth or kill cells, catalyze reactions or function in a diagnostic or other analytical assay.

Transfection efficiency is "enhanced" when an improvement of at least about 5 percent, preferably about 10 percent, and more preferably about 20 percent in efficiency is shown using the protocols for measuring nucleic acid biological function set forth in the examples hereof. Transfection is substantially enhanced when at least about a 2-fold (i.e. 100% or more) improvement of efficiency is measured as described herein.

The term "nucleic acid-binding group" is used herein generally to mean a protein, peptide, polypeptide or polyamine which is capable of non-covalently associating with nucleic acids. Nucleic acid-binding groups included DNA-binding groups. Binding of the nucleic acid-binding group to the nucleic acid can be specific to the sequence of the nucleic acid, or non-specific to its sequence. Although the mechanism of association depends upon the particular binding group, sequence specificity generally results from an ensemble of mutually favorable interactions between a binding group and its target DNA. Some DNA-binding groups, for example, interact with the DNA's paired bases and sugar-phosphate chains through direct contacts, including hydrogen bonds, salt bridges and van der Waals forces. Other groups function through sequence-specific conformational variations in DNA (or more generally nucleic acid) rather than from sequence-specific hydrogen bonding interactions between nucleic acid and protein. It will be understood that the term "nucleic acid-binding group" includes any protein, peptide, polypeptide or polyamine which is capable of binding nucleic acid, without regard to the mechanism of binding. Nucleic acid-binding groups are known to the art and widely available in commerce.

The term "peptide" as used herein is intended to be a generic term which broadly includes short peptides (typically less than 100 amino acids). Peptide used generically herein also includes peptides modified with nucleic acid-binding groups or peptides which retain amino acid protecting groups, such as the Mtr group. Longer peptide polypeptides (typically more than 100 amino acids, and proteins (which contain one or more polypeptide chains) which function as transfection enhancing agents having fusagenic, cell-receptor ligand or sub-cellular localization function, can be substituted for the peptides and of this invention and can also be modified with nucleic acid-binding groups. The peptides of this invention typically have more than two amino acids; preferred peptides have more than 4 amino acids.

The peptides of this invention have biological function as fusagenic peptides, membrane-permeabilizing peptides, sub-cellular-localization peptides, and receptor-ligand peptides. Two or more peptide functions can be combined into the same peptide, for example, by automated peptide synthesis.

The term spermine is used to describe the molecule spermine, but also to describe peptides that are modified to be covalently linked to a spermine, as in the term "spermine-modified" peptide. Spermine may be linked directly or indirect through intervening covalent bonds to the peptide. Spermine-modified peptide can be used generically to describe modified peptides containing a linker to spermine. For example, the term spermine-modified also refers to peptides that are linked to carboxyspermine.

Receptor-ligand peptides of this invention include those protein fragments or peptides which bind to cell-surface or other membranes or which bind to soluble receptor molecules and which optionally have another biological function and which optionally trigger internalization or endocytosis. Receptor-ligand peptides include cell-adhesion peptides, and cell targeting peptides.

Receptor-ligand peptides also include adhesion peptides. Adhesion peptides do not typically trigger endocytosis. Adhesion peptides can be derived from adhesion proteins including fibronectin, vitronectin, tenascin, laminins, collagens, thrombospondins, fibrinogens and functional equivalents. Table 1 provides examples of adhesion proteins and peptides.

Fragments of adhesion proteins include RGD sequence-containing peptides (RGD peptides) as listed in Table 1. The CS-1 peptide, sequence given in Table 1, is obtained from a 38 kD tryptic fragment of plasma fibronectin containing the carboxyl-terminal Heparin II domain and part of the type III connecting segment (IIICS) (Wayner, E. A. et al. (1989) "Identification and Characterization of T Lymphocyte Adhesion Receptor for an Alternative Cell Attachment Domain (CS-1) in Plasma Fibronectin" J. Cell Biol. 109:1321–1330.)

Receptor ligand peptides also include those that trigger internalization and/or endocytosis. For example, Penton Base is a pentamer coat protein of adenovirus that contains five copies of the integrin receptor binding motif, Arg-Gly-Asp (RGD). Penton Base is used by the virus to bind integrins $\alpha_v\beta_3$ and $\alpha_v\beta_5$. Following adenovirus attachment to cells by the fiber coat protein, the integrin receptors mediate virus internalization in to the host cells. The Penton Base (wild-type) RGD sequence is HAIRGDTFAT (SEQ ID NO 1) (Wickham, T. J. et al. (1995) Gene Therapy 2:750–756.)

Adhesive peptides include RGD peptides which are peptides containing the tripeptide sequence Arg-Gly-Asp which can duplicate or inhibit the cell attachment promoting effects of fibronectin or vitronectin (Pierschbacher, M. D., and Ruoslahti, E. (1987) J. Biol. Chem. 262:17294–8), or other peptides with similar binding motifs.

Receptor-ligand peptides of this invention include those peptides that have an affinity for or binding to, receptor molecules that are broadly expressed in a variety of cell types, such as those peptides that bind to integrin $\alpha_v\beta_5$. Receptor-ligand peptides of this invention also include those peptides that bind to receptor molecules that are specifically expressed in a limited number of cell types (e.g. tissue-specific) or highly expressed in a particular cell type (e.g., in cancer cells, such as those that bind to the integrin $\alpha_v\beta_5$, which is highly expressed in certain melanomas and glioblastoma).

Sub-cellular localization peptides include those that recognize, target or are directed to a particular sub-cellular component, e.g., the nucleus, mitochondria, etc. See: C. Dingwall et al. (1991) TIBS 16:478–481.

Most generally, any of the sequences exemplified in Table 1–3, or functional equivalents thereof can be employed as peptides or modified peptides to enhance transfection activity in the transfection compositions and methods of this invention. Specific examples of spermine-modified peptides are provided in Table 4.

Table 2 lists a variety of peptides that are useful in the present invention, including peptides with a single functional region and peptides combining two or more functional regions. Concatemers of single function peptides and mixed concatemers combining sequential repetitions of dual (or more) function peptides are listed and are useful in the present invention. The peptide formulas in Table 2 combine generic regions, e.g., spacers and linker groups with conserved amino acid sequence associated with a particular function. Not specifically listed in Table 2 are dimers and multimers of functional peptides, for example, dimers formed between two cysteine residues of peptides. Dimers and multimers of functional peptides are useful in this invention.

Table 2 also lists cyclic peptides and cysteine peptide precursors of cyclic peptide that contain a functional peptide sequence of this invention (NLS, VSVG, RGD, LDV, E5, K5, etc.).

Table 3 provides a number of specific peptide sequences that are useful in the methods and compositions of this invention for enhancement of transfection. The table includes a number of specific combinations of two functional peptide sequences with optional spacers and optional cationic tails (for binding to nucleic acids). One entry in the table, "NLS phosphorylation" relates to an NLS sequence coupled to a phosphorylation-site-containing sequence. This fusion has been described in H-P. Rihs et al. (1989) EMBO J. 8:1479–1484 and H-P Rihs et al. (1991) EMBO J. 10:633–639. The presence of the phosphorylation site enhances transport to the nucleus.

Table 3 also contains precursors to transfection enhancing peptides, HIS-TEV-peptides. These peptides contain a HIS tail and a TEV (Tobacco Etch Virus) protease recognition sequence in addition to the peptide sequence useful for transfection enhancement. TEV protease will specifically cleave the HIS tail from the peptide leaving the functional peptide sequence. This combination can be employed for the isolation and purification of fusion polypeptides as has been described in U.S. Pat. No. 5,532,142 which is incorporated by reference herein. Peptides with HIS tails can be selectively purified on Ni columns.

Table 3 also includes examples of peptides having $(D)_n$ tails, i.e., tails of anionic amino acids. These peptides are of particular interest for binding to the surface of positively charge lipid-nucleic acid aggregates to enhance transfection of the aggregates and the nucleic acid that is carried therein. The transfection method for use of these peptides with anionic tails involves initial formation of cationic lipid aggregates with nucleic acid by conventional methods followed by complexation to the anionic tailed peptide. These peptides can also be employed with dendrimer-nucleic acid complexes.

Those of ordinary skill in the art will appreciate that some amino acid sequence variation in functional peptides or modified peptides, such as those listed in Tables 1, 2 and 3, can be tolerated without significant loss of function. In many cases, substitutions of like amino acids , e.g., basic (cationic) amino acid for basic amino acid (e.g., K for R or R for K) or acidic (anionic) amino acid for acidic amino acid, in a given functional peptide will not significantly affect peptide function. In functional peptides containing a string of like amino acids, e.g., PKKKRKV (SEQ ID NO:2), addition or deletion of one or more amino acids from the string may be tolerated, e.g., PKKKKRKV (SEQ ID NO:3), without significant loss of peptide function. Variations that diverge the least from exemplified or art-known functional peptide sequences are generally preferred. For use in this invention, functional peptides can contain flanking strings of amino acids (preferably glycines) that do not affect function of the core peptide sequence. In an analogous way, a functional peptide sequence of this invention can be embedded within a larger peptide wherein the nature of the sequence external to the core functional sequence does not affect function of the core. This invention includes peptides which contain more than one distinct functional sequence, e.g., NLSVSVG or RGDNLS. In these peptides, the functional sequences can be separated by linker peptide regions (preferably one or more Gs). Peptides of this invention can include amino acids that are not part of a functional region which are added to the peptide to provide a site for chemical linkage to another species, e.g., cysteine can be used as a site for binding to spermine. In some cases, amino acids external to the functional core sequence can act as spacers or linker regions between the functional peptide and the species (lipid, dendrimer, polyamine, spermine, etc.) to which it is covalently attached. For example, cysteine residues included in a peptide can be oxidized to form —S—S— dimers or larger multimer (trimers, etc.) by oxidization. Two cysteines placed distal to each other in a peptide can be oxidized to prepare a cyclic peptide containing one or more functional amino acid sequences.

This invention also includes peptides containing functional groups that enhance transfection and also contain amino acids or amino acid sequences that are useful in the preparation, isolation and purification of the peptides themselves. For example, aromatic amino acids can be included in a peptide sequence to provide a UV absorption marker to allow convenient measurement of peptide concentration. Alternatively, transfection enhancing peptides can be provided with amino acid sequences that specifically bind to certain column materials to facilitate peptide purification. Certain transfection enhancing peptide may be more easily produced through expression of DNA in bacteria or other expression systems. Peptides of this invention can include amino acids sequences (or parts thereof) that are sites for selective proteases that are useful in isolation of the peptide from an expression system.

The term "modified-peptide" is used herein generally to mean a peptide which has been chemically modified to include a nucleic acid-binding group covalently attached thereto. The term "modified-peptide" as used herein includes "polyamine-peptide conjugate" wherein the covalently attached nucleic acid-binding, or more specifically a DNA-binding group, is a polyamine, including "spermine-modified peptide" wherein the DNA-binding group is spermine. In some cases, a peptide may itself bind to nucleic acid; in other cases modification of the peptide is necessary for or enhances binding to nucleic acid. For example, strings of cationic amino acids can be added to a functional peptide (at the C- or N-terminus) to facilitate biding to nucleic acid. These sequences can be written as $(Uaa)_u$, where u is an integer ranging typically from 1 to about 20 (and more preferably ranges from 8–20) and Uaa, independently of other Uaa's in the peptide, is a cationic amino acid, e.g., $(K)_u$[SEQ ID NO 4], $(R)_u$[SEQ ID NO 5], or $(KR)_u$[SEQ ID NO 6]. More generally, cationic amino acids strings for binding to nucleic acids can include non-cationic amino acids (preferably Gs) so long as the binding function is not significantly decreased.

Naturally-occurring peptides or proteins may require additional modification to allow conjugation to spermine or other polyamines. For example, cysteines may be added to the C-terminals or N-terminals of peptides or introduced within a peptide to facilitate conjugation. Likewise a string of spacer amino acids, i.e. $(G)_n$ [SEQ ID NO: 7], where n is an integer ranging most generally from 1-about 20, can be added between a peptide and the species to which it is covalently linked. Any peptide modification used to facilitate conjugation preferably does not substantially affect peptide binding or function.

The term "peptide-nucleic acid complex" generally refers to the noncovalent association between a peptide and a nucleic acid. The peptide of this complex may be a modified peptide as defined above. As used herein in certain embodiments of transfection methods, a "peptide-nucleic acid complex" is formed prior to the addition of cationic lipid or dendrimer to a transfection composition.

"Lipid aggregate" is a generic term that includes liposomes of all types both unilamellar and multilamellar as well as vesicles, micelles and more amorphous aggregates. A cationic lipid aggregate is a lipid aggregate comprising sufficient cationic lipid, optionally in combination with non-cationic (e.g., neutral) lipids, such that the lipid aggregate has a net positive charge. Cationic lipids and lipid aggregates are capable of aggregating the peptide-nucleic acid complexes of the invention.

Cationic lipid composition includes those compositions comprising a cationic lipid or a mixture of cationic lipids, which can be either monovalent or polyvalent cationic lipids. The cationic lipid composition optionally contains neutral lipids. Of particular interest are cationic lipid compositions recognized in the art as useful in transfection methods. Preferred cationic lipid compositions comprise polyvalent cationic lipids; more preferred are those compositions containing DOSPA and its analogs or homologs; the most preferred cationic composition is "LIPO-FECTAMINE".

Transfection activity or efficiency is measured by detecting the presence of the transfected nucleic acid in a cell. This is often assessed by measuring the biological function of the nucleic acid in the cell, and most often assessed by measuring the level of transient or stable expression of a reporter gene comprised in the transfected nucleic acid. Reporter gene expression depends among other things on the amount of nucleic acid transfected as well as promoter function in the cell. Transfection activity can also be assessed by determining the percent of cells in a sample that have been transfected, for example, by assessing reporter gene expression using cell counting or in situ staining methods. The transfection methods of this invention employing peptides in combination with cationic lipids can display significant enhancement of transfection (2-fold or more) over transfection methods employing comparable cationic lipids alone.

The method of this invention involves contacting a eukaryotic cell with a transfection composition comprising a peptide-nucleic acid complex (or a modified peptide-nucleic acid complex) and a transfection agent, a cationic lipid or a dendrimer. A cationic lipid transfection composition optionally comprises a non-cationic lipid, preferably a neutral lipid. Cationic lipid transfection compositions can optionally comprise known transfection enhancing agents in addition to peptide or modified peptides, including, for example chloroquine, a lysosomotrophic agent. Dendrimers or mixtures thereof can be employed in transfection compositions. Dendrimer transfection compositions may include agents other than peptides or modified peptides that are known to enhance dendrimer-mediated transfection, e.g., DEAE-dextran and/or chloroquine. The peptide can be a fusagenic peptide of a viral protein. A preferred fusagenic peptide is that of influenza virus or vesicular stomatitis virus (VSVG). The peptide can be a sub-cellular localization signal peptide. A preferred nuclear localization signal peptide is that of simian virus 40, particularly the nuclear localization sequence (NLS) of the SV40 large T antigen. Kalderon et al. (1984) Cell 39:499; and Lanford et al. (1986) Cell 46:575. There is some diversity in the sequences of nuclear localization signals as reported in C. Dingwell and R. A. Laskey (1991) TIBS:478–481, which is incorporated by reference herein for the sequences disclosed. This invention includes peptides comprising nuclear localization sequences as disclosed therein. The peptide of this invention can be a receptor-ligand peptide. Preferred receptor-ligand peptides are cell adhesion peptides, particularly RGD peptides. Transfecting compositions comprising peptides of viral proteins conjugated to a nucleic acid-binding group are particularly preferred. Preferred nucleic acid-binding groups are spermines and the cationic amino acid strings $(K)_u$ and $(R)_u$, where u is an integer from 1 to about 20 and more preferably is about 8 to about 20.

Enhanced transfection methods of this invention are demonstrated with the prototype nuclear localization signal peptide from simian virus 40 and the prototype fusagenic peptides from influenza (HApep; E5 and K5 amphophilic peptides), vesicular stomatitis virus (G protein) and an RGD peptide (GRGDSPC [SEQ ID NO 8]) taken from the cell attachment site of fibronectin. The DNA-binding group that has been employed is a polyamine capable of forming a noncovalent association with the base pairs of the nucleic acid. Enhanced transfection methods of this invention have been further exemplified using the prototype DNA-binding group, spermine.

In some cases, the peptides form a direct noncovalent association or complex with the nucleic acid. This peptide-nucleic acid complex forms as a consequence of conformational or charge interactions between the peptide and the base pairs of the DNA. A peptide-nucleic acid complex forms spontaneously in an appropriate medium. Transfection compositions comprising these peptide-nucleic acid complexes are prepared by first interacting the nucleic acid with the peptide followed by addition of the resulting complex to a cationic lipid composition or a dendrimer.

The peptides of this invention, when covalently coupled to a nucleic acid-binding group (modified-peptide), can form a noncovalent association or complex with the nucleic acid. This modified-peptide-nucleic acid complex forms as a consequence of conformational or charge interactions between the nucleic acid-binding group and the nucleic acid (DNA or RNA). For example, the prototype spermine-peptide-nucleic acid complex likely forms as a consequence of charge interactions between the amines of spermine and the phosphates on the DNA backbone. A modified-peptide-nucleic acid complex forms spontaneously in an appropriate medium. Transfection compositions comprising these modified-peptide-nucleic acid complexes are prepared by first interacting the nucleic acid with the modified peptide to form complexes followed by addition of a cationic lipid composition.

In one embodiment, a composition containing the peptide-nucleic acid or modified-peptide-nucleic acid complex is admixed with a cationic lipid, alone or in combination with a non-cationic lipid, to form a peptide-nucleic acid-lipid aggregate. A peptide-nucleic acid-lipid aggregate forms spontaneously in an appropriate medium or various well-known techniques may also be employed to produce a desired type of lipid aggregate. The relative amounts of cationic lipid and non-cationic lipid employed depends on a number of factors, including the cell type to be transfected, toxicity of the lipids to the cell and the environment (e.g. medium) in which the aggregate is to be employed. The kinds and amounts of lipids employed is typically balanced for a given cell type to minimize cell toxicity and maximize transfection efficiency.

In another embodiment, peptide-nucleic acid or modified-peptide-nucleic acid complexes are admixed with a dendrimer (or mixture of dendrimers) to form a peptide-nucleic acid-dendrimer aggregate. This aggregate forms spontaneously in a appropriate medium. The relative amounts of dendrimer to nucleic acid are adjusted to optimize transfection in a given cell type in a given environment. The chemical type, size and shape of the dendrimer is also selected to optimize transfection in a given cell type.

Nucleic acid delivery can be enhanced by the use of cell targeting, cell adhesion or binding peptides. Peptides containing the RGD sequence can be coupled to the polycation spermine which acts as a DNA binding group. The RGD-spermine peptide is believed to enhance transfection via cell targeting, and more importantly, cell adhesion. Attachment to adhesion proteins, and in some cases to other cells, is often mediated by integrins. Many adhesive proteins present in extracellular matrices and in the blood contain the tripeptide arginine-glycine-aspartic acid (RGD), as their cell recognition site (Ruoslahti, E. and Pierschbacher, D. (1987) Science 238:491). Pathogens such as bacteria, and more specifically, foot and mouth disease virus (FMDV) (Mason et al. (1994), Proc. Natl. Acad. Sci. 91, 1932–1936) and Adenovirus (Wickham, T. J. et al (1995), "Targeting of adenovirus penton base to new receptors through replacement of its RGD motif with other receptor-specific peptide motifs," in Gene Therapy 2: 750–756) have RGD containing proteins expressed on their surface, which interact with integrins on the host cell and facilitate internalization. RGD, $(K)_u$ RGD (particularly where u=16) and RGD-spermine peptide can enhance "LIPOFECTAMINE"-mediated transfection or dendrimer-mediated transfections.

Viral peptides can be isolated by a variety of well-known techniques, for example using the cationic detergent DTAB as described in Glushakova, S. E., et al. (1985) "Influenza viral glycoproteins isolation using cationic detergent dodecylmethylammonium bromide and its subsequent internalization into liposomal membrane" Mol. Genet. Microbiol. Virol. 4:39–44. Alternatively, viral peptides, as well as functional peptides from other sources, can be produced by a variety of standard chemical synthetic methods. Functional peptides, for example, can be synthesized using automated solid phase peptide synthesis as described, e.g., in Stewart et al. (1984) *Solid Phase Peptide Synthesis*, Pierce Chemical Company, Rockford, Ill. Fusagenic peptides from influenza and vesicular stomatitis virus, including the exemplified hemagglutinin peptide, K5 and E5 amphophilic peptides and G protein, are particularly useful in the methods of this invention. Nuclear localization signal peptides from simian virus 40, including the exemplified NLS peptide, are also preferred. Peptides can be used alone or in combination with other functional peptides in the methods of this invention. As illustrate in Table 2, two or more functional peptide sequences (optionally separated by linkers or spacers) can be combined in a given peptide.

Modified-peptides can be prepared by a variety of well-known coupling techniques, for example using a heterobifunctional cross-linking agent as described in the Examples hereof. A variety of cross-linking agents are known to the art and widely available in commerce including, without limitation, succinimidyl or maleimidyl cross-linkers, such as Sulfosuccinimidyl 4-(p-maleimidophenyl)butyrate (Sulfo-SMPB), disuccinimidyl suberate, succinimidyl 4-(p-maleimidophenyl)butyrate (SMPB), 4-succinimidyloxycarbonyl-α-methyl-α-(2-pyridyldithio)-toluene (SMPT), Sulfosuccinimidyl 6-[3-(2-pyridyldithio) propionamido]hexanoate (Sulfo-LC-SPDP), Succinimidyl 6-[3-(2-pyridyldithio)propionamido]hexanoate (LC-SPDP), N-Succinimidyl 3-(2-pyridyldithio)propionate (SPDP), Sulfosuccinimidyl 4-(N-maleimidomethyl)cyclohexane-1-carboxylate (Sulfo-SMCC), Succinimidyl 4-(N-maleimidomethyl)cyclohexane-1-carboxylate (SMCC); m-Maleimidobenzoyl-N-hydroxysulfosuccinimide ester (Sulfo-MBS), m-Maleimidobenzoyl-N-hydroxysuccinimide ester (MBS), Sulfosuccinimidyl(4-iodoacetyl) aminobenzoate (Sulfo-SIAB), N-Succinimidyl(4-iodoacetyl)aminobenzoate (SIAB). Methods for conjugating peptides and polyamines are well-known in the art. Representative methods are disclosed in Staros, J. V. (1982) Biochemistry 21:3990. Any of the functional peptides exemplified herein, or functional equivalents thereof, can be modified by covalent coupling to a nucleic acid-binding agent, e.g., to a polyamine and preferably to spermine.

Covalent linking of a peptide to a lipid or a dendrimer can be performed by a variety of conventional methods using known coupling agents and known derivatiztion methods.

Media employed in transfections should preferably be free of components, like serum or high salt levels, that can inhibit cationic lipid-mediated or dendrimer-mediated transfection of cells.

A variety of cationic lipids is known in the art. Generally, any cationic lipid, either monovalent or polyvalent, can be used in the compositions and methods of this invention. Polyvalent cationic lipids are generally preferred. Cationic lipids include saturated and unsaturated alkyl and alicyclic ethers and esters of amines, amides or derivatives thereof. Straight-chain and branched alkyl and alkene groups of cationic lipids can contain from 1 to about 25 carbon atoms. Preferred straight-chain or branched alkyl or alkene groups have six or more carbon atoms. Alicyclic groups can contain from about 6 to 30 carbon atoms. Preferred alicyclic groups include cholesterol and other steroid groups. Cationic lipids can be prepared with a variety of counter ions (anions) including among others: $Cl^-$, $Br^-$, $I^-$, $F^-$, acetate, trifluoroacetate, sulfate, nitrite, and nitrate.

A well-known cationic lipid is N-[1-(2,3-dioleoyloxy)-propyl]-N,N,N-trimethylammonium chloride (DOTMA). See Felgner, P. L. et al. (1987) Proc. Natl. Acad. Sci. USA 84:7413–7417. DOTMA and the analogous diester DOTAP (1,2-bis(oleoyloxy)-3-3-(trimethylammonium)propane) are commercially available. Additional cationic lipids structurally related to DOTMA are described in U.S. Pat. No. 4,897,355, which is incorporated by reference in its entirety herein.

Other useful groups of cationic lipids related to DOTMA and DOTAP are commonly called DORI-ethers or DORI-esters. DORI lipids differ from DOTMA and DOTAP in that one of the methyl groups of the trimethylammonium group is replaced with a hydroxyethyl group. The DORI lipids are similar to the Rosenthal Inhibitor (RI) of phospholipase A (Rosenthal, A. F. and Geyer, R. P. (1960) J. Biol. Chem. 235:2202–2206). The oleoyl groups of DORI lipids can be replaced with other alkyl or alkene groups, such as palmitoyl or stearoyl groups. The hydroxyl group of the DORI-type lipids can be used as a site for further functionalization, for example for esterification and/or for ether formation.

Additional cationic lipids which can be employed in the compositions and methods of this invention include those described as useful for transfection of cells in PCT application WO 91/15501 published Oct. 17, 1991, Pinnaduwage, P. et al. (1989) Biochem. Biophys. Acta. 985:33–37; Rose, J. K. et al. (1991) BioTechniques 10:520–525; Ito, A et al. (1990) Biochem, Intern, 22:235–241.

The polycationic lipid formed by conjugating polylysine to DOPE (Zhou, X. et al. (1991) Biochem. Biophys. Acta 1065:8–14), as well as other lipopolylysines, can also be employed in the methods and compositions of this invention.

Polycationic lipids containing carboxyspermine are also useful in the compositions and methods of this invention. Behr, J-P. et al. (1989) Proc. Natl. Acad. Sci. 86:6982–6986 and EPO published application 304 111 (1990) describe carboxyspermine-containing cationic lipids including 5-carboxyspermylglycine dioctadecyl-amide (DOGS) and dipalmitoylphosphatidylethanolamine 5-carboxyspermylamide (DPPES). Additional cationic lipids can be obtained by replacing the octadecyl and palmitoyl groups of DOGS and DPPES, respectively, with other alkyl or alkene groups. Polycationic lipids designated DOSPER (See: Formula B for specific and generic formula) are also useful in the methods of this invention. U.S. Pat. No. 5,334,761, which is incorporated by reference in its entirety herein, also describes cationic lipids, including DOSPA (see: Formula A for specific and generic formula) which are useful in this invention.

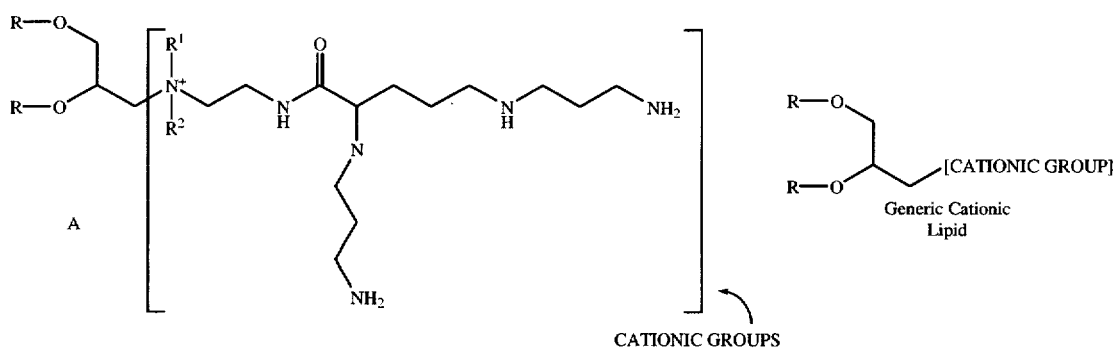

A

CATIONIC GROUPS

Generic Cationic Lipid

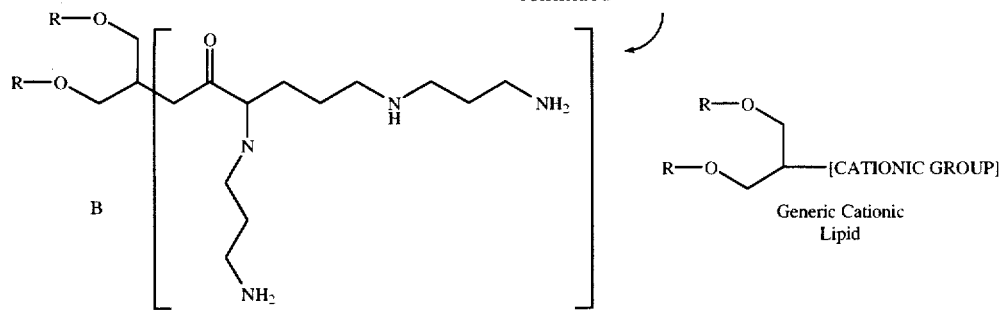

Generic Cationic Lipid

PCT application WO 95/17373 describes highly packed polycationic ammonium, sulfonium and phosphonium lipids that are useful for transfection. These cationic lipids are useful in methods of this invention.

In the transfection compositions of this invention cationic lipids can optionally be combined with non-cationic lipids, preferably neutral lipids, to form lipid aggregates that bind to the modified-peptide-nucleic acid complex. Neutral lipids useful in this invention include, among many others: lecithins; phosphotidylethanolamine; phosphatidylethanolamines, such as DOPE (dioleoylphosphatidylethanolamine), DPPE (dipalmitoylphosphatidylethanolamine), dipalmiteoylphosphatidylethanolamine, POPE (palmitoyloleoylphosphatidylethanolamine) and distearoylphosphatidylethanolamine; phosphotidylcholine; phosphatidylcholines, such as DOPC (dioleoylphosphidylcholine), DPPC (dipalmitoylphosphatidylcholine) POPC (palmitoyloleoylphosphatidylcholine) and distearoylphosphatidylcholine; phosphatidylglycerol; phosphatidylglycerols, such as DOPG (dioleoylphosphatidylglycerol), DPPG (dipalmitoylphosphatidyl-glycerol), and distearoylphosphatidylglycerol; phosphatidylserine; phosphatidylserines, such as dioleoyl- or dipalmitoylphosphatidylserine; diphosphatidylglycerols; fatty acid esters; glycerol esters; sphingolipids; cardolipin; cerebrosides; and ceramides; and mixtures thereof. Neutral lipids also include cholesterol and other 3βOH-sterols.

Dendrimers can be prepared by several now well-documented methods. See: WO95/24221; D. A. Tomalia and H. D. Durst (1993) in E. Weber (ed.) Topics in Current Chemistry, Vol. 165: Supramolecular Chemistry I-Directed Synthesis and Molecular Recognition, Springer-Verlag, Berlin, pp.193–313; U.S. Pat. Nos. 5,527,524; 5,338,532; 4,694,064; 4,568,737; 4,507,466; and PCT patent applications; WO8801179; WO8801178; and WO9502397. "STARBURST" (Trademark, Dendritech, Inc.) or dense star polyamidoamine (PAMAM) dendrimers including those having cationic amino acids or other cationic species at their outer surface are preferred for transfection methods of this invention. Transfection protocols for use with dendrimers and a discussion of the choice of a given dendrimer for a given transfection is given in J. F. Kukowska-Latolla et al. (1996) Proc. Natl. Acad. Sci. USA 93:4897–4902, A. Bielinska et al. (1996) Nucleic Acids Res. 24(11):2176–2182; WO9524221; WO9319768 and WO9502397.

The present invention is based on the discovery that certain peptides or modified peptides can significantly enhance the efficiency of transfection of eukaryotic cells with nucleic acids. The peptide or modified peptide binds to the DNA and functions as a fusagenic peptide, functions for sub-cellular localization or for cell adhesion. Peptides, optionally modified, if necessary or desirable, to enhance binding to nucleic acids, that function as internalization-triggering signals or endocytosis-triggering signals, also function in the transfection methods of this invention. The compositions and methods of the invention comprise peptides, optionally modified covalently with a nucleic acid-binding group, which significantly improve the efficiency of transfection when bound to nucleic acid prior to adding the transfection reagent. These bound nucleic acids are more efficiently transported into the cell and to the cell nucleus, thus requiring less nucleic acid starting material. Although the present invention is exemplified using a cationic lipid delivery system or a dendrimer delivery system, fusagenic, sub-cellular localization peptides and cell-targeting peptides are effective in enhancing transfection using a variety of known delivery systems. The present invention thus provides improved methods of transfection using these peptides and modified peptide, including peptides covalently conjugated to dendrimers or peptides covalently conjugated to lipids, to enhance transfection by other nucleic acid delivery means including, without limitation, electroporation (T. K. Wong and E. Neumann (1982) Biochem. Biophys. Res. Commun. 107:584 and E. Neumann et al. (1982) EMBO J 1:841), calcium phosphate (F. L. Graham and A. J. Vander Eb (1973) Virology 52:456), microinjection (M. R. Capecchi (1920) 22:479), ballistic transformation using microscopic particles coated with DNA (D. T. Tomes et al. (1990) Plant Mol. Biol. Manual A13:1–22 and G. N. Ye et al. (1990) Plant. Molec. Biol. 15:809) DEAE-dextran (A. Vaheri and J. S. Pagano (1965) Science 175:434), and polybrene-DMSO (S. Kawai and M. Nishizawa (1984) Molec. Cell. Biol. 4:1172).

Transfection compositions of this invention include compositions for transfecting eukaryotic cells using a peptide or protein comprising a nuclear localization sequence, a fusagenic peptide or receptor-ligand peptide sequence covalently attached to a polycation. Peptides having a nuclear localization sequence, fusagenic peptide or receptor-ligand signal attached to a polycation, are also a part of the invention. Preferred linkers include, for example, heterobifunctional crosslinkers. The polycation is preferably a polyamine and most preferable, spermine. As previously discussed, the transfection compositions and peptides of the invention are useful with a wide variety of delivery systems including, without limitation, electroporation, calcium phosphate, microinjection, ballistic transformation, DEAE-dextran and polybrene-DMSO. The present invention thus includes methods for transfecting a eukaryotic cell with a nucleic acid, the method generally comprising the steps of (1) admixing a peptide or modified peptide with a nucleic acid to form a peptide-nucleic acid complex; and (2) introducing the peptide-nucleic acid complex from step (1) into the cell using a known delivery means. One of ordinary skill in the art, based on knowledge generally available to the art including the present disclosure, can use the compositions and peptides of the present invention with any delivery system without the expense of undue experimentation.

Kits comprising components of the transfection compositions of this invention can be employed to facilitate preparation and use of transfection compositions. Such kits can be provided and employed as research reagents for any transfection of eukaryotic cells done for research purposes. Kits can be configured with components adequate for use in single transfection or for multiple transfections. In one embodiment, kit components comprise a cationic lipid composition and a peptide or modified-peptide to enhance transfection. The cationic lipid composition comprises a cationic lipid and preferably a neutral lipid. Preferred cationic lipid compositions comprise a polycationic lipid. More preferred cationic lipid compositions comprise the polycationic lipid DOSPA or analogs and homologs of DOSPA. Preferred neutral lipids include DOPE and analogs or homologs thereof.

The level of transfection enhancement effected by a given peptide or modified peptide may vary dependent upon the cell type, components of the transfection agent, transfection method used, the order of addition of components to or the order of complexation of components in a transfection composition, among other factors. Those of ordinary skill in the art using the guidance and methods provided herein and with knowledge of procedures, assays and methods for transfection well-known in the art can select, without undue experimentation, a particular peptide or modified peptide of this invention for enhancement of transfection in a given system.

It will be readily apparent to those of ordinary skill in the art that a number of parameters are important for optimal transfection. For cationic lipid-mediated transfection, these parameters include cationic lipid concentration, relative amounts of cationic and non-cationic lipid, the concentration of nucleic acid, the medium employed for transfection, the length of time the cells are incubated with transfection composition, the amount of peptide employed, the amount of DNA-binding group or polyamine employed, and the way, e.g., order, in which the components of the transfection composition are combined. For dendrimer-mediated transfection, these parameters include dendrimer size, shape and chemical composition, the relative amount of dendrimer and nucleic acid, the addition of other transfection agents (DEAE-dextran, chloroquine), the concentration of nucleic acid, the medium employed for transfection, the length of time the cells are incubated with transfection composition, the amount of peptide employed, the amount of DNA-binding group or polyamine employed, and the way e.g., order) in which the components of the transfection composition are combined. It may be necessary to optimize these parameters for each cell type (for each kind of transfection system) to be transfected. Such optimization is routine employing the guidance provided herein and transfection assays as described in the Examples herein.

It will also be apparent to those of ordinary skill in the art that alternative methods, reagents, procedures and techniques other than those specifically detailed herein can be employed or readily adapted to produce the transfection compositions of this invention and practice the transfection methods of this invention. Such alternative methods, reagents, procedures and techniques are within the spirit and scope of this invention.

The transfection compositions and methods of this invention are further illustrated in the following non-limiting Examples. All abbreviations used herein are standard abbreviations in the art. Specific procedures not described in detail in the Examples are well-known in the art.

All publications and patents referred to herein are specifically incorporated by reference in their entirety.

EXAMPLES

Example 1

Peptides and Peptide Conjugates

Peptides were synthesized using automated solid phase peptide synthesis as described, e.g., in Stewart et al. (1984) *Solid Phase Peptide Synthesis*, Pierce Chemical Company, Rockford, Ill. Peptides were synthesized using a polyamide-Kieselguhr composite resin and a Milligen 9050 peptide synthesizer (Milligen/Biosearch, Burlington, Mass.). Coupling cycles were performed according to the manufacturer's recommendations. 9-Fluorenyl-methyloxy-carbonyl (Fmoc) amino acid was activated as a pentafluorophenyl ester (—OPfp ester); Peptides were deblocked using; (1) 20% piperidine in N,N-dimethylformamide (DMF) for alpha-amino groups; Peptides were cleaved from the resin and deprotected using 95% trifluoroacetic acid (TFA), (2) Reagent R [TFA (90%), thioanisol (5%), ethylene dithiole (3%) and anisole (2%)], Reagent B [TFA (88%), phenol (5%), triisopropylsilane (2%) and water (5%)] or Reagent T [TFA (95%), triisopropylsilane (5%); Deprotection agent being chosen as is understood in the art based on the protecting groups used and the type of amino acid residues in the peptide; Crude peptides were precipitated and washed with ether. Peptides were purified by high pressure liquid chromatography on a Vydac C-18 reverse-phase column using a Waters HPLC system. The mobile phase consisted of a gradient from 0.01% TFA in 95% water/acetonitrile to 0.01% TFA in 25% water/acetonitrile. Peptides were characterized by HPLC, amino acid analysis and mass spectrometry (ES or MALDI-TOF). Exemplary peptide sequences useful in this invention are listed in Tables 1–3.

It was found that certain peptides that were only partially deblocked, i.e., at least one amino acid protecting group had not been removed, showed significant enhancement of transfection. Appropriate choice of deprotection agent allows selective synthesis of peptides which retain a desired protecting group. For example, deprotection with Reagent T does not remove the Mtr protecting group on arginines allowing the synthesis of partially deblocked peptides with Mtr groups remaining on R residues.

Synthesis of Polyamine Conjugated Peptides

Peptides can be modified with polyamines, such as spermine, using an automated peptide synthesizer. Either the Fmoc or Boc chemistries can be used. For example, spermine can be attached to the N-terminus of a peptide as illustrated in Scheme I. 5-Carboxy spermine and Boc-protected 5-carboxy spermine can be synthesized as described in Behr, J-P. et al. (1989) Proc. Natl. Acad. Sci., 86:6982–6986. Fmoc-carboxy spermine can be synthesized by treating carboxy spermine with 9-fluorenylmethyl chloroformate. Fmoc-carboxy spermine or the pentafluorophenyl ester can be used in the synthesizer to obtain spermine-modified peptides. More than one polyamine can be attached in this manner to a given peptide using an appropriate combination of protecting groups.

N′,N″,N‴,N^IV-tetra(9-fluorenylmethoxycarbonyl)-5-carboxyspermine (Fmoc-carboxyspermine)

5-Carboxy spermine (11.0 g) was dissolved in 100 ml water. The solution was chilled on ice and diluted with 200 ml dioxane and flushed with argon. A solution of 50 g of 9-fluorenylmethyl chloroformate (Fmoc-Cl) in 200 ml of dioxane was slowly added to the chilled carboxy spermine. The reaction mixture was stirred under argon at 4° C. for an hour and at room temperature overnight under argon. The reaction was monitored by TLC (silica Gel, $CHCl_3$/MeOH::9/1). The reaction mixture was poured into 1.5 L ice cold water (1.5 L) and extracted with ethyl acetate (2 L). The organic layer was separated and sequentially extracted with 400 ml of 1 N HCl (2×) and 300 ml saturated NaCl. The organic layer was dried over $Na_2SO_4$ and concentrated on a rotary evaporator. The resultant gummy material was subjected to flash chromatography (silica, $CHCl_3$/MeOH::95/5) to yield 25.5 g of the desired material as a white fluffy solid.

high vacuum overnight. The ester was obtained in quantitative yield as a slightly yellowish gum, which was used without further purification in the peptide synthesizer.

Synthesis of Spermine-Modified Peptides

Spermine-modified peptides were synthesized using Fmoc chemistry on a Milligen 9050 synthesizer using the protocol suggested by the manufacturer. Peptides were synthesized conventionally and carboxyspermine was attached at the N-terminus of the synthesized peptide using Fmoc-carboxyspermine-OPfp ester as the last amino acid to be added on the synthesizer, as illustrated in Scheme 1. Deprotection reagents used were selected as discussed above. The peptide-spermine conjugates were stored frozen until use. Table 4 lists several examples of spermine-conjugated peptides that were synthesized using FMOC-carboxy-spermine. Modified peptides were analyzed and purified using HPLC on a Vydac C-18 column. Modified peptides were characterized by HPLC, amino acid analysis and mass spectrom-

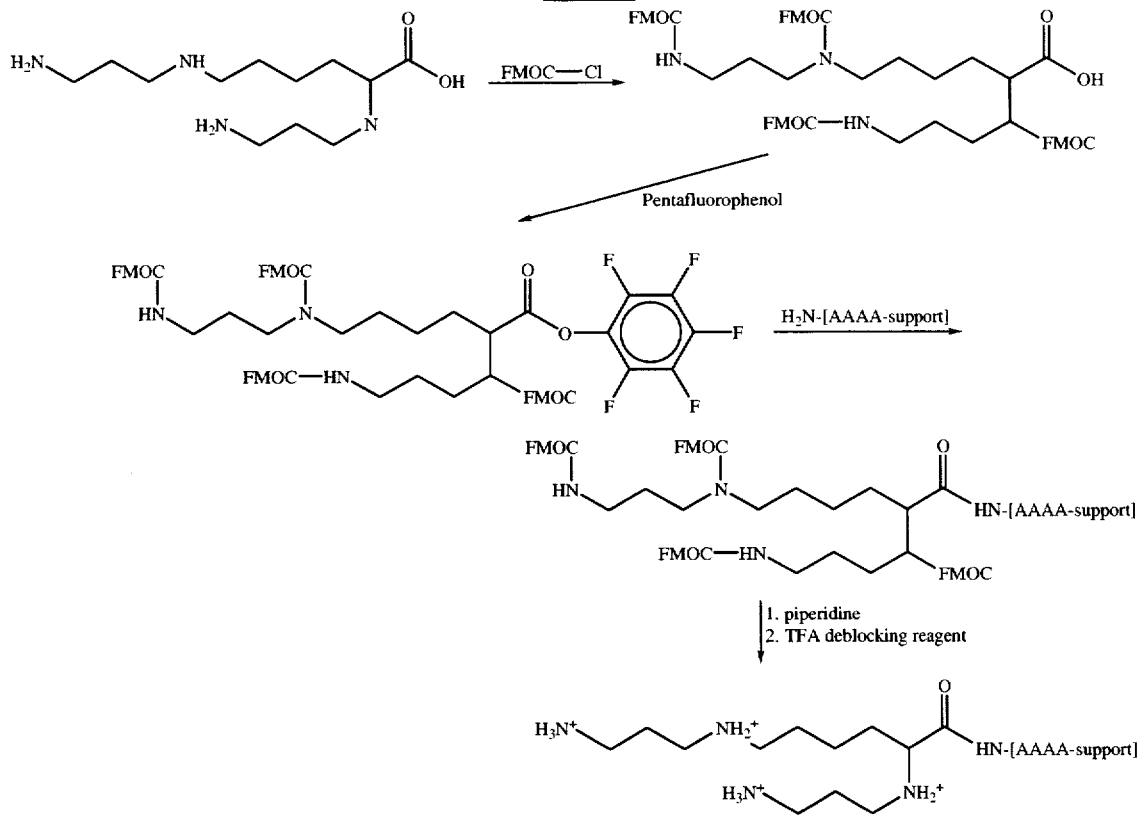

SCHEME 1

Fmoc-carboxy-spermine-OPfp ester

A solution of pentafluorophenol (4.2 g) in 3 ml of dioxane solution, followed by 2 ml of dioxane, was added to a solution of Fmoc-carboxy-spermine (8.0 g) in 10 ml of dioxane. The resulting mixture was chilled in an ice water bath and flushed with argon. Freshly distilled dicyclohexylcarbodiimide (DCC, 1.6 g) in 4 ml of dioxane was added to the chilled reaction mixture. The mixture was stirred at 4° C. for about an hour and at room temperature overnight under argon. Precipitated dicyclohexyl urea (DCU) was filtered out of the reaction mixture, which was then concentrated to dryness on a rotary evaporator. The residue was dried under etry (ES or MALDI-TOF). This method can be employed or readily adapted in view of well-known techniques for synthesis of polyamine-peptide conjugates.

Peptide-spermine conjugates can also be prepared using a heterobifunctional cross-linking agent sulfo-SMPB (Pierce Chemical Co., Rockford, Ill.) as illustrated in Scheme II. See: S. S. Wong "Heterobifunctional Cross-linkers" in *Chemistry of Protein Conjugation and Cross-linking* CRC Press p.147–194. Briefly, 100 mg/mL sulfo-SMPB in DMF is diluted to 20 mg/mL using 50 mM sodium phosphate buffer (pH 7.5). Spermine (50 mg/mL in 50 mM sodium phosphate buffer) was then added to the sulfo-SMPB solution at a 3:1 molar ratio. After 1 hour at room temperature, the reaction mixture is fractionated (LH-20 column) using the sodium phosphate buffer. The first major peak (spermine-MPB) was collected. Spermine-MPB is mixed at a 1:1.5 to 1:2 ratio with a synthetic (or naturally-occurring) peptide with terminal cysteine (HS-), either in pure powder form or in acetonitrile/water solution. Excess peptide is separated on a LH-20 column eluted with water. The peptide-spermine conjugate is stored frozen until use. The reaction of spermine-MPB with HS-peptide should be performed under appropriate reducing conditions to avoid peptide dimer formation. This method can be employed or readily adapted in view of well-known techniques for synthesis of polyamine -peptide conjugates.

Peptide dimers of peptides containing cysteine residues can be formed, if desired, by oxidative coupling to form a disulfide bond between two peptides. Concatemers and Mixed concatemers of this invention can be prepared by automated peptide synthesis and if desired the concatemers, mixed concatemers and peptide oligomers (dimers, etc.) can be conjugated to nucleic acid-binding groups by methods described herein.

Scheme 3 illustrates appropriately protected polyamine species that can be used in automated peptide synthesizers to introduce polyamines at the carboxy terminus of peptides (e.g., Structure II, for carboxyspermine conjugation). The scheme illustrates a synthesis of the carboxyspermine derivative of Structure II, which can be readily generalized for the synthesis of any analogous polyamine derivatives. The compound of Structure II, activated by removal of the pentafluorophenol group, can be conjugated to the solid support to provide a carboxy spermine group at a peptide carboxy terminus. Standard automated peptide synthesis is performed using the support of Structure I. The fully protected carboxy spermine of Structure II can itself be employed as a reagent for addition of the carboxy spermine group at any position along a synthetic peptide chain. These methods can be readily and routinely adapted for conjugation of any polyamine.

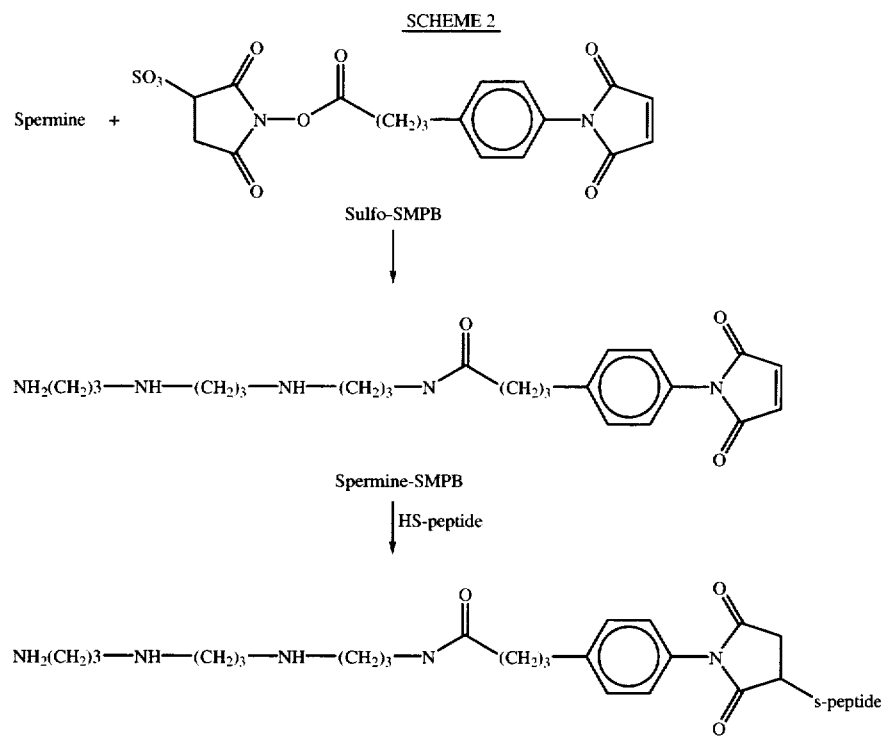

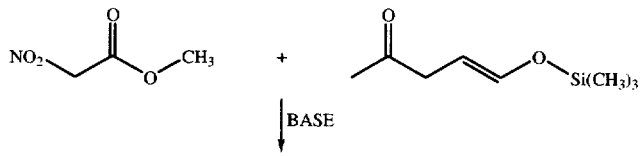

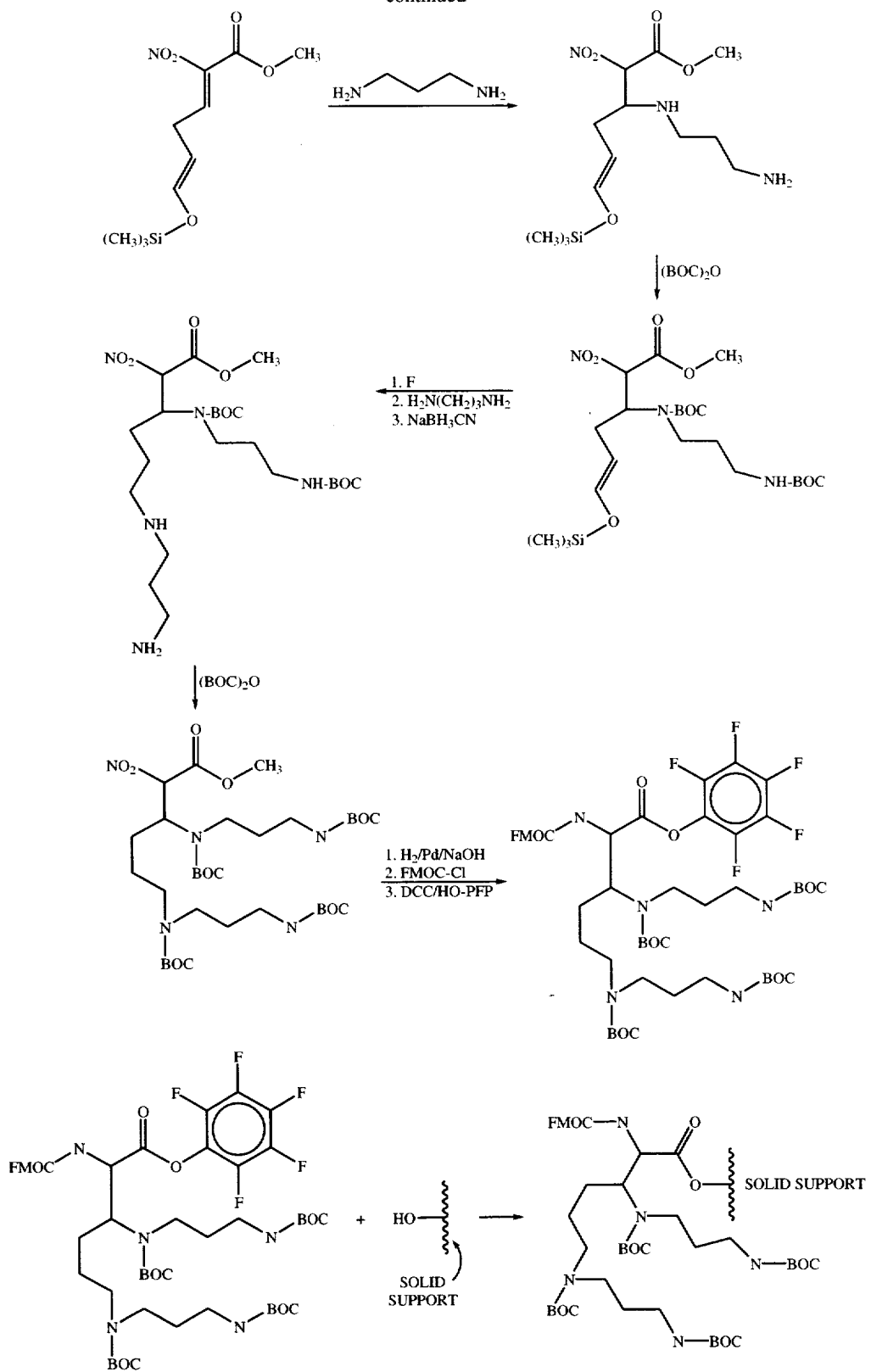

Peptide-Lipid Conjugates

Peptide-lipid conjugates are prepared as follows: A lipid with a reactive head group, for example a group such as 1,2-dioleoyl-S,N-glycero-3-phosphoethanolamine-N-[3-(2-pyridyldithio)propionate] (N—PDP—PE, Avanti Polar Lipids, Inc. Alabaster, Ala.) is reacted with a cysteine-peptide (e.g., cysteine at either end of the functional peptide). Reaction can be performed at RT and followed by measuring the released chromophore. See Scheme 4. For example, N—PDP—PE is dissolved in methanol to a concentration of 0.2 M (about 200 mg/mL). Cys-peptides, including VSVG-Cys, (e.g., KFTIVFC, SEQ ID NO: 11); RGD-Cys (e.g., GRGDSPC, SEQ ID NO: 8); or Cys-NLS (e.g., CGWGPKKKRKVG, SEQ ID NO: 12), are dissolved in an appropriate solvent, e.g., DMF, to a concentration of 100 mg/mL and mixed with the N—PDP—PE solution at a molar ratio of 1.5–2:1. Peptide-lipid conjugates can be purified by HPLC using a Vydac protein and peptide C18 reverse phase column with an acetonitrile/water/TFA and methanol solvent system. The conjugate can be characterized by UV and MS analysis.

SCHEME 4:

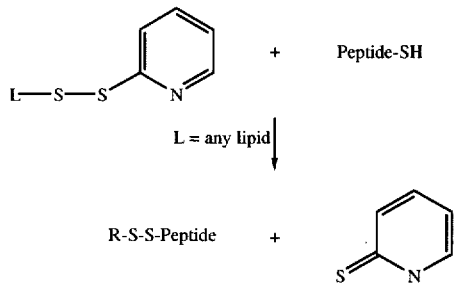

Example 2

Enhancement of Cationic Lipid Transfection of Human Fibroblast Cells with Viral Peptides Added into Transfection Medium The following viral peptides were synthesized using automated solid phase peptide synthesis as described in Example 1: the membrane fusion region of influenza virus (HApep) (see, Epand et al. (1992) Biopolymers 32:309); modifications of FluHa to yield hemagglutinin peptides E5 and K5 (see, Kamata, H. et al. (1994) Nucleic Acids Res. 22:536–537); and vesicular stomatitis virus G-protein, VSVG (see, Schlegel, R. and Wade, M. (1985) J. Virol. 53:319). The nuclear localization signal (NLS) of SV40 large T antigen, NLS (see, Lanford et al. (1986) Cell 46:575) and the RGD peptide (Ruoslahti, E. and Pierschbacher, D. (1987) Science 238:491) were also synthesized, but not included in this experiment. The sequences of the peptides synthesized is given in Table 5.

Newborn human fibroblasts (NHF) were isolated from neonatal foreskin dermis and prepared as described in Hawley-Nelson, P., et al. (1993) Focus 15:73, incorporated by reference herein, and cultured for up to 20 passages. Cultures of adherent cells were grown in Dulbecco's-modified Eagle's medium (DMEM) containing 0.1 mM MEM Non-Essential Amino Acids (NEAA), 10% (v/v) fetal bovine serum (FBS), 100 U/mL penicillin (PEN) and 100 µg/mL streptomycin (STREP). Cultures were passaged at confluence using 0.25% (v/v) trypsin, 0.1 mM EDTA.

The plasmid vectors pCMVβgal and pCMVSPORTβgal are commercially available (Clontech, CA and GIBCO-BRL, respectively) mammalian reporter vectors containing the E. coli β-galactosidase (β-gal) gene under the control of the Cytomegalovirus promoter. See: MacGregor et al. (1989) Nucleic Acids Res. 17: 2365; Norton et al. (1985) Mol. and Cell Biol. 5:281; Alam (1990) Anal. Biochem. 188:245. Plasmid DNA was purified by standard cesium chloride methods.

Human fibroblasts were plated the day before transfection at $8 \times 10^4$ per well on a 24-well dish. Before transfection, the cells were rinsed with serum-free DMEM. Two 25 µl aliquots of "OPTI-MEM"-I medium, one containing 3 µg "LIPOFECTAMINE" and the other containing 0.2 µg pCMVβgal DNA, were combined to form complexes for 30 min at room temperature. "LIPOFECTAMINE" (Gibco/BRL: Life Technologies, Inc., Gaithersburg, Md.) is a 3:1 (w/w) mixture of the polycationic lipid, 2,3-dioleyloxy-N-[2(sperminecarboxamido)ethyl]-N,N-dimethyl-1-propanaminium trifluoroacetate (DOSPA), and DOPE. Peptides were dissolved in dimethylsulfoxide (DMSO) at 250× the final concentration (see Table 5). Peptide solution (1 µL) was added to 250 µl serum-free DMEM transfection medium and added to the rinsed cells. Treatments containing the E5, K5, HApep, and VSVG alone, and E5+K5 and VSVG+K5 in combination with each other were compared to a transfection sample containing no peptide ("LIPOFECTAMINE"+DNA only). For treatments that combined two peptides, E5, K5 and VSVG were all used at 5 µM concentrations. The DNA-lipid aggregates in "OPTI-MEM"-I were then added to the transfection medium with added peptide(s) on the cells. After 24 hours incubation at 37° C., cells were harvested, extracted and assayed for β-galactosidase activity as described above.

Enzyme activity of lysed cell extracts was used to compare levels of expression resulting from different treatment protocols. One to two days following transfection, cells were rinsed once with PBS and frozen at −70° C. in 0.15 mL/well 0.1% "TRITON" X-100 (t-octylphenoxypolyethoxyethanol; Sigma Chemical Co., St. Louis, Mo.; "TRITON" is a trademark of Union Carbide, Inc.) and 0.1M Tris, pH 8.0. After rapid thawing at 37° C., the lysate was cleared by centrifugation. Lysed cell extracts were assayed for β-galactosidase activity employing the method essentially as described in Sambrook et al. (1989) Molecular Cloning A Laboratory Manual, $2^{nd}$ Ed., Cold Spring Harbor Laboratory Press, p. 16.66. Briefly, soluble cell extract containing 2–6 µg protein was added to 100 µl 0.1M sodium phosphate buffer (pH 7.5) containing 1 mM $MgCl_2$, 50 mM β-mercaptoethanol and 0.88 mg/mL o-nitrophenyl-β-D-galacatopyranoside (ONPG) in a 96-well microtiter plate. A standard curve of 10–70 ng β-galactosidase (Gibco/BRL: Life Technologies, Inc., Gaithersburg, Md.) was included on the plate. Yellow color developed in 5–20 minutes at 37° C. The reaction was stopped when necessary by adding 150 µl 1 M $Na_3CO_2$; $OD_{420}$ was determined on a microtiter plate reader.

FIG. 1 shows the effect of peptides added into the DMEM transfection medium after lipid has been complexed to DNA. As shown in FIG. 1, relatively minor enhancements of transfection compared to the control were observed, except for HApep and the combination of VSVG and E5. The VSVG+E5 combination showed greater than 2-fold enhancement compared to "LIPOFECTAMINE" alone. Peptide concentrations that resulted in optimal transfection are listed in Table 5. It was later found that the order of addition of components had a significant effect upon transfection enhancement by peptides. Initial complexation of the peptide with the nucleic acid prior to contact of the DNA with the cationic lipid composition in general gave significantly higher transfection enhancement.

Example 3

Transfection Enhancement of Sp-NLSNLS Pre-complexed to DNA in Combination with "LIPOFECTAMINE"

Sp-NLSNLS the peptide (NLSNLS): GGYGP-KKKRKVGGGGYGPKKKRKVGG [SEQ ID NO 13] conjugated to spermine enhances transfection efficiency in combination with "LIPOFECTAMINE" in human fibroblasts, NIH 3T3, MDCK and BHK-21 cells when the peptide is pre-complexed to the DNA prior to addition of "LIPOFECTAMINE."

In this example, all media, sera, and reagents were from GIBCO BRL unless otherwise noted. All cells were cultured in Dulbecco's MEM (DMEM, high glucose: 4,500 mg/L D-glucose, with L-glutamine and phenol red) with 0.1 mM Non-Essential Amino Acids (NEAA), 100 U/mL penicillin and 100 μg/mL streptomycin. Human fibroblasts, MDCK, and BHK-21 cells were cultured with 10% Fetal Bovine Serum (FBS). NIH 3T3 cells were cultured with 10% Calf Serum. Human fibroblast cells were obtained as described in Example 2. NIH 3T3 (NIH Swiss mouse embryo, contact-inhibited fibroblasts), MDCK (dog kidney cells) and baby hamster kidney (BHK-21) cells were obtained from the American Type Culture Collection (Rockville, Md.). All cultures were maintained at 37° C. with 5% $CO_2$. Human fibroblasts at $6 \times 10^4$, BHK-21 at $4 \times 10^4$, MDCK at $6 \times 10^4$, and NIH 3T3 at $5 \times 10^4$ cells per well were plated the day before transfection in 24-well plates. On transfection day, the cell cultures were 50–80% confluent.

For each well on a 24-well plate, 0.5–4 μL "LIPOFECTAMINE" Reagent and 0.1–0.8 μlgr pCMV.SPORT-β-gal or pCMVβ DNA (G. R. McGregor and C. T. Caskey (1989) Nucleic Acids Res. 17:2365) were diluted into separate 25 μL aliquots of serum-free medium ("OPTIMEM-I" or D-MEM with added 0.1 mM NEAA). Sp-NLSNLS (1–4 μg, as a 1 mg/ml solution in water) was added into the DNA solution, and incubated at RT for 15 min to allow pre-complexation. The DNA-Sp-NLSNLS solution was mixed together with diluted "LIPOFECTAMINE", then incubated at RT for 30 min. The cells were rinsed with serum-free DMEM with NEAA, then 0.2 ml per well of serum-free DMEM with NEAA was added to the cells. The DNA-Sp-NLSNLS-lipid complex was added to the serum-free D-MEM on the cells, incubated at 37° C. for 5 hrs, then 1 ml of D-MEM containing FBS (final concentration 10%) was added. Cultures were incubated 24 hrs, then fixed and stained in-situ with X-gal (J. R. Sanes et al. (1986) EMBO J. 5:3133 see below) or harvested for ONPG assay (as described in Example 2).

Figure 2:
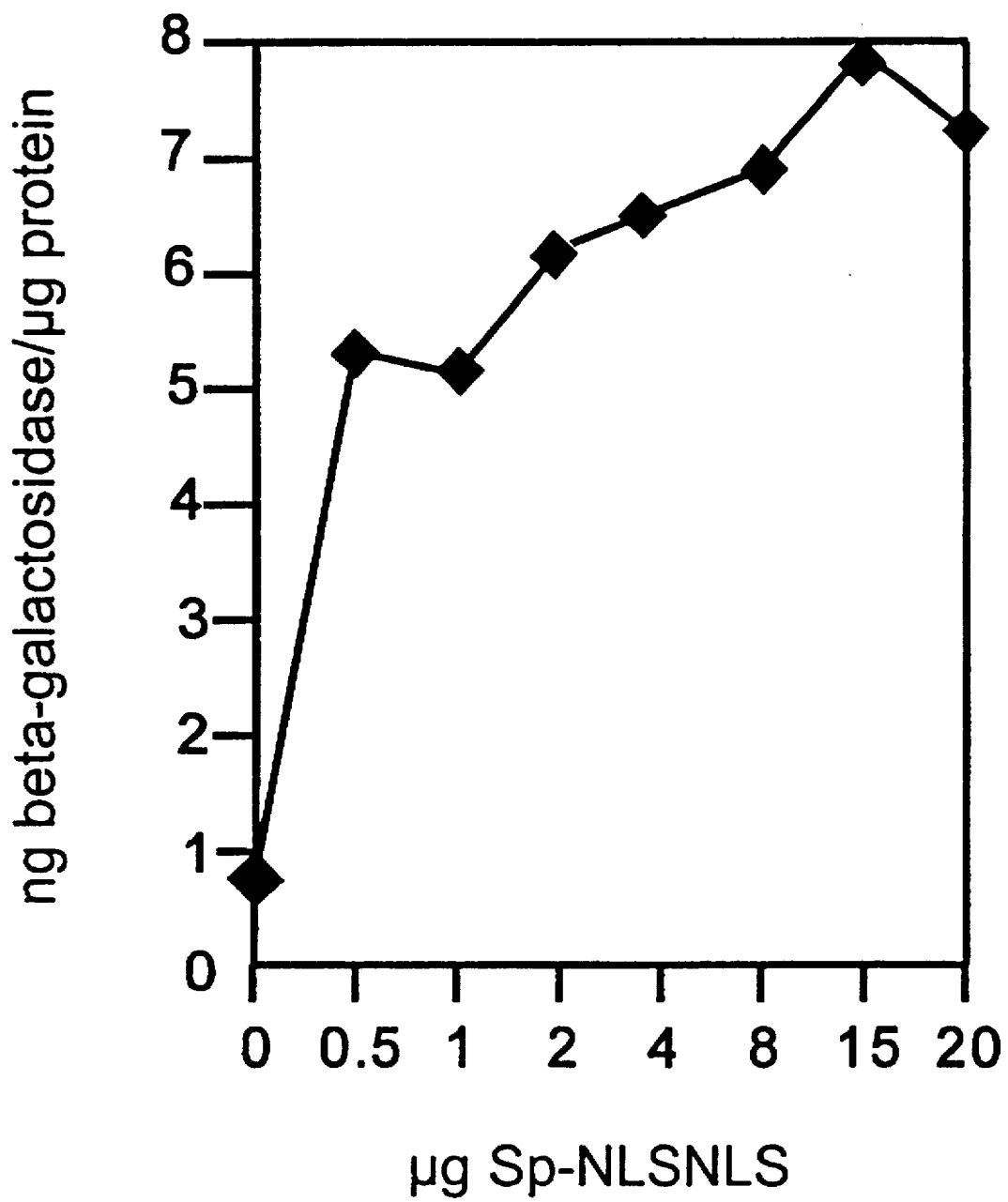
FIG. 2 is a graph showing the effect of Sp-NLSNLS concentration on enhancement of "LIPOFECTAMINE" transfection activity. Human fibroblasts were transfected with 0.4 µg DNA, 2 µL "LIPOFECTAMINE" and Sp-NLSNLS as indicated in serum-free medium. Cells were harvested and assayed for β-galactosidase activity 24 h after transfection.

In order to test enhancement of transfection efficiency, human fibroblasts were transfected with pCMV.SPORT-β-gal DNA using "LIPOFECTAMINE" and Sp-NLSNLS. Increasing concentrations of Sp-NLSNLS were tested and β-galactosidase activity was assayed with ONPG (FIG. 2). In this transfection, 2–20 μg Sp-NLSNLS precomplexed with 0.4 μg DNA resulted in a plateau of enhanced activity. Enhancement levels between 5–8-fold were routinely observed at 2–4 μg Sp-NLSNLS per 0.4 μg DNA in similar experiments (data not shown).

Human fibroblasts similarly transfected were stained in-situ with X-gal. The results of the most active concentration of Sp-NLSNLS (2 μg) and lipid (2 μL) with DNA (0.4 μg) was photographed and positive cells counted. Percent positive cells (mean of 3 determinations +/− half the range) was determined: "LIPOFECTAMINE" (4+/−2%), "LIPOFECTAMINE" with Sp-NLSNLS (18+/−6%). This is a four-fold enhancement in percent transfected cells.

In situ staining was used to demonstrate β-galactosidase expression. Cells were rinsed with PBS, fixed for 5 min in 2% (v/v) formaldehyde, 0.2% glutaraldehyde in PBS, rinsed twice with PBS, and stained overnight with 0.1% X-gal (Gibco/BRL: Life Technologies, Inc., Gaithersburg, Md.), 5 mM potassium ferrocyanide, 5 mM potassium ferricyanide, 2 mM $MgCl_2$ in PBS. Rinsed cells were photographed using a 10× objective on a Nikon inverted microscope with Hoffman optics. Transfection efficiency was evaluated by counting or estimating the number of β-gal positive (blue-stained) cells.

Analyses of transfection enhancement by Sp-NLSNLS were performed in human fibroblasts, BHK-21, NIH3T3, and MDCK cells using wide ranges of lipid and DNA concentrations. The data are presented in FIGS. 3A–3H. In each case, the whole platform of activity is raised, not just the activity at the optimum of lipid and DNA concentrations. Enhancement of this type facilitates the reproducibility of high efficiency transfections, broadening the spectrum of activity of polycation lipid-mediated transfection (particularly transfection using "LIPOFECTAMINE" and resulting in high activity over a broader range of DNA and lipid concentrations. The use of spermine-derivatized peptides, such as Sp-NLSNLS, in transfections decreases the amount of detailed optimization of lipid and DNA concentration previously required to achieve high activity cationic lipid transfections in a given system.

By increasing the platform of activity across the ranges of lipid and DNA concentrations with Sp-NLSNLS and other peptides and spermine-derivatized peptides, it is possible to achieve high level transfections with lower amounts of lipid and DNA resulting in higher cell yield from equivalent or higher efficiency transfection.

Figure 3A:
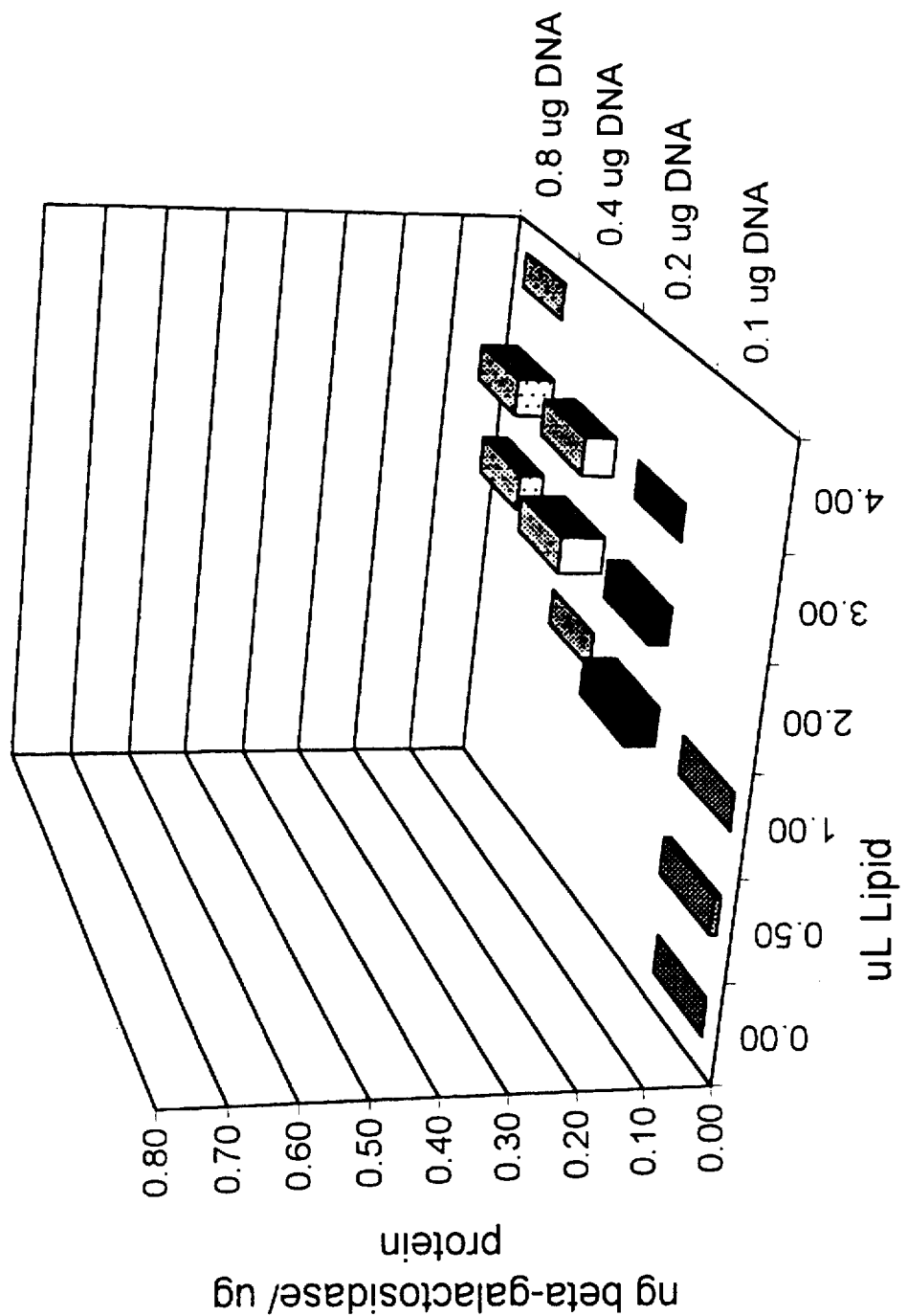
FIGS. 3A–H provide comparisons of lipid transfection with and without Sp-NLSNLS precomplexed with DNA in 4 cell types. Human fibroblast (3A and 3B); BHK-1(3C and 3D); NIH 3T3 (3E and 3F); MDCK (3G and 3H) cells were transfected in 24-well plates with "LIPOFECTAMINE" and DNA as shown.
Figure 3B:
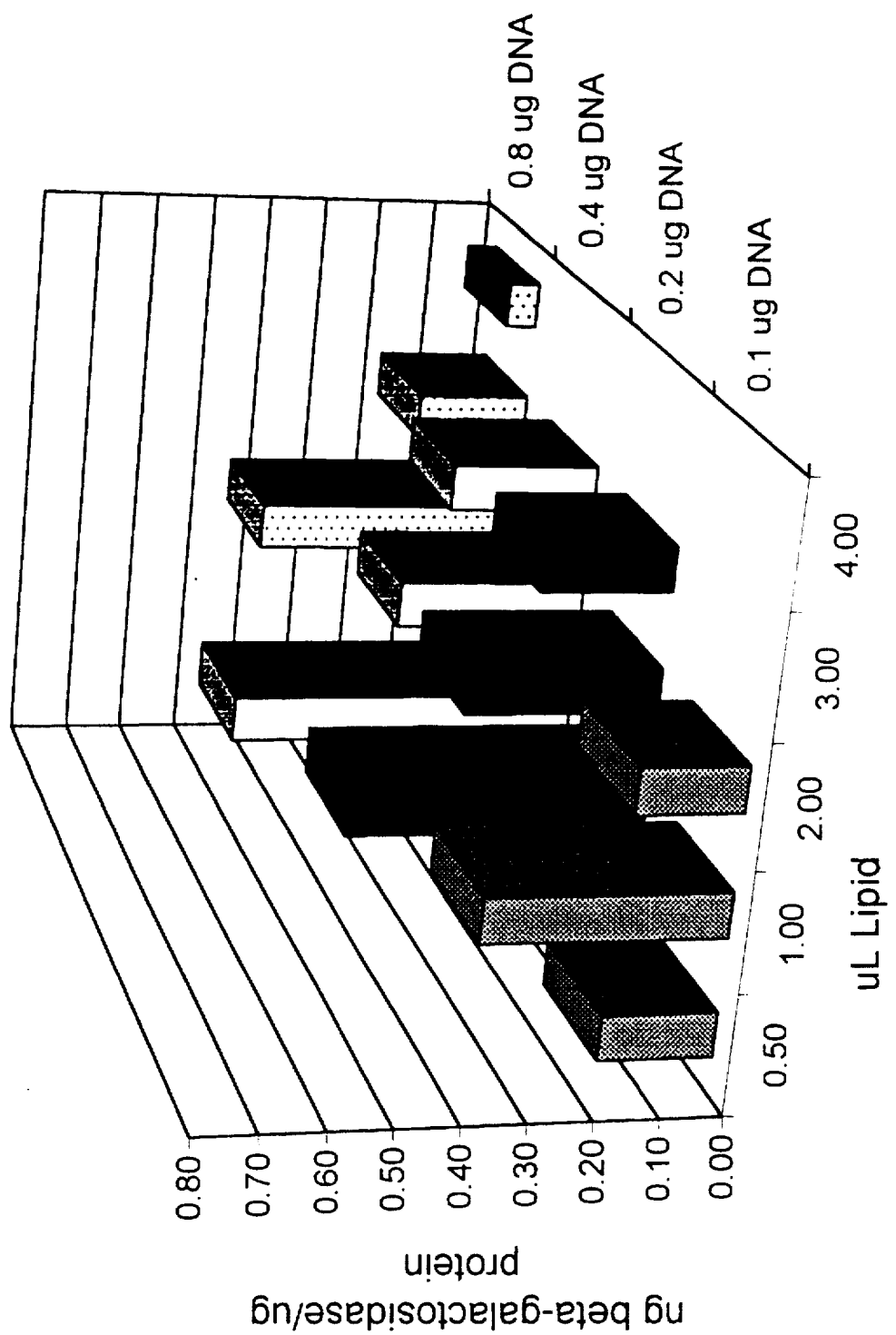
Figure 3C:
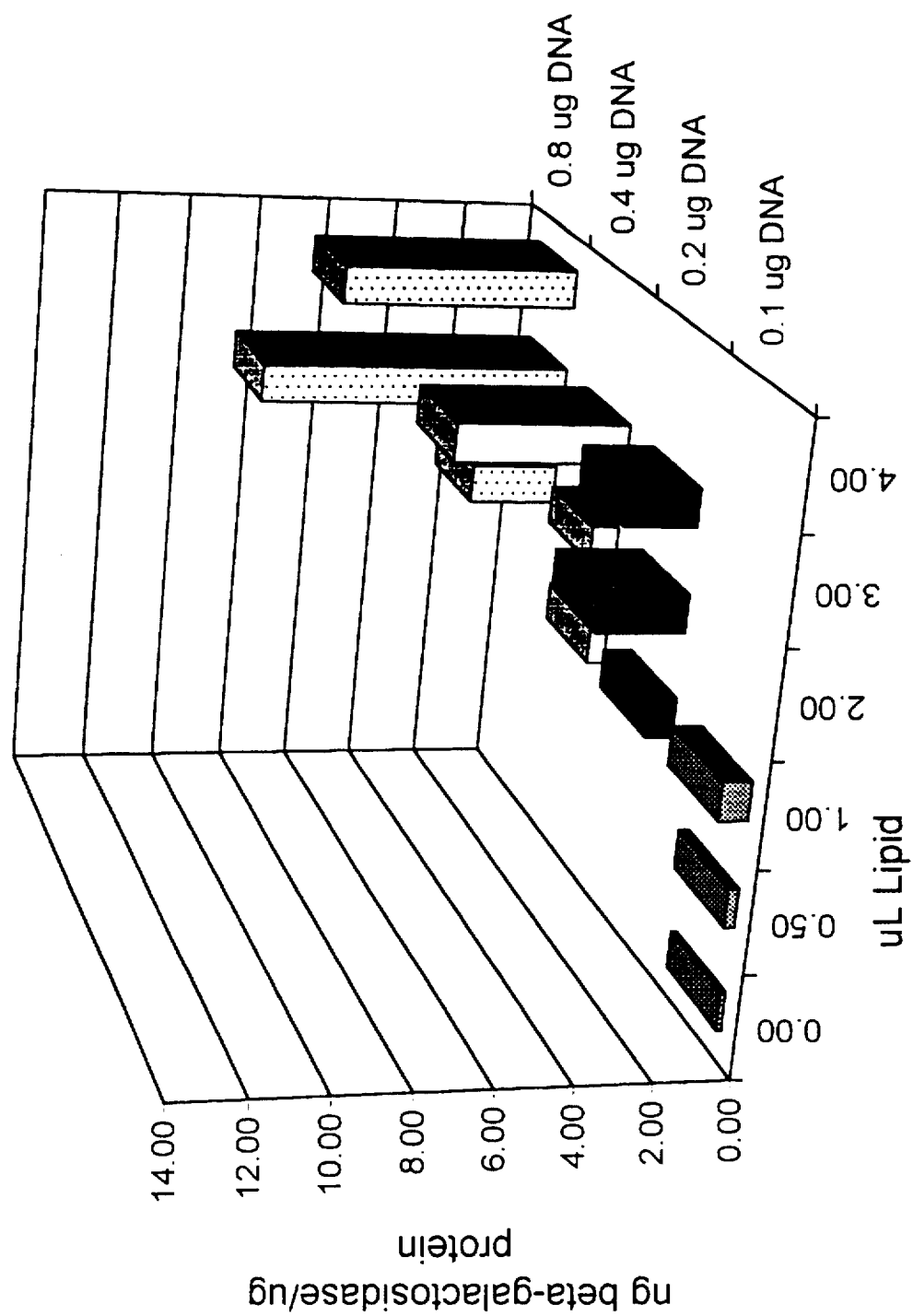
Figure 3D:
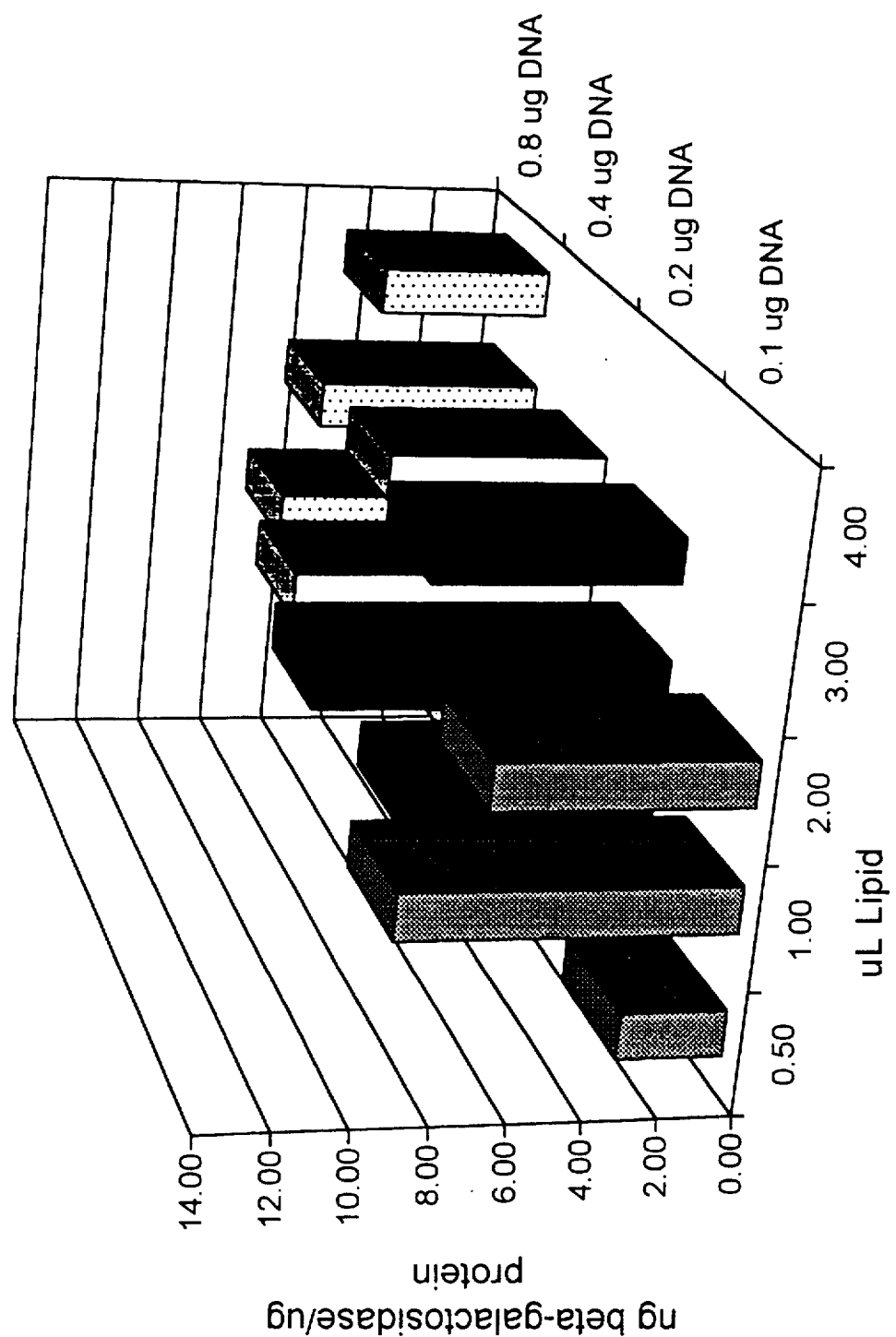
Figure 3E:
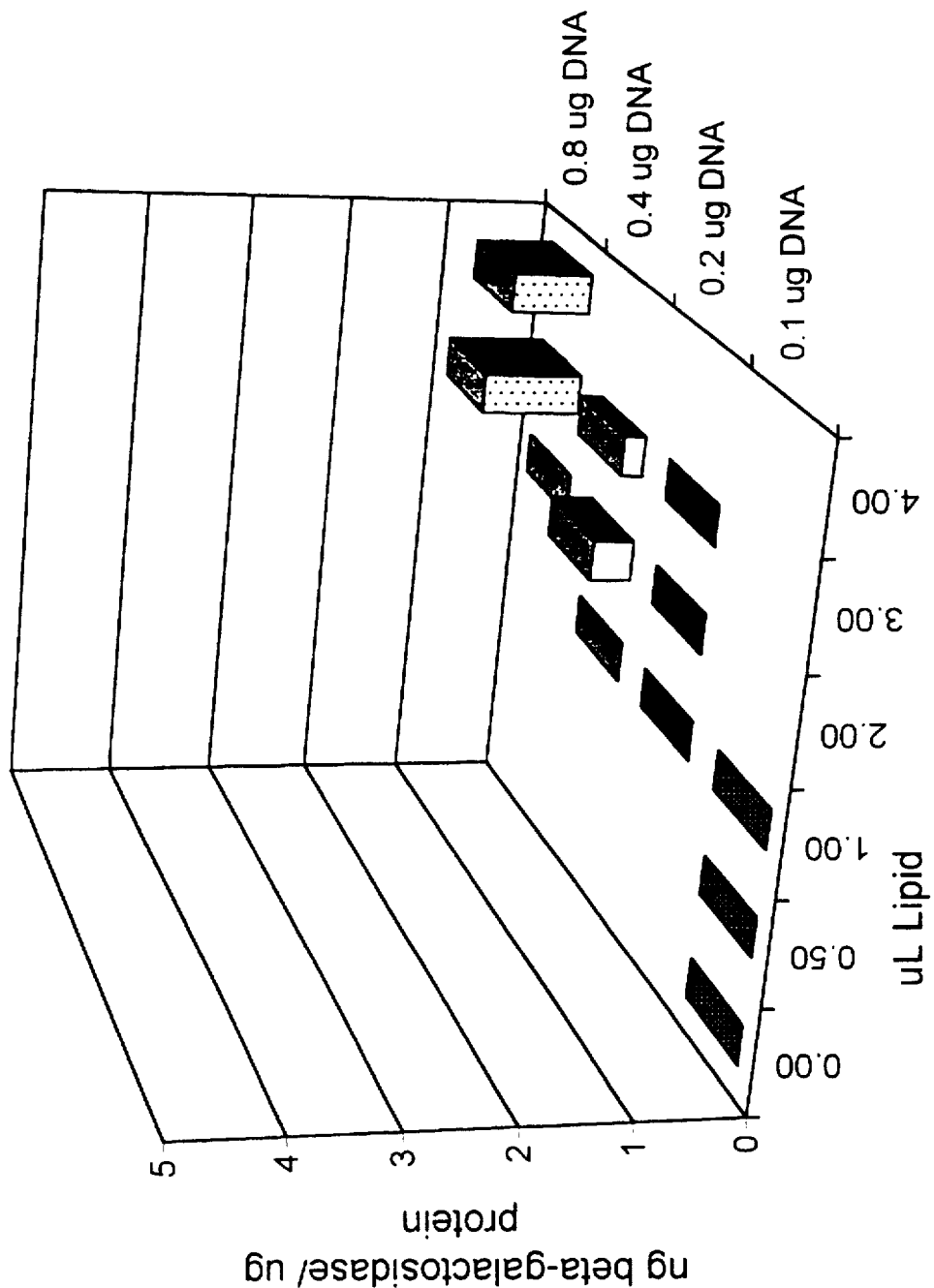
Figure 3F:
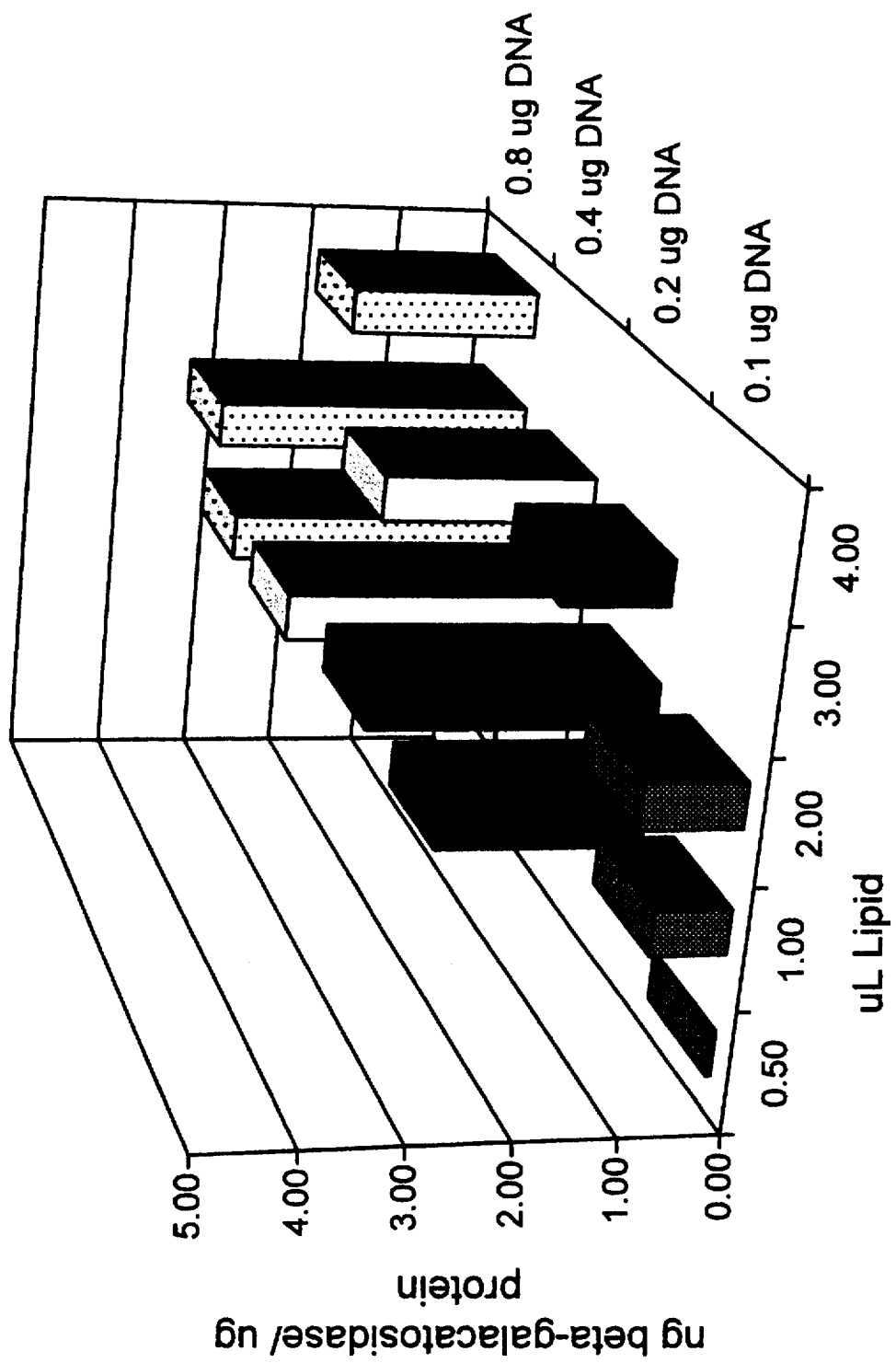
Figure 3G:
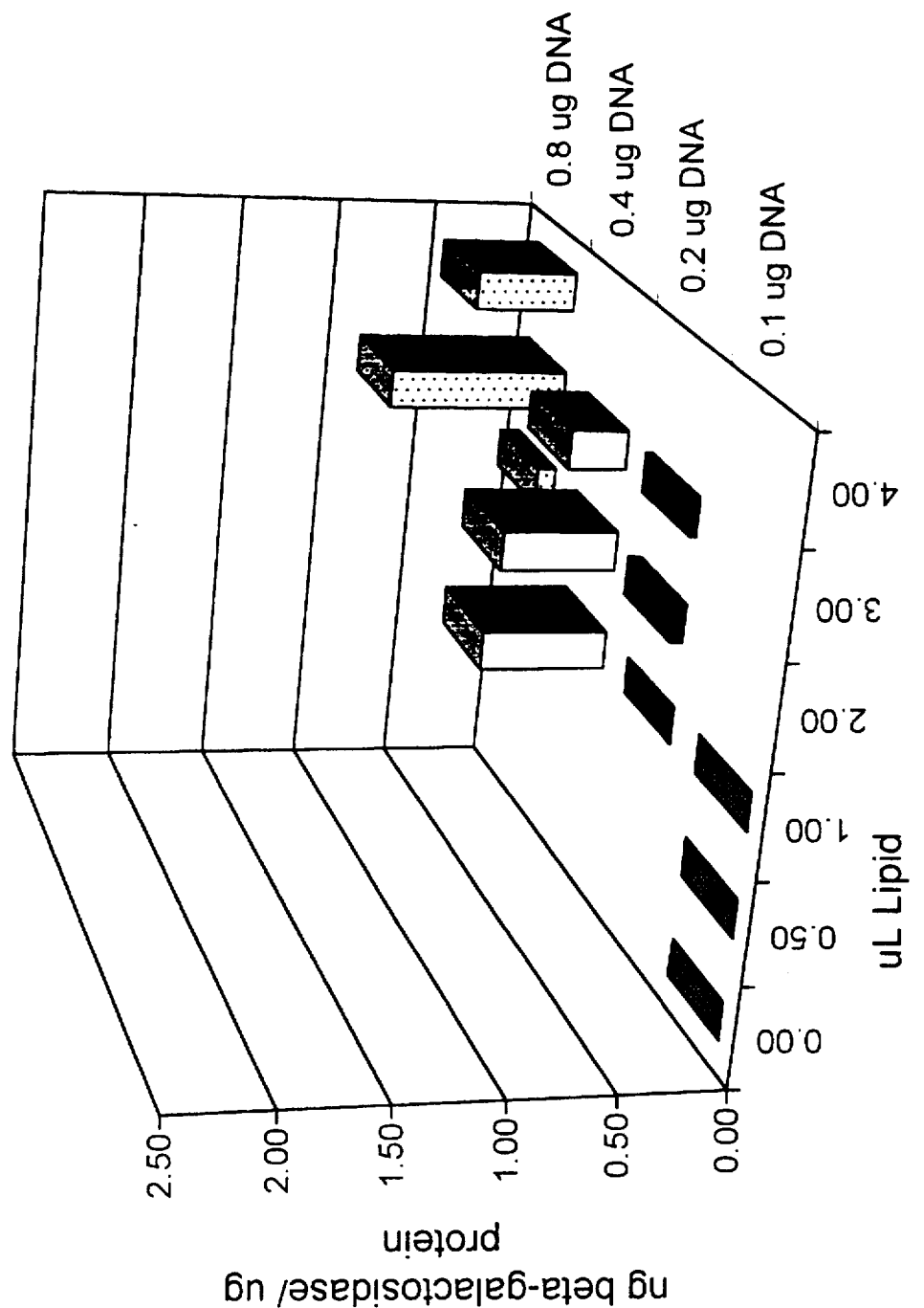
Figure 3H:
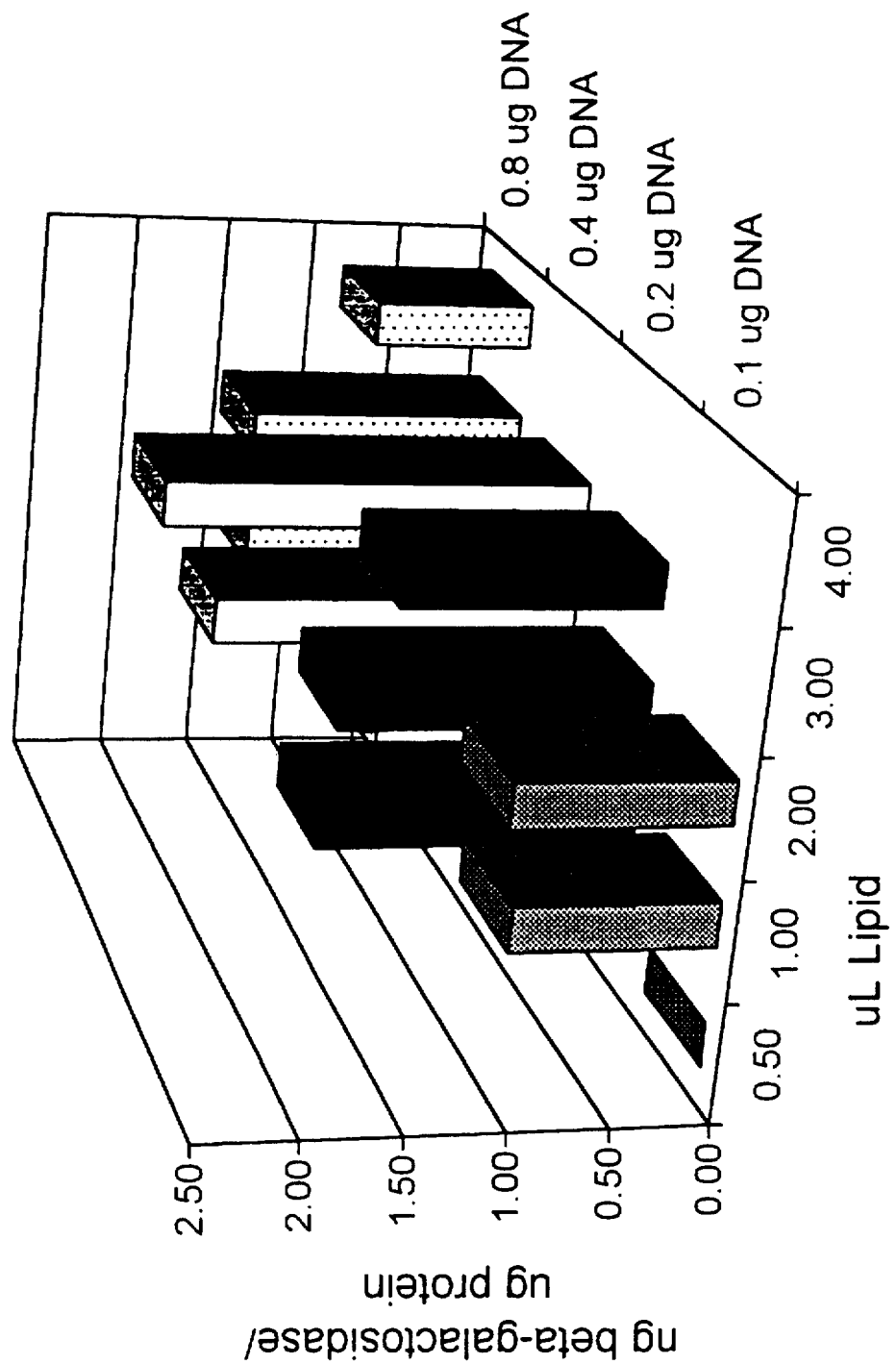

Table 6 illustrates this observation using data generated in the experiment graphed in FIGS. 3A and 3B. Peak activity of 0.07 ng β-gal/μg protein is achieved with "LIPOFECTAMINE" alone at 0.4 μg DNA and 2 μL "LIPOFECTAMINE". The protein yield (which is directly proportional to cell yield) for these conditions was 67.5 μg/well. By using Sp-NLSNLS 0.38 ng β-gal activity per μg protein (over 5-fold higher than the peak for LIPOFECTAMINE alone) can be achieved in a transfection with 0.1 μg DNA and 1 μl "LIPOFECTAMINE.". The protein yield under these conditions is 85.5 μg/well, 25% more than at the peak with "LIPOFECTAMINE" alone. This difference is seen in other cell types, as well (data not shown). The enhanced yield is most likely due to the use of lower lipid and DNA concentrations, since similar yields are seen with "LIPOFECTAMINE" alone and with Sp-NLSNLS-precomplexed DNA at the same lipid and DNA concentrations (data not shown).

Sp-NLSNLS was tested for enhancement of transfection with two other cationic lipid transfection reagents: "LIPOFECTIN" (1:1 (w/w) mixture of DOTMA:DOPE) and "CELLFECTIN" (1:1.5 (w/w) mixture of TM-TPS (N, N', N'', N'''-tetramethyl-N, N', N'', N'''-tetrapalmitylspermine) :DOPE). No enhancement was observed with either of these reagents (data not shown).

Example 4

Enhancement of "LIPOFECTAMINE" Transfection in Human Fibroblast Cells by Peptides and Peptide Derivatives Pre-Complexed to DNA Table 7 compares transfection activity for "LIPOFECTAMINE" combined with various peptides and peptide derivatives. Transfections were done in human fibroblasts (except as indicated) using pCMSPORTβgal or pCMVβ using the ONPG assay as described in Example 3. Experiments were done in 24-well plates using 0.4 μg DNA/transfection (except as indicated), the protocol described in Example 3 was used with the peptides added to DNA initially. The data in Table 7 are the fold-enhancement at peak activity for "LIPOFECTAMINE" and the peptide or modified peptide. During the purification of the peptides by HPLC in several instances, two peaks were isolated. K16NLS (peak 2) is incompletely deprotected material which is believed to retain the Mtr-protecting group on an arginine residue (R). Most preferred transfection enhancing agents are those peptides or peptide derivatives that give the highest fold enhancement (compared to cationic lipid alone) at the lowest amount of enhancing agent. Note that the reverse NLS peptide exhibited no enhancement of transfection with "LIPOFECTAMINE".

Example 5

Transfection Activity of DMRIE-C in the Presence of Certain Peptide Derivatives Table 8 compares transfection activity for DMRIE-C combined with several different peptide (or peptide derivatives or combinations thereof) for transfection of suspension cell lines (K562 and Jurkat cells).

DMRIE-C is a 1:1 (M/M) liposome formulation with cation lipid DMRIE (1,2-dimyristyloxypropyl-1-3-dimethylhydroxyethyl ammonium bromide) and cholesterol in membrane-filtered water. See: K. Schifferli and V. Ciccarone (1996) "FOCUS" 18:45 and V. Ciccarone et al. (1995) "FOCUS" 17:84. Transfections were performed using pCMVSPORTCAT, and the assays were performed using CAT assay: varying amounts of peptide derivatives (or mixtures of such derivatives) were combined and pre-incubated with DNA for 15 minutes. The precomplexed DNA-peptide (and or peptide derivative) complex was then mixed with 1.6 μL DMRIE-C. The transfection composition was then mixed with $4 \times 10^5$ cells/well in 24-well plates. CAT assays were performed at 36–48 h after transfection.

The chloramphenicol acetyltransferase (CAT) assay was preformed as described in J. R. Neuman et al. (1987) BioTechniques 5:444. Briefly, harvested cells from a well were washed with PBS and pelleted by centrifugation at 1000 rpm (~600×G) for 5 m at RT for suspension cells. Pellets were put on ice and 1 mL of 0.1 M Tris—HCl (pH 8.0) containing 0.1% TRITON X-100 was added and then frozen at −70° C. for 2 h. Pellets are thawed at 37° C., then chilled on ice. Cell lysates were centrifuged at maximum speed in a microcentifuge for 5 min. Supernatant was collected and heated for 10 m at 65° C. to inactivate deacetylases and other inhibitors of the CAT reaction. Heated supernatants (hereafter cell extracts) were centrifuged at maximum speed for 3 m and stored at −70° C.

For each cell extract sample, add 5–150 μL cell extract and make up to 150 μL with 0.1 M Tris—HCl (pH 8.0). Negative control is 150 μL 0.1 M Tris—HCl (pH 8.0); Positive control is CAT standard solution (1, 5, 10, 20, and 50 mU of CAT) made up to 150 μL with 0.1 M Tris—HCl (pH 8.0). Add 100 μL of a mixture: 10 μL 1 M Tris—HCl (pH 8.0); 1 μL 250 mM chloramphenicol (in 100% ethanol); 5 μL (50 nCi) [$^{14}$C-butryl Coenzyme A (0.010 μCi/μL); 84 μL deionized, distilled water, to each sample and incubate at 37° C. for 2 h. Add 3 mL of "ECONOFLUOR" to each sample and incubate at RT for 2 h. Count each sample for 0.5 m in a liquid scintillation counter.

Table 8 lists the highest fold enhancement observed with peptide used and the amount of peptide (or derivative) needed to achieve that level of enhancement.

Example 6

Enhancement of Dendrimer-Mediated Transfection

Starburst polyamidoamine (PAMAM) dendrimers: G7 (EDA), G9 (EDA), and G6 (EDA) modified with lysine [Lys DMER] or with arginine [Arg DMER], and a "COMB BURST" (Trademark, Dendritech Inc.) dendrigraft were obtained from Michigan Molecular Institute. The PAMAM dendrimers were prepared by now standard methods as described, for example, in Tomalia D. A. and Durst, H. D. (1993) in Weber E. (ed.) Topics in Current Chemistry, 165: "Supramolecular Chemistry I-Directed Synthesis and Molecular Recognition, Springer-Verlag, Berlin pp. 193–313 and Tomalia D. A. et al. (1990) Angew. Chem. Intl. Ed. Engl. 29:138–175. These modified dendrimers were stored as the trifluoroacetate salts. Lys DMER has a charge density of $2.07 \times 10^{15}$+charge/μg; Arg DMER has a charge density of $2.41 \times 10^{15}$+charge/μg. "COMB BURST" dendrigraft was grown to generation three and then modified with one layer of PAMAM repeat units to give a polymer with a molecular weight of 30,000, a polydispersity of 1.11 and a charge density of $2.68 \times 10^{15}$+charges/μg.

The effect of peptides and spermine-peptide conjugates on dendrimer-mediated transfection was assessed in transfections of COS-7 cells (ATCC). Dendrimer transfection was performed essentially as described in Kukowska-Latallo J. F. et al. (1996) Proc. Natl. Acad. Sci. USA 93::4897–4902. COS-7 cells were plated at $4 \times 10^4$ cells/well in 24 well plates. Two DNA plasmids were used: pCMVβ for X-gal staining and pGL3 (Promega) for luciferase assay both at 0.5 μg/well. All dendrimers were used at 3 μg/well and chloroquine was added to all dendrimer transfections at 25 μg/mL. Dendrimer transfections were compared with "LIPOFECTAMINE" transfections using 1 μL/well. The effect of three peptides: K16NLS (peak 2, incompletely deblocked) added at 1 μg/well, Sp-NLSNLS added at 1.5 μg/well, and NLS added at 20 μg/well was determined.

For the luciferase assay, each well was extracted in 0.15 ml lysis buffer (25 mM Tris HCl, pH 8.0, 0.1 mM EDTA, 10% glycerol, 0.1% Triton X 100), and 10 μL centrifuged extract supernate from each well was automatically mixed with 50 μL Luciferase Assay Reagent (Promega) and assayed in a luminometer for 5 seconds. The X-gal assay was performed as in Example 3.

The results of the luciferase assay are listed in Table 9. The transfection activity of each of the dendrimers in Table 11 was enhanced by the three peptides or peptide conjugates tested. The most active dendrimers for transfection of COS-7 cells were Arg DMER and "COMB BURST". In these experiments, transfection was not optimized for dendrimer concentration or the amount of peptide added. X-gal assays were consistent with the data given in Table 9.

Example 7

Effect of Sp-NLSNLS on Stable Transformation Frequency in NIH 3T3 Cells

Figure 4A:
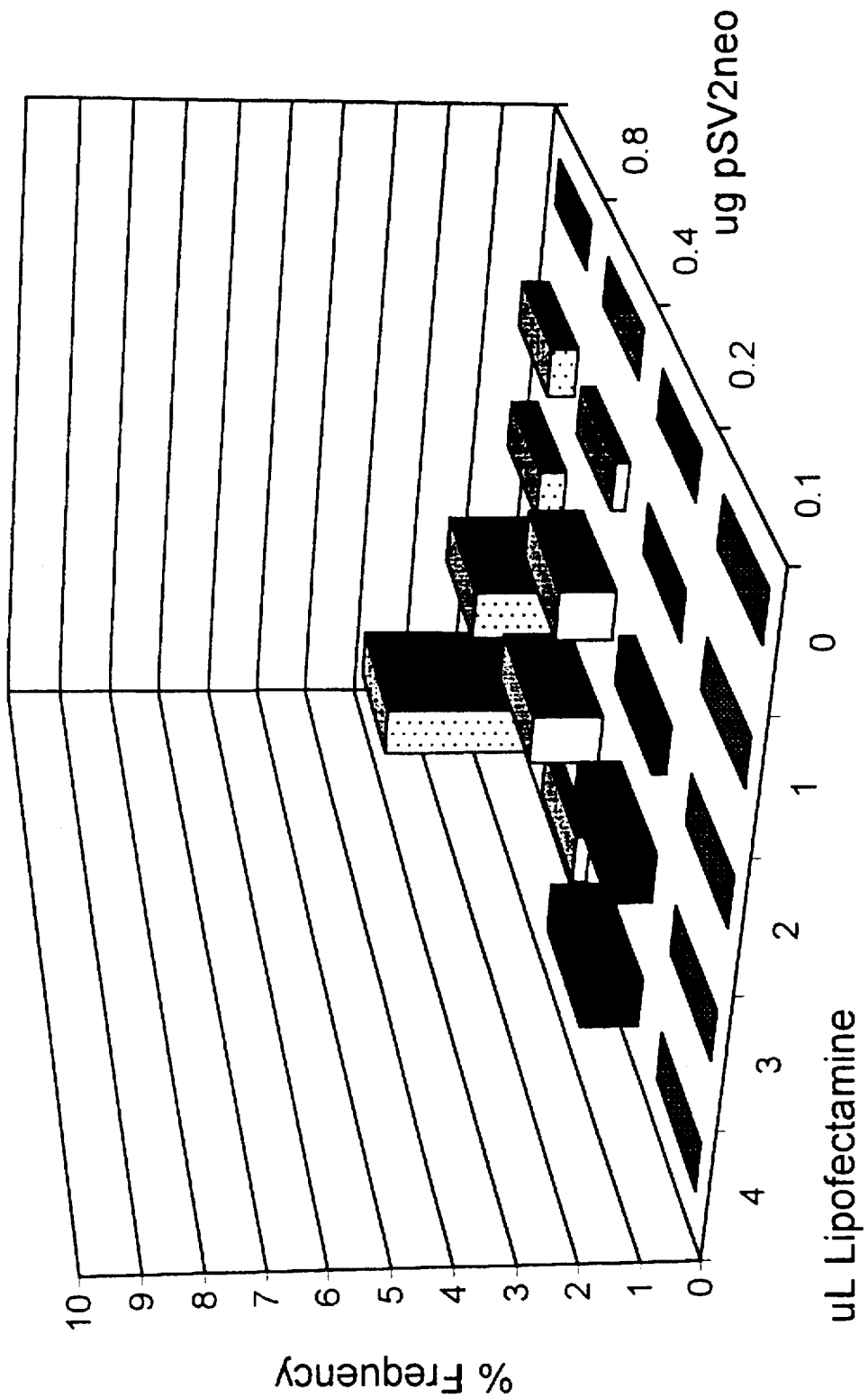
FIGS. 4A and 4B are three-dimensional graphs comparing "LIPOFECTAMINE" transfection in the presence of varying amounts of Sp-NLSNLS with varying amounts of DNA (pSVneo) with transfection without peptide. The transfections were performed in NIH 3T3 cells.
Figure 4B:
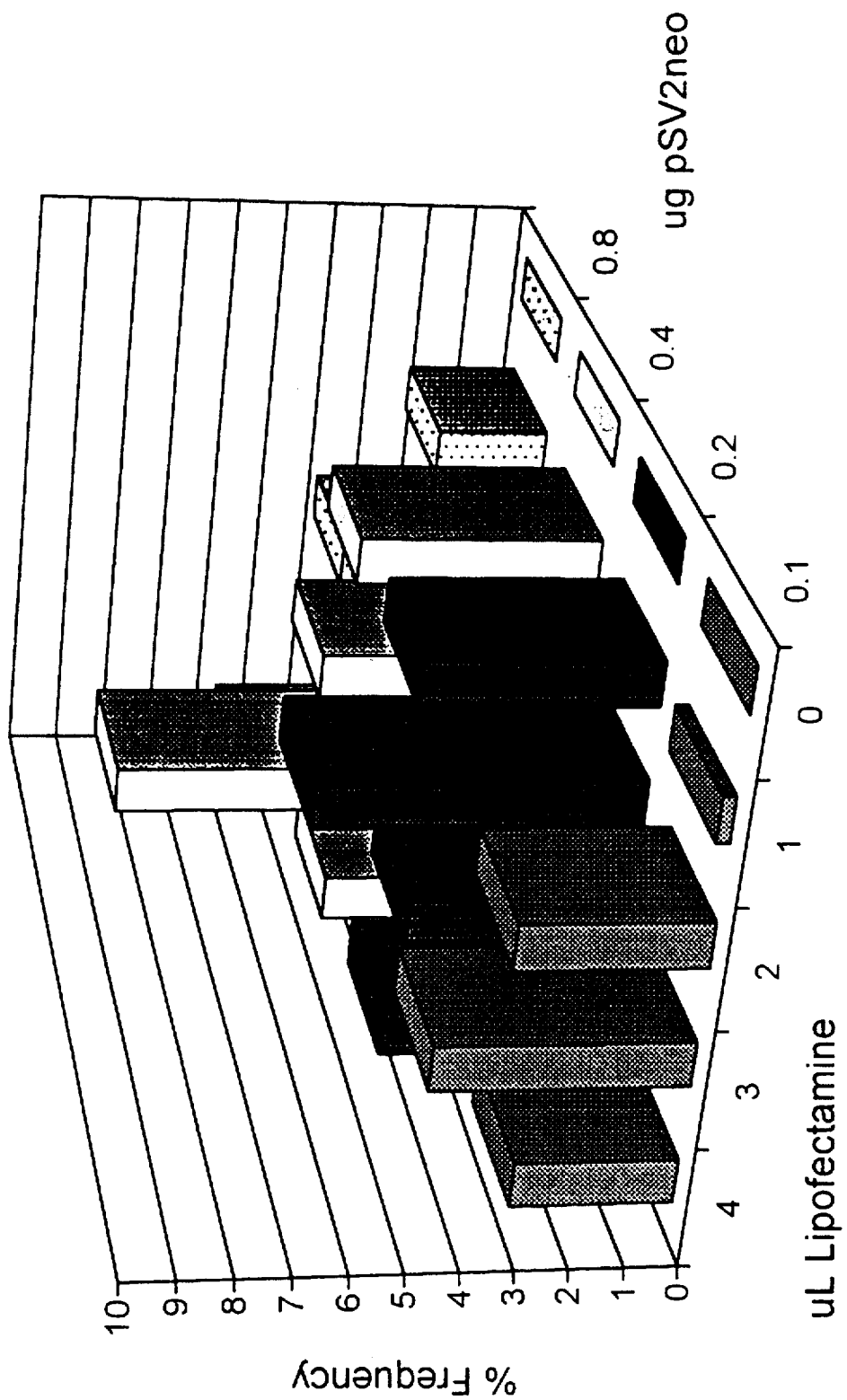

NIH 3T3 cells were seeded at $6 \times 10^4$ cells/well in 24 well plates, in DMEM supplemented with 10% Calf Serum, and allowed to grow overnight. Cells were transfected in matrix format using 0, 1, 2, 3, and 4 μL "LIPOFECTAMINE", and 0.1, 0.2, 0.4, and 0.8 μg pSV2neo (obtained from ATCC, carrying a neomycin resistance gene, see: Berg et al. (1982) J. Mol. Appl. Genet. 1: 327–341. Cells were pre-incubated with 2 μg (for 0.1–0.4 μg DNA) or 4 μg (for 0.8 μg DNA). Control cells were provided with no peptide (here Sp-NLSNLS, see Table 5 for sequence). At 24 h after transfection, cells were split 1:150 into 35 mm plates containing growth medium, and allowed to grow overnight. The next day cells were put in selection medium containing 0.6 mg/ml "GENETICIN" (G418 sulfate, Gibco/BRL: Life Technologies, Inc., Gaithersburg, Md.)). After 10 days plates were fixed and stained with 10% formalin/PBS containing 0.4% toluidine blue. G418-resistant colonies were counted and expressed as % of initial number of cells plated. FIGS. 4A (no peptide control) and 4B (with added Sp-NLSNLS) show the results of this experiment. Significant enhancement of transfection by SP-NLSNLS is observed in almost all cases.

TABLE 1

Examples of Cell Adhesion Proteins

| LIGAND | BINDING REGION | REFERENCE |
|---|---|---|
| Fibronectin | RGD cell binding region (RGDSPC)(SEQ ID NO: 14) (all motifs) | Pierschbacher & Ruoslahti (1987) J. Biol. Chem. 262, 17294–17298 |
| Fibronectin 1 | including all cell binding regions RGD cell binding region (all motifs) | Pierschbacher & Ruoslahti (1984) Nature 309, 30–33 |
| Fibronectin 2 | RGD cell binding region (REDV [SEQ ID NO. 15]/RGDV 8 SEQ ID NO. 16]) | Humphries et al., (1986) J. Cell Biol. 103, 2637–2647 |
| Fibronectin 3 | CS1 Fragment [SEQ ID NO: 17][1] | Humphries et al., (1987) J. Biol. (Chem. 262, 6886–6892 |
| Vitronectin | RGD cell binding region (RGDV [SEQ ID NO: 16]) | Suzuki et al., (1985) EMBO J. 4, 2519–2524 |
| Laminin 3 | RGD cell binding region (RGDN [SEQ ID NO: 18]) | Grant et al., (1989) Cell 58, 933–943 |
| Tenascin 1 | RGD cell binding region (RGDM [SEQ ID NO: 19]) | Friedlander et al., (1988) J. Cell Biol. 107, 2329–2340 |
| Collagen 1 | RGD cell binding region (RGDT [SEQ ID NO: 20]) | Dedhar et al., (1988) J. Cell Biol. 104, 585–593 |
| Collagen 6 | RGD cell binding region (RGDX [SEQ ID NO: 21]*) | Aumailley et al., (1989) Cell Res. 181, 463–474 |
| von Willebrand Factor | RGD cell binding region (RGDS [SEQ ID NO: 22]) | Haverstick et al, (1985) Blood 66, 946–952 |
| Fibrinogen 1 | RGD cell binding region (RGDS [SEQ ID NO:22]) | Gardner and Hynes et al., (1985) Cell 42, 439–448 |
| Thrombo-spondin 1 | RGD cell binding region (RGDA [SEQ ID NO:23]) | Lawler et al., (1988) J. Cell Biol. 107, 2351–2361 |

[1]CS1 peptide sequence: DELPQLVTLPHPNLHGPEILDVPST

*X = various amino acids.

TABLE 2

Exemplary Peptides For Enhancement of Transfection[1]

| | | |
|---|---|---|
| NLS-BASED | PKKKRKV | [SEQ ID NO 2] |
| | (±C)G(Y or W or -)GPKKKRKVGG | [SEQ ID NO:24] |
| | C(±Y or W)PKKKRKVGG | [SEQ ID NO:26] |
| | (±C)G(±Y or W)GPKKKRKVGG(±G$_n$) | [SEQ ID NO:24] |
| | (Xaa)$_x$PKKKRKV(Zaa)$_z$ | [SEQ ID NO:26] |
| | (Xaa)$_x$(±Y or W)PKKKRKV(Zaa)$_z$ | [SEQ ID NO:26] |
| | (Xaa)$_x$(±Y or W)(Jaa)$_j$PKKKRKV(Zaa)$_z$ | [SEQ ID NO:26] |
| | (Xaa)$_x$PKKKRKV(±Y or W)(Zaa)$_z$ | [SEQ ID NO:25] |
| | (Xaa)$_x$(±C)(±Y or W)(Jaa)$_j$PKKKRKV(±C)(Zaa)$_z$ | [SEQ ID NO:26] |
| | (Xaa)$_x$(±C)(±Y or W)(Jaa)$_j$PKKKRKV(±C)(Zaa)$_z$(Uaa or Sp or Poly)$_u$ | [SEQ ID NO:26] |
| | (±C)(Xaa)$_x$(±Y or W)(Jaa)$_j$PKKKRKV(Zaa)$_z$(±C) | [SEQ ID NO:27] |
| | (±C)(Xaa)$_x$(±Y or W)(Jaa)$_j$PKKKRKV(±C)(Zaa)$_z$(Uaa or Sp or Poly)$_u$ | [SEQ ID NO:28] |
| | Uaa or Sp or Poly)$_u$(Xaa)$_x$(±C)(±Y or W)(Jaa)$_j$PKKKRKV(Zaa)$_z$(±C) | [SEQ ID NO:29] |
| | (Uaa or Sp or Poly)$_u$(Xaa)$_x$(±C)(±Y or W)(Jaa)$_j$PKKKRKV(±C)(Zaa)$_z$ | [SEQ ID NO:30] |
| NLS-CONCATEMERS | [(Xaa)$_x$(±C)(±Y or W)(Jaa)$_j$PKKKRKV(±C)(Zaa)$_z$]$_p$ | [SEQ ID NO:30] |
| | [(Xaa)$_x$(±C)(±Y or W)(Jaa)$_j$PKKKRKV(±C)(Zaa)$_z$]$_p$(Uaa or Sp or Poly)$_J$ | [SEQ ID NO:30] |
| | (Uaa or Sp or Poly)$_J$[(Xaa)$_x$(±C)(±Y or W)(Jaa)$_j$PKKKRKV(±C)(Zaa)$_z$]$_p$ | [SEQ ID NO:31] |
| RGD(SP) | RGDSP | [SEQ ID NO:32] |
| | (±C)RGDSP(±C) | [SEQ ID NO:32] |
| | (±C)(±G)RGDSP(±C) | [SEQ ID NO:32] |
| | (Xaa)$_x$RGDSP(Zaa)$_z$ | [SEQ ID NO:32] |
| | (Xaa)$_x$(±C)(±G)RGDSP(±G)(±C)(Zaa)$_z$ | [SEQ ID NO:32] |
| | (±C)(Xaa)$_x$(±G)RGDSP(±G)(Zaa)$_z$(±C) | [SEQ ID NO:32] |
| | (Xaa)$_x$RGDSPC(Zaa)$_z$ | [SEQ ID NO:32] |
| | (Uaa or Sp or Poly)$_u$(Xaa)$_x$RGDSP(Zaa)$_z$ | [SEQ ID NO:32] |
| | (Uaa or Sp or Poly)$_u$(Xaa)$_x$(±C)(±G)RGDSP(±G)(±C)(Zaa)$_z$ | [SEQ ID NO:32] |
| | (Xaa)$_x$(±C)(±G)RGDSP(±G)(±C)(Zaa)$_z$(Uaa or Sp or Poly)$_u$ | [SEQ ID NO:33] |
| | (Uaa or Sp or Poly)$_u$(Xaa)$_x$(±C)(±G)RGDSP(±G)(Zaa)$_z$(±C) | [SEQ ID NO:34] |
| | (±C)(Xaa)$_x$(±G)RGDSP(±G)(±C)(Zaa)$_z$(Uaa or Sp or Poly)$_u$ | [SEQ ID NO:35] |
| | (Xaa)$_x$RGDSP(Zaa)$_z$(Uaa or Sp or Poly)$_u$ | [SEQ ID NO:35] |
| RGD(MF) | RGDMF | [SEQ ID NO:36] |
| | (±C)GRGDMF(±C) | [SEQ ID NO:37] |
| | GRGDMFC | [SEQ ID NO:37] |
| | (±C)(±G)RGDMF(±G)(±C) | [SEQ ID NO:37] |
| | (Xaa)$_x$RGDMF(Zaa)$_z$ | [SEQ ID NO:37] |
| | (Xaa)$_x$(±C)(±G)RGDMF(±G)(±C)(Zaa)$_z$ | [SEQ ID NO:37] |
| | (±C)(Xaa)$_x$RGDMF(Zaa)$_z$(±C) | [SEQ ID NO:38] |

TABLE 2-continued

Exemplary Peptides For Enhancement of Transfection[1]

| | | |
|---|---|---|
| | (Xaa)$_x$(±C)RGDMF(±C)(Zaa)$_z$ | [SEQ ID NO:37] |
| | (Uaa or Sp or Poly)$_u$(Xaa)$_x$(±C)(±G)RGDMF(±G)(Zaa)$_z$(±C) | [SEQ ID NO:39] |
| | (±C)(Xaa)$_x$(±G)RGDMF(±G)(±C)(Zaa)$_z$(Uaa or Sp or Poly)$_u$ | [SEQ ID NO:40] |
| | (Uaa or Sp or Poly)$_u$(Xaa)$_x$(±C)(±G)RGDMF(±G)(±C)(Zaa)$_z$ | [SEQ ID NO:41] |
| | (Xaa)$_x$(±C)(±G)RGDMF(±G)(±C)(Zaa)$_z$(Uaa or Sp or Poly)$_u$ | [SEQ ID NO:42] |
| CS-1 | DELPQLVTLPHPNLHGPEILDVPST | [SEQ ID NO:17] |
| Peptide | (±C)DELPQLVTLPHPNLHGPEILDVPST(±C) | [SEQ ID NO:43] |
| | (Xaa)$_x$DELPQLVTLPHPNLHGPEILDVPST(Zaa)$_z$ | [SEQ ID NO:43] |
| | (Xaa)$_x$(±C)DELPQLVTLPHPNLHGPEILDVPST(±C)(Zaa)$_z$ | [SEQ ID NO:45] |
| | (±C)(Xaa)$_x$DELPQLVTLPHPNLHGPEILDVPST(Zaa)$_z$(±C) | [SEQ ID NO:43] |
| | (Uaa or Sp or Poly)$_u$(Xaa)$_x$(±C)DELPQLVTLPHPNLHGPEILDVPST(Zaa)$_z$(±C) | [SEQ ID NO:44] |
| | (Uaa or Sp or Poly)$_u$(Xaa)$_x$(±C)DELPQLVTLPHPNLHGPEILDVPST(±C)(Zaa)$_z$ | [SEQ ID NO:45] |
| | (±C)(Xaa)$_x$DELPQLVTLPHPNLHGPEILDVPST(±C)(Zaa)$_z$(Uaa or Sp or Poly)$_u$ | [SEQ ID NO:46] |
| | (Xaa)$_x$(±C)DELPQLVTLPHPNLHGPEILDVPST(±C)(Zaa)$_z$(Uaa or Sp or Poly)$_u$ | [SEQ ID NO:45] |
| | (Xaa)$_x$DELPQLVTLPHPNLHGPEILDVPST(Zaa)$_z$(Uaa or Sp or Poly)$_u$ | [SEQ ID NO:47] |
| | (Uaa or Sp or Poly)$_u$(Xaa)$_x$DELPQLVTLPHPNLHGPEILDVPST(Zaa)$_z$ | [SEQ ID NO:44] |
| LDV(active | EILDVPST | [SEQ ID NO:48] |
| part of | (±C)EILDVPST(±C) | [SEQ ID NO:50] |
| CS-1 | (Xaa)$_x$EILDVPST(Zaa)$_z$ | [SEQ ID NO:50] |
| | (Xaa)$_x$(±C)EILDVPST(±C)(Zaa)$_z$ | [SEQ ID NO:50] |
| | (±C)(Xaa)$_x$EILDVPST(Zaa)$_z$(±C) | [SEQ ID NO:49] |
| | (Uaa or Sp or Poly)$_u$(Xaa)$_x$EILDVPST(Zaa)$_z$ | [SEQ ID NO:50] |
| | (Uaa or Sp or Poly)$_u$(Xaa)$_x$EILDVPST(±C)(Zaa)$_z$ | [SEQ ID NO:50] |
| | (Uaa or Sp or Poly)$_u$(Xaa)$_x$EILDVPST(Zaa)$_z$(±C) | [SEQ ID NO:51] |
| | (Xaa)$_x$EILDVPST(Zaa)$_z$(Uaa or Sp or Poly)$_u$ | [SEQ ID NO:52] |
| | (±C)(Xaa)$_x$EILDVPST(±C)(Zaa)$_z$(Uaa or Sp or Poly)$_u$ | [SEQ ID NO:52] |
| | (Xaa)$_x$(±C)EILDVPST(±C)(Zaa)$_z$(Uaa or Sp or Poly)$_u$ | [SEQ ID NO:53] |
| VSVG | KFTIVF | [SEQ ID NO:54] |
| 6mer | (±C)KFTIVF(±C) | [SEQ ID NO:56] |
| | (Xaa)$_x$KFTIVF(Zaa)$_z$ | [SEQ ID NO:56] |
| | (Xaa)$_x$(±C)KFTIVF(±C)(Zaa)$_z$ | [SEQ ID NO:56] |
| | (±C)(Xaa)$_x$KFTIVF(Zaa)$_z$(±C) | [SEQ ID NO:55] |
| | (Uaa or Sp or Poly)$_u$(Xaa)$_x$KFTIVF(Zaa)$_z$ | [SEQ ID NO:56] |
| | (Uaa or Sp or Poly)$_u$(Xaa)$_x$(±C)KFTIVF(±C)(Zaa)$_z$ | [SEQ ID NO:56] |
| | (Uaa or Sp or Poly)$_u$(Xaa)$_x$(±C)KFTIVF(Zaa)$_z$(±C) | [SEQ ID NO:57] |
| | (Xaa)$_x$KFTIVF(Zaa)$_z$(Uaa or Sp or Poly)$_u$ | [SEQ ID NO:58] |
| | (±C)(Xaa)$_x$KFTIVF(±C)(Zaa)$_z$(Uaak or Sp or Poly)$_u$ | [SEQ ID NO:58] |
| | (Xaa)$_x$(±C)KFTIVF(±C)(Zaa)$_z$(UaaK or Sp or Poly)$_u$ | [SEQ ID NO:59] |
| CONCATEMERS | [(Xaa)$_x$(±C)RGDSP(±C)(Zaa)$_z$]$_p$ | [SEQ ID NO:32] |
| | (Uaa or Sp or Poly)$_u$[(Xaa)$_x$(±C)RGDSP(±C)(Zaa)$_z$]$_p$ | [SEQ ID NO:32] |
| | [(Xaa)$_x$(±C)RGDMF(±C)(Zaa)$_z$]$_p$ | [SEQ ID NO:37] |
| | (Uaa or Sp or Poly)$_u$[(Xaa)$_m$(±C)RGDMF(±C)(Zaa)$_z$]$_p$ | [SEQ ID NO:37] |
| | [(Xaa)$_x$(±C)DELPQLVTLPHPNLHGPEILDVPST(±C)(Zaa)$_z$]$_p$ | [SEQ ID NO:45] |
| | (Uaa or Sp or Poly)$_u$[(Xaa)$_x$(±C)DELPQLVTLPHPNLHGPEILDVPST(±C)(Zaa)$_z$]$_p$ | [SEQ ID NO:45] |
| | [(Xaa)$_x$(±C)DELPQLVTLPHPNLHGPEILDVPST(±C)(Zaa)$_z$]$_p$(Uaa or Sp or Poly)$_u$ | [SEQ ID NO:45] |
| | [(Xaa)$_x$(±C)EILDVPST(±C)(Zaa)$_z$]$_p$ | [SEQ ID NO:50] |
| | (Uaa or Sp or Poly)$_u$[(Xaa)$_x$(±C)EILDVPST(±C)(Zaa)$_z$]$_p$ | [SEQ ID NO:50] |
| | [(Xaa)$_x$(±C)KFTIVF(±C)(Zaa)$_z$]$_p$ | [SEQ ID NO:56] |
| | (Uaa or Sp or Poly)$_u$[(Xaa)$_x$(±C)KFTIVF(±C)(Zaa)$_z$]$_p$ | [SEQ ID NO:56] |
| | (±C)[(Xaa)$_x$RGDSP(Zaa)$_z$]$_p$(±C) | [SEQ ID NO:32] |
| | (Uaa or Sp or Poly)$_u$[(Xaa)$_x$(±C)RGDSP(Zaa)$_z$]$_p$(±C) | [SEQ ID NO:32] |
| | (±C)(Xaa)$_x$RGDMF(Zaa)$_z$]$_p$(±C) | [SEQ ID NO:37] |
| | (Uaa or Sp or Poly)$_u$[(Xaa)$_m$(±C)RGDMF(Zaa)$_z$]$_p$(±C) | [SEQ ID NO:37] |
| | (±C)[(Xaa)$_x$DELPQLVTLPHPNLHGPEILDVPST(Zaa)$_z$]$_p$(±C) | [SEQ ID NO:43] |
| | (Uaa or Sp or Poly)$_u$[(Xaa)$_x$(±C)DELPQLVTLPHPNLHGPEILDVPST(Zaa)$_z$]$_p$(±C) | [SEQ ID NO:45] |
| | (±C)[(Xaa)$_x$DELPQLVTLPHPNLHGPEILDVPST(±C)(Zaa)$_z$]$_p$(Uaa or Sp or Poly)$_u$ | [SEQ ID NO:45] |
| | (±C)[(Xaa)$_x$EILDVPST(Zaa)$_z$]$_p$(±C) | [SEQ ID NO:50] |
| | (Uaa or Sp or Poly)$_u$[(Xaa)$_x$(±C)EILDVPST(Zaa)$_z$]$_p$(±C) | [SEQ ID NO:50] |
| | (±C)[(Xaa)$_x$KFTIVF(Zaa)$_z$]$_p$(±C) | [SEQ ID NO:56] |
| | (Uaa or Sp or Poly)$_u$[(Xaa)$_x$(±C)KFTIVF(Zaa)$_z$]$_p$(±C) | [SEQ ID NO:56] |
| MIXED | [(Baa)$_b$(±C)(±Y or W)(Xaa)$_x$PKKKRKV(Jaa)$_j$RGDMF(±C)(Zaa)$_z$]$_p$ | [SEQ ID NO:60] |
| CONCATEMERS | (Uaa or Sp or Poly)$_u$[(Baa)$_b$(±C)(Xaa)$_x$(±Y or W)PKKKRKV(Jaa)$_j$RGDMF(±C)(Zaa)$_z$]$_p$ | [SEQ ID NO:61] |
| | [(Baa)$_b$(±C)(±Y or W)(Xaa)$_x$PKKKRKV(Jaa)$_j$GRGDSP(±C)(Zaa)$_z$]$_p$ | [SEQ ID NO:62] |
| | (Uaa or Sp or Poly)$_u$[(Baa)$_b$(±C)(Xaa)$_x$(±Y or W)PKKKRKV(Jaa)$_j$RGDSP(±C)(Zaa)$_z$]$_p$ | [SEQ ID NO:63] |
| | [(Baa)$_b$(±C)KFTIVF(±C)(Xaa)$_x$(Jaa)$_j$(±Y or W)(Xaa)$_x$PKKKRKV(Zaa)$_z$]$_p$ | [SEQ ID NO:64] |
| | (Uaa or Sp or Poly)$_u$[(Baa)$_b$(±C)KFTIVF(±C)(Xaa)$_x$(±C)(Jaa)$_j$(±Y or W)PKKKRKV(Zaa)$_z$]$_p$ | [SEQ ID NO:65] |
| | [(Baa)$_b$(±C)(±Y or W)(Xaa)$_x$GPKKKRKV(Jaa)$_j$EILDVSPT(±C)(Zaa)$_z$]$_p$ | [SEQ ID NO:66] |
| | (Uaa or Sp or Poly)$_u$[(Baa)$_b$(±C)(±Y or W)PKKKRKV(Jaa)$_j$EILDVSPT(±C)(Zaa)$_z$]$_p$ | [SEQ ID NO:67] |
| | [(Baa)$_b$(±C)KFTIVF(±C)(Xaa)$_x$EILDVPST(±C)(Zaa)$_z$]$_p$ | [SEQ ID NO:68] |
| | (Uaa or Sp or Poly)$_u$[(Baa)$_b$(±C)KFTIVF(±C)(Xaa)$_x$EILDVPST(±C)(Zaa)$_z$]$_p$ | [SEQ ID NO:68] |
| | (±C)[(Baa)$_b$(±Y or W)(Xaa)$_x$PKKRRKV(Jaa)$_j$RGDMF(Zaa)$_z$]$_p$(±C) | [SEQ ID NO:69] |
| | (Uaa or Sp or Poly)$_u$[(Baa)$_b$(±C)(Xaa)$_x$(±Y or W)PKKKRKV(Jaa)$_j$RGDMF(Zaa)$_z$]$_p$(±C) | [SEQ ID NO:70] |
| | (±C)[(Baa)$_b$(±Y or W)(Xaa)$_x$PKKKRKV(Jaa)$_j$GRGDSP(Zaa)$_z$]$_p$(±C) | [SEQ ID NO:71] |
| | (Uaa or Sp or Poly)$_u$[(Baa)$_b$(±C)(±Y or W)(Xaa)$_x$PKKKRKV(Jaa)$_j$RGDSP(Zaa)$_z$]$_p$(±C) | [SEQ ID NO:72] |
| | (±C)[(Baa)$_b$KFTIVF(±C)(Xaa)$_x$(±C)(Jaa)$_j$(±Y or W)(Xaa)$_x$PKKKRKV(Zaa)$_z$]$_p$(±C) | [SEQ ID NO:73] |

TABLE 2-continued

Exemplary Peptides For Enhancement of Transfection[1]

|  |  |  |
|---|---|---|
|  | (Uaa or Sp or Poly)$_u$[(Baa)$_b$(±C)KFTIVF(±C)(Xaa)$_x$(±C)(Jaa)$_j$(±Y or W)PKKKRKV(Zaa)$_z$]$_p$(±C) | [SEQ ID NO:74] |
|  | (±C)[(Baa)$_b$(±Y or W)(Xaa)$_x$GPKKKRKV(Jaa)$_j$EILDVSPT(Zaa)$_z$]$_p$(±C) | [SEQ ID NO:75] |
|  | (Uaa or Sp or Poly)$_u$[(Baa)$_b$(±C)(±Y or W)PKKKRKV(Jaa)$_j$EILDVSPT(Zaa)$_z$]$_p$(±C) | [SEQ ID NO:76] |
|  | (±C)[(Baa)$_b$KFTIVF(±C)(Xaa)$_x$EILDVPST(Zaa)$_z$]$_p$(±C) | [SEQ ID NO:77] |
|  | (Uaa or Sp or Poly)$_u$[(Baa)$_b$(±C)KFTIVF(±C)(Xaa)$_x$EILDVPST)(Zaa)$_z$]$_p$(±C) | [SEQ ID NO:68] |
| CIRCULAR LDV | (Uaa or Sp or Poly)$_u$(Xaa)$_x$CEILDVPSTC(Zaa)$_z$ | [SEQ ID NO:78] |
| CIRCULAR RGD, penton base | (Uaa or Sp or Poly)$_u$(Xaa)$_x$CHAIRGDTFAC(Zaa)$_z$ | [SEQ ID NO:79] |

Where b, u, j, x, z, n and p are integers that can range from 0-20, Baa, Jaa, Xaa, and Zaa represent any amino acid and Uaa is used to represent any cationic amino acid, designations (Baa)$_b$, (Xaa)$_x$, (Jaa)$_j$, and (Zaa)$_z$ represent any combination of amino acids whether multiple, repeated or not repeated;
Where "±" indicates that any amino acid is optional;
Where Sp is a spermine (including carboxy spermine or spermines coupled to linkers)\;
Where Poly is any other polyamine; and.
Where standard one-letter codes are used for amino acids.

TABLE 3

Additional Examples of Specific Peptides for Transfection Enhancement

| Designation | [SEQuence[1] |  |
|---|---|---|
| VSVGD6 | GKFTIVFDDDDDD(±G) | [SEQ ID NO:80] |
| VSVGE5 | KFTIVFGGGLFEAIAEFIEGGWEGLIEG | [SEQ ID NO:81] |
| E5VSVG | GLFEAIAEFIEGGWEGLIEGCKFTIVF | [SEQ ID NO:82] |
| NLSE5 | CGYGGGGGGPKKKRKVGGGLFEAIAEFIEGGWEGLIEG | [SEQ ID NO:83] |
| E5NLS | GLFEAIAEFIEGGWEGLIEGGGYGGGGGGPKKKRKVGG | [SEQ ID NO:84] |
| VSVGNLS | KFTTIVFCGYGPKKKRKVGG | [SEQ ID NO:85] |
| NLSVSVG | CGYGPKKKRKVGGKFTIVF | [SEQ ID NO:86] |
| K16VSVGD6 | $K_{16}$GKFTIVFDDDDDD(±G) | [SEQ ID NO:87] |
| K16VSVGE5 | $K_{16}$KFTIVFGGGLFEAIAEFIEGGWEGLIEG | [SEQ ID NO:88] |
| K16E5VSVG | $K_{16}$GLFEAIAEFIEGGWEGLIEGCKFITVF | [SEQ ID NO:89] |
| K16E5NLS | $K_{16}$GLFEAIAEFIEGGWEGLIEGGGYGGGGGGPKKKRKVGG | [SEQ ID NO:90] |
| K16VSVGNLS | $K_{16}$KFTTIVFCGYGPKKKRKVGG | [SEQ ID.NO:91] |
| K16NLSVSVG | $K_{16}$GGCGYGGGPKKKRKVGGKFTIVF | [SEQ ID NO:92] |
| K16NLSE5 | $K_{16}$GGCGYGGGGGGPKKKRKVGGGLFEAIAEFIEGGWEGLIEG | [SEQ ID NO:93] |
| NLS | SSDDEATADSQHSTPPKKKRKVGG | [SEQ ID NO:94] |
| phosphorylation | $K_{16}$SSDDEATADSQHSTPPKKKRKVGG | [SEQ ID NO:95] |
| HIS-TEV-peptides: |  |  |
| HIS-TEV- | MSYYHHHHHHDYDIPTTENLYFQGS-peptide | [SEQ ID NO:96] |
| HIS-TEV-NLS | MSYYHHHHHHDYDIPTTENLYFQGSGYGPKKKRKVGG | [SEQ ID NO:97] |
| HIS-TEV-VSVG | MSYYHHHHHHDYDIPTTENLYFQGSKFTIVF | [SEQ ID NO:98] |
| HIS-TEV-E5 | MSYYHHHHHHDYDIPTTENLYFQGSGLFEAIAEFIEGGWEGLIEG | [SEQ ID NO:99] |
| HIS-TEV-RGD | MSYYHHHHHHDYDIPTTENLYFQGSRGDSPC | [SEQ ID NO:100] |
| 6HIS-peptides | MSYYHHHHHH-peptide | [SEQ ID NO:101] |
| 6HIS-NLS | MSYYHHHHHHGYGPKKKRVGG | [SEQ ID NO:102] |
| 6HIS-VSVG | MSYYHHHHHHKFTIVF | [SEQ ID NO:103] |
| 6HIS-E5 | MSYYHHHHHHGLFEAIAEFIEGGWEGLIEG | [SEQ ID NO:104] |
| 6HIS-RGD | MSYYHHHHHHRGDSPC | [SEQ ID NO:105] |
| peptide-6HIS | peptide-HHHHHH | [SEQ ID NO:106] |

[1]Peptide [SEQuences in this Table can be combined with polyamines, including spermine, or other nucleic acid-binding groups including strings of cationic amino acids at their N- or C- terminus.

TABLE 4

Examples of Spermine-Conjugated Peptides[1]

| Spermine-Conjugated Peptide |  | Designation |
|---|---|---|
| Sp-5-CO-NH-CH$_2$-CO-GGGGYGPKKKRKVGG | [SEQ ID NO:107] | Opf-GG-1 |
| Sp-5-CO-NH-CH$_2$-CO-GYGPKKKRKVG | [SEQ ID NO:108] | Opf-GG-2 |
| Sp-5-CO-NH-CH$_2$-CO-CGYGPKKKRKVG | [SEQ ID NO:109] | Opf-GG-2-CYS |
| Sp-5-CO-NH-CH$_2$-CO-GRGDMFGG | [SEQ ID NO:110] | Sp-RGD |
| Sp-5-CO-NH-CH$_2$-CO-YGPKKKRKVGGGGGRGDMFGG | [SEQ ID NO:111] | Sp-NLSRGD |
| Sp-5-CO-NH-CH$_2$-CO-GYGPKKKRKVGGGGYGPKKKRKVGG | [SEQ ID NO 13] | Sp-NLSNLS |
| SP-5-CO-NH-CH((CH$_2$)$_4$-NH-5-CO-Sp)-CO-GGYGPKKKRKVGGGGYGPKKKRKVGG | [SEQ ID NO:13] | Sp$_2$-NLSNLS |

[1]Prepared using automated solid phase peptide synthesis.

TABLE 5

Un-Modified Peptides Peptides Tested for Enhancement of "LIPOFECTAMINE" Transfections in Human Fibroblasts by Inclusion in Transfection Medium

| Designation | [SEQuence | | Enhancement in Transfect | Peptide Amount µM |
|---|---|---|---|---|
| HApep | GLFGAIAGFIENGWEGMIDG | [SEQ ID NO:112] | " | 10 |
| E5 | GLFEAIAEFIEGGWEGLIEG | [SEQ ID NO:113] | See FIG. 1 | 0.1 |
| K5 | GLFKAIAKFIKGGWKGLIKG | [SEQ ID NO:114] | " | 5 |
| HApep | GLFGAIAGFIENGWEGMIDG | [SEQ ID NO:112] | " | 10 |
| VSVG | KFTIVF | [SEQ ID NO:54] | " | 1 |

TABLE 6

Comparison of "LIPOFECTAMINE" Transfection +/− Sp-NLSNLS

| Transfection Reagents | Transfection Conditions: DNA (µg) | lipid (µl) | Specific Activity ng β-gal/ µg protein | Protein Yield µg/Well |
|---|---|---|---|---|
| "LIPOFECTAMINE" | 0.4 | 2 | 0.07 | 67.5 |
| "LIPOFECTAMINE" + Sp-NLSNLS | 0.1 | 1 | 0.38 | 85.5 |

TABLE 7

Enhancement of "LIPOFECTAMINE" Transfections in Human Fibroblasts for Peptides and Derivatized Peptides[1]

| Designation | [SEQuence | | Enhancement | Peptide Amount (mg per 0.4 mg DNA) |
|---|---|---|---|---|
| NLS | GYGPKKKRKVGG | [SEQ ID NO:115] | 7–10 | 20 |
| Opf-GG-1 | Sp-5-CO-GGGGGYGPKKKRKVGG | [SEQ ID NO:107] | 4 | 6 |
| Opf-GG-2 (peak 1) | Sp-5-CO-GGYGPKKKRKVG | [SEQ ID NO 108] | 5 | 10 |
| Opf-GG-2 (peak 2) | partially deblocked[2] Sp-5-CO-GGYGPKKKRKVG | [SEQ ID NO:108] | 7 | 2 |
| Opf-GG-2-CYS (peak 1) | Sp-5-CO-GCGYGPKKKRKVG | [SEQ ID NO:109] | 5 | 10 |
| Opf-GG-2-CYS (peak 2) | partially deblocked[2] Sp-5-CO-GCGYGPKKKRKVG | [SEQ ID NO:109] | 7 | 20 |
| SpRGD | Sp-5-CO-GGRGDMFGG | [SEQ ID NO:110] | 5[3] | 12[3] |
| SpNLSRGD | Sp-5-CO-GYGPKKKRKVGGGGGRGDMFGG | [SEQ ID NO:111] | 4 | 20 |
| SpNLSNLS | Sp-5-CO-GGYGPKKKRKVGGGGYGPKKKRKVGG | [SEQ ID NO:13] | 7–10 | 4 |
| K16NLS (peak 1) | K₁₆GGCGYGPKKKRKVGG | [SEQ ID NO:116] | 5 | 10 |
| " (peak 2) | partially deblocked[2] K₁₆GGCGYGPKKKRKVGG | [SEQ ID NO:116] | 6 | 0.5 |
| K16NLSRGD | K₁₆CGYGPKKKRKVGGGGRGDSP | [SEQ ID NO:117] | 10 | 2 |
| K16RGD | K₁₆GGRGDSPCG | [SEQ ID NO:118] | 10 | 2 |
| RGDK16 | GRGDSPCGGK₁₆ | [SEQ ID NO:119] | 6 | 5 |
| K16 | K₁₆ | [SEQ ID NO:4] | 2 | 0.5 |
| G61934P NLSRGD | CGYGPKKKRKVGGGGRGDSPCG | [SEQ ID NO:120] | 8 | 20 |

[1]The results in this table were compiled from a series of experiments, i.e., the peptides were not all compared in the same experiment. The data are the fold enhancement of "LIPOFECTAMINE" transfections at peak activity in human fibroblasts (unless otherwise noted) in 24-well plates, with 0.4 mg DNA per transfection. The DNA transfected was either pCMVSPORTβgal or pCMVβ, and the assays were all done with ONPG.
[2]These peptide were only partially deprotected following automatic peptide synthesis and were isolated as a side-product of the fully deprotected peptide as a separate peak on HPLC. These peptides carry one protecting group(Mtr) and that protecting group is believed to be on the R residue of the PKKKRK [SEQuence (NLS). R-Mtr is generally more difficult to deprotect. The protecting (i.e., blocking group) that remains on the peptide is an Mtr group which is a conventional amino acid blocking gro

TABLE 7-continued

Enhancement of "LIPOFECTAMINE" Transfections in Human Fibroblasts for Peptides and Derivatized Peptides[1]

| Designation [SEQuence | Enhancement | Peptide Amount (mg per 0.4 mg DNA) |
|---|---|---|

[3]The experiment was done with CHO-K1 cells and the amount of DNA used (either pCMVSPORTβgal or pCMVβ) is 0.2 mg DNA per well in 24-well plates.

TABLE 8

Enhancement of DMRIE-C Transfections by Peptides in Human Suspension Cells (K562 or JurkatCells)[1]

| Peptide/Cell Type | Enhancement -Fold | Peptide Amount µg/0.4 µg DNA | DMRIE-C µL |
|---|---|---|---|
| E5: GLFEAIAEFIEGGWEGLIEG [SEQ ID NO:113] | | | |
| K562 | 3 | 5 | 1.6 |
| Jurkat | 1.2 | 5 | 1.6 |
| K16NLS (peak 2) | 1 | — | 1.6 |
| K562 or Jurkat | | | |
| K16NLSRGD | 1 | 1 | 1.6 |
| K562 or Jurkat | | | |
| K16NLSRGD + E5 | 1.8 | 2.5 + 2.5 | 1.6 |
| K562 | | | |

[1]The results in this table were complied from a series of experiments. The peptides were not all compared in the same experiment. The data listed are the fold enhancement of DMRIE-C transfections at peak activity (both for DMRIE-C alone and for the peptide combination) in suspension cell lines as indicated. Assays were done using either pCMVSPORTβ-gal or pCMVβ, assaying with CAT.

TABLE 9

Enhancement of Dendrimer-Mediated Transfection by Peptides and Spermine-Conjugated Peptides in COS-7 Cells

| Transfection Agent | Peptide Agent | RLU |
|---|---|---|
| Lipofectamine | None | 32971 |
| " | K16NLS (peak 2) | 164105 |
| " | Sp-NLSNLS | 200447 |
| " | NLS | 224029 |
| G7(EDA) | None | 478 |
| " | K16NLS (peak 2) | 3423 |
| " | Sp-NLSNLS | 2832 |
| " | NLS | 2749 |
| G9(EDA) | None | 518 |
| " | K16NLS (peak 2) | 2297 |
| " | Sp-NLSNLS | 1702 |
| " | NLS | 1747 |
| Arg DMER | None | 29139 |
| " | K16NLS (peak 2) | 63307 |
| " | Sp-NLSNLS | 56548 |
| " | NLS | 84209 |
| Lys DMER | None | 2448 |
| " | K16NLS (peak 2) | 20847 |
| " | Sp-NLSNLS | 17203 |
| " | None | 17689 |
| "COMB BURST" | NLS | 18453 |
| " | K16NLS (peak 2) | 28562 |
| " | Sp-NLSNLS | 23503 |
| " | NLS | 29639 |

We claim:

1. A method for transfecting a eukaryotic cell with a nucleic acid, said method comprising the steps of:
   (a) admixing a fusagenic peptide with a nucleic acid to form a peptide-nucleic acid complex;
   (b) adding a transfection agent to the complex from step (a) to obtain an aggregate of said transfection agent and said complex comprising said peptide-nucleic acid complex; and
   (c) contacting said eukaryotic cell with the aggregate from step (b).

2. The method of claim 1, wherein said fusagenic peptide is a peptide of a viral protein derived from a virus selected from the group consisting of an influenza virus, a vesicular stomatitis virus, and an alphavirus.

3. The method of claim 1, wherein said fusagenic peptide is a hemagglutinin of an influenza virus or a glycoprotein of a vesicular stomatitis virus.

4. The method of claim 3 wherein said fusagenic peptide is an amphiphilic peptide of a hemagglutinin of an influenza virus.

5. The method of claim 1 wherein said peptide comprises a VSVG, E5, or K5 sequence.

6. A method for transfecting a eukaryotic cell with a nucleic acid, said method comprising the steps of:
   (a) admixing a mixture of peptides with a nucleic acid to form a peptide-nucleic acid complex;
   (b) adding a transfection agent to the complex from step (a) to obtain an aggregate of said transfection agent and said complex comprising said peptide-nucleic acid complex; and
   (c) contacting said eukaryotic cell with the aggregate from step (b).

7. The method of claim 6 wherein said peptide mixture is a mixture of an amphiphilic peptide of a hemagglutinin and a fusagenic peptide.

8. The method of claim 7 wherein said peptide mixture is a mixture of VSVG and E5.

9. A method for transfecting a eukaryotic cell with a nucleic acid, said method comprising the steps of:
   (a) admixing a mixture of peptides with a nucleic acid to form a peptide-nucleic acid complex;
   (b) adding a transfection agent to the complex from step (a) to obtain an aggregate of said transfection agent and said complex comprising said peptide-nucleic acid complex; and
   (c) contacting said eukaryotic cell with the aggregate from step (b), wherein said transfection agent comprises a cationic lipid.

10. The method of claim 9 wherein said cationic lipid is a polyvalent cationic lipid.

11. The method of claim 10 wherein said polyvalent cationic lipid is 2,3-dioleyloxy-N-[2(sperminecarboxamido)ethyl]-N,N-dimethyl-1-propanaminium trifluoroacetate.

12. The method of claim 10 wherein said transfection agent is a 3:1 (w/w) mixture of the polycationic lipid2,3-dioleyloxy-N-[2(sperminecarboxamido)ethyl]-N,N-dimethyl-1-propanaminium trifluoroacetate and dioleoylphosphatidyl-ethanolamine.

13. The method of claim 9 where in step (b) a mixture of a cationic lipid and a neutral lipid is added to said complex of step (a).

14. The method of claim 13 wherein said neutral lipid is dioleoylphosphatidylethanolamine.

15. The method of claim 9 wherein said transfection agent comprises a 1:1 (W/W) mixture of 1,2-dimyristyloxypropyl-1-3-dimethylhydroxyethyl ammonium bromide) and cholesterol.

16. A composition for transfecting a eukaryotic cell produced by first forming a composition comprising a peptide-nucleic acid complex followed by addition of a cationic lipid composition which aggregates said peptide-nucleic acid complex.

17. The composition of claim 16 wherein said cationic lipid composition comprises a polycationic lipid.

18. The composition of claim 17 wherein said polycationic lipid is 2,3-dioleyloxy-N-[2(sperminecarboxamido)ethyl]-N,N-dimethyl-1-propanaminium trifluoroacetate.

19. The composition of claim 16 wherein said cationic lipid composition further comprises a neutral lipid.

20. The composition of claim 19 wherein said neutral lipid is dioleoylphosphatidylethanolamine.

21. The composition of claim 20 wherein said cationic lipid composition is a 3:1 (w/w) mixture of the polycationic lipid2,3-dioleyloxy-N-[2(sperminecarboxamido)ethyl]-N,N-dimethyl-1-propanaminium trifluoroacetate and dioleoylphosphatidyl-ethanolamine.

22. The composition of claim 16 wherein said cationic lipid composition comprises DMRIE-C which is a 1:1

(W/W) mixture of 1,2-dimyristyloxypropyl-1-3-dimethylhydroxyethyl ammonium bromide) and cholesterol.

23. The composition of claim 16 wherein said peptide is a fusagenic peptide, a membrane-permeabilizing peptide, a sub-cellular localization sequence, or a cell-receptor ligand.

24. A transfection composition which comprises a cationic lipid covalently linked to a peptide wherein the covalently linked cationic lipid functions in transfection.

25. The transfection composition of claim 24 wherein said lipid is covalently attached to said peptide via a linking group.

26. The transfection composition of claim 24 wherein said peptide is a fusagenic peptide, a membrane-permeabilizing peptide, a sub-cellular localization peptide, or a cell-receptor ligand.

27. The transfection composition of claim 26 wherein said peptide is a VSVG peptide, an RGD peptide, an E5 peptide, an LDV peptide, or an NLS peptide.

28. The transfection composition of claim 24 wherein said peptide is a fusagenic peptide, a membrane-permeabilizing peptide, or a cell-receptor ligand.

29. The transfection composition of claim 28 wherein said peptide comprises a VSVG peptide sequence, an RGD peptide sequence, an E5 peptide sequence, an LDV peptide sequence, or an NLS peptide sequence.

30. The transfection composition of claim 24 further comprising nucleic acid.

31. A method for transfecting a eukaryotic cell which comprises the step of contacting said cell with the composition of claim 24.

32. The transfection composition of claim 24 wherein the lipid is DOTMA or DOTAP.

33. A transfection reagent kit which comprises a cationic lipid transfection agent and a peptide or modified peptide which comprises an NLS sequence and enhances transfection by said transfection agent.

34. The kit of claim 33 wherein said cationic lipid transfection agent is a 3:1 (w/w) mixture of the polycationic lipid2,3-dioleyloxy-N-[2(sperminecarboxamido)ethyl]-N,N-dimethyl-1-propaniminium trifluoroacetate and dioleoylphosphatidyl-ethanolamine.

35. The kit of claim 33 wherein said peptide is Sp-NLSNLS.

36. The kit of claim 33 wherein said peptide is K16NLS peak 2.

37. The kit of claim 33 wherein said peptide is NLS.

38. The kit of claim 33 wherein said cationic lipid is a polycationic lipid.

39. The kit of claim 33 wherein said peptide is NLS.

40. The kit of claim 33 wherein said peptide is NLSNLS.

41. The kit of claim 33 wherein said peptide is a concatemer.

42. The kit of claim 33 wherein said peptide further comprises a VSVG, E5, K5, LDV, or RGD peptide sequence.

43. The kit of claim 42 wherein said peptide is a mixed concatemer.

44. The kit of claim 33 wherein said peptide is modified by covalent bonding to a nucleic acid binding group.

45. The kit of claim 44 wherein said nucleic acid-binding group is a polyamine.

46. The kit of claim 44 wherein said nucleic acid-binding group is spermine.

47. The kit of claim 44 wherein said nucleic acid-binding group comprises cationic amino acids.

48. A method for transfecting a eukaryotic cell with a nucleic acid, said method comprising the steps of:

(a) admixing a fusagenic peptide modified by covalent bonding to a nucleic acid-binding group with a nucleic acid to form a peptide-nucleic acid complex;

(b) adding a transfection agent to the complex from step (a) to obtain an aggregate of said transfection agent and said complex comprising said peptide-nucleic acid complex; and (c) contacting said eukaryotic cell with the aggregate from step (b).

49. The method of claim 48 wherein said nucleic acid-binding group is a polyamine.

50. The method of claim 48 wherein said nucleic acid-binding group is spermine.

51. The method of claim 48 wherein said nucleic acid-binding group comprises cationic amino acids.

52. The method of claim 51 wherein said nucleic acid-binding group comprises the cationic peptide sequence $(Uaa)_u$ where each amino acid, Uaa, in the sequence, independently of any other amino acid in the sequence can be lysine, arginine, ornithine, homoarginine, or histidine and where u is an integer from 1 to about 20.

53. The method of claim 52 wherein u is an integer ranging from about 8 to about 20.

54. The method of claim 53 wherein each amino acid, Uaa, in the sequence $(Uaa)_u$ is the same amino acid.

55. The method of claim 51 wherein said nucleic acid-binding group further comprises glycine or proline residues.

56. The method of claim 55 wherein said nucleic acid-binding group comprises the cationic peptide sequence $(Uaa)_u$ where each amino acid, Uaa, in the sequence, independently of any other amino acid in the sequence can be lysine, arginine, ornithine, homoarginine, histidine, glycine or proline and where u is an integer from 1 to about 20.

57. The method of claim 48 wherein said peptide comprises a VSVG, E5, or K5 sequence.

58. The method of claim 48 wherein said peptide is a concatemer, a mixed concatemer or a dimer.

59. The method of claim 48 wherein a mixture of different peptides is admixed in step (a).

60. A method for transfecting a eukaryotic cell with a nucleic acid, said method comprising the steps of:

(a) admixing a cell adhesion ligand peptide comprising an RGD or LDV peptide sequence with a nucleic acid to form a peptide-nucleic acid complex;

(b) adding a transfection agent to the complex from step (a) to obtain an aggregate of said transfection agent and said complex comprising said peptide-nucleic acid complex; and (c) contacting said eukaryotic cell with the aggregate from step (b).

61. The method of claim 60 wherein the peptide comprises a sequence selected from RGDSP [SEQ ID NO. 32] or RGDMF [SEQ ID NO. 36].

62. The method of claim 60 wherein said peptide is modified by covalent bonding to a nucleic acid binding group.

63. The method of claim 62 wherein said nucleic acid-binding group is a polyamine.

64. The method of claim 62 wherein said nucleic acid-binding group is spermine.

65. The method of claim 62 wherein said nucleic acid-binding group comprises cationic amino acids.

66. The method of claim 62 wherein said nucleic acid-binding group comprises the cationic peptide sequence $(Uaa)_u$ where each amino acid, Uaa, in the sequence, independently of any other amino acid in the sequence can be lysine, arginine, ornithine, homoarginine, or histidine and where u is an integer from 1 to about 20.

67. The method of claim 66 wherein u is an integer ranging from about 8 to about 20.

68. The method of claim 66 wherein each amino acid, Uaa, in the sequence (Uaa)$_u$ is the same amino acid.

69. The method of claim 62 wherein said nucleic acid-binding group further comprises glycine or proline residues.

70. The method of claim 69 wherein said nucleic acid-binding group comprises the cationic peptide sequence (Uaa)$_u$ where each amino acid, Uaa, in the sequence, independently of any other amino acid in the sequence can be lysine, arginine, ornithine, homoarginine, histidine, glycine or proline and where u is an integer from 1 to about 20.

71. The method of claim 60 wherein said peptide is a concatemer, a mixed concatemer or a dimer.

72. The method of claim 60 wherein a mixture of different peptides is admixed in step (a).

73. A method for transfecting a eukaryotic cell with a nucleic acid, said method comprising the steps of:

(a) admixing a peptide that is modified by covalent bonding to a nucleic acid-binding group with a nucleic acid to form a peptide-nucleic acid complex;

(b) adding a transfection agent to the complex from step (a) to obtain an aggregate of said transfection agent and said complex comprising said peptide-nucleic acid complex; and (c) contacting said eukaryotic cell with the aggregate from step (b), wherein the nucleic acid-binding group comprises cationic amino acids and glycines or prolines.

74. The method of claim 73 wherein said nucleic acid-binding group comprises the cationic peptide sequence (Uaa)$_u$ where each amino acid, Uaa, in the sequence, independently of any other amino acid in the sequence can be lysine, arginine, ornithine, homoarginine, or histidine and where u is an integer from 1 to about 20.

75. The method of claim 74 wherein u is an integer ranging from about 8 to about 20.

76. The method of claim 75 wherein each amino acid, Uaa, in the sequence (Uaa)$_u$ is the same amino acid.

77. The method of claim 73 wherein the peptide comprises an NLS, VSVG, RGD, LDV, K5, or E5 sequence.

78. The method of claim 73 wherein said peptide is a concatemer, a mixed concatemer or a dimer.

79. The method of claim 73 wherein a mixture of different peptides is admixed in step (a).

80. The method of claim 73 wherein said peptide is a concatemer, a mixed concatemer or a dimer.

81. A method for transfecting a eukaryotic cell with a nucleic acid, said method comprising the steps of:

(a) admixing a peptide comprising an NLS sequence and at least one amino acid protecting group with a nucleic acid to form a peptide-nucleic acid complex;

(b) adding a transfection agent to the complex from step (a) to obtain an aggregate of said transfection agent and said complex comprising said peptide-nucleic acid complex; and (c) contacting said eukaryotic cell with the aggregate from step (b).

82. The method of claim 81 wherein said peptide is modified by covalent bonding to a nucleic acid binding group.

83. The method of claim 82 wherein said nucleic acid-binding group is a polyamine.

84. The method of claim 83 wherein said nucleic acid-binding group is spermine.

85. The method of claim 81 wherein the peptide is (Uaa)$_u$NLS where Uaa, independently of any other Uaa, is a cationic amino acid and u is an integer from 1 to about 20 and having at least one amino acid blocked with a protecting group.

86. The method of claim 81 wherein a Uaa of the NLS sequence is blocked with a protecting group or is replaced with an aromatic amino acid.

87. The method of claim 85 wherein the protecting group comprises an aromatic group.

88. The method of claim 82 wherein said nucleic acid-binding group comprises cationic amino acids.

89. The method of claim 88 wherein said nucleic acid-binding group comprises the cationic peptide sequence (Uaa)$_u$ where each amino acid, Uaa, in the sequence, independently of any other amino acid in the sequence can be lysine, arginine, ornithine, homoarginine, or histidine and where u is an integer from 1 to about 20.

90. A transfection composition which comprises a neutral lipid covalently linked to a peptide and a cationic lipid.

91. The transfection composition of claim 90 wherein said cationic lipid is a polycationic lipid.

92. The transfection composition of claim 90 wherein said peptide comprises an NLS, VSVG, RGD, LDV, K5, or E5 sequence.

93. The transfection composition of claim 90 wherein said peptide is a fusagenic peptide.

94. The transfection composition of claim 90 wherein said peptide binds to a binding site on the surface of a eukaryotic cell.

95. The transfection composition of claim 90 wherein said peptide is a concatemer, a mixed concatemer or a dimer which comprises a VSVG, E5, K5, LDV, RGD, or NLS peptide sequence.

* * * * *

UNITED STATES PATENT AND TRADEMARK OFFICE
CERTIFICATE OF CORRECTION

PATENT NO. : 6,051,429
DATED : Apr. 18, 2000
INVENTOR(S) :
Hawley-Nelson et al.

It is certified that error appears in the above-identified patent and that said Letters Patent is hereby corrected as shown below:

At column 20, line 43, please delete "(1920) 22:479)" and replace with --(1980) Cell 22:479)--.
At column 27, please add "II" below the chemical structure at the bottom of the page.
At column 28, please add "II" to the right of the third chemical structure from the top of the page.
At column 28, please add "I" to the right of the chemical structure at the bottom of the page.
At column 173, line 46, please delete claim 39.

Signed and Sealed this

Twenty-ninth Day of May, 2001

Attest:

NICHOLAS P. GODICI

Attesting Officer        Acting Director of the United States Patent and Trademark Office

SEQUENCE LISTING (1) GENERAL INFORMATION:

(iii) NUMBER OF SEQUENCES: 120

(2) INFORMATION FOR SEQ ID NO:1:

(i) SEQUENCE CHARACTERISTICS:
            (A) LENGTH: 10 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

His Ala Ile Arg Gly Asp Thr Phe Ala Thr
1               5                  10

(2) INFORMATION FOR SEQ ID NO:2:

(i) SEQUENCE CHARACTERISTICS:
            (A) LENGTH: 7 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

Pro Lys Lys Lys Arg Lys Val
1               5

(2) INFORMATION FOR SEQ ID NO:3:

(i) SEQUENCE CHARACTERISTICS:
            (A) LENGTH: 8 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Pro Lys Lys Lys Lys Arg Lys Val
1               5

(2) INFORMATION FOR SEQ ID NO:4:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 2..20
            (D) OTHER INFORMATION: /product= "OTHER"
                /note= "ANY OR ALL OF THE AMINO ACIDS 2-20 CAN BE PRESENT
                OR ABSENT"

(xi) SEQUENCE DESCRIPTION: SEQ ID NO:4:

```
Lys Lys Lys Lys Lys Lys Lys Lys Lys Lys Lys Lys Lys Lys Lys Lys
1               5                   10                  15
Lys Lys Lys Lys
            20
```

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 2..20
        (D) OTHER INFORMATION: /product= "OTHER"
            /note= "ANY OR ALL OF THE AMINO ACIDS 2-20 CAN BE PRESENT
            OR ABSENT"

(xi) SEQUENCE DESCRIPTION: SEQ ID NO:5:

```
Arg Arg Arg Arg Arg Arg Arg Arg Arg Arg Arg Arg Arg Arg Arg Arg
1               5                   10                  15
Arg Arg Arg Arg
            20
```

(2) INFORMATION FOR SEQ ID NO:6:

(i) SEQUENCE CHARACTERISTICS:
        (A) LENGTH: 40 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 3..40
        (D) OTHER INFORMATION: /product= "OTHER"
            /note= "ANY Lsy-Arg PAIR FROM AMINO ACID 3-40 CAN BE
            PRESENT OR ABSENT"

(xi) SEQUENCE DESCRIPTION: SEQ ID NO:6:

```
Lys Arg Lys Arg Lys Arg Lys Arg Lys Arg Lys Arg Lys Arg Lys Arg
1               5                   10                  15
Lys Arg Lys Arg Lys Arg Lys Arg Lys Arg Lys Arg Lys Arg Lys Arg
            20                  25                  30
Lys Arg Lys Arg Lys Arg Lys Arg
        35                  40
```

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 2..20
        (D) OTHER INFORMATION: /product= "OTHER"

/note= "ANY OR ALL OF THE AMINO ACIDS 2-20 CAN BE PRESENT
OR ABSENT"

(xi) SEQUENCE DESCRIPTION: SEQ ID NO:7:

Gly Gly Gly Gly Gly Gly Gly Gly Gly Gly Gly Gly Gly Gly Gly Gly
1               5                   10                  15

Gly Gly Gly Gly
        20

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

Gly Arg Gly Asp Ser Pro Cys
1               5

(2) INFORMATION FOR SEQ ID NO:9:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "ANY OR ALL OF THE AMINO ACIDS 1-20 CAN BE PRESENT
            OR ABSENT"

(xi) SEQUENCE DESCRIPTION: SEQ ID NO:9:

Lys Lys Lys Lys Lys Lys Lys Lys Lys Lys Lys Lys Lys Lys Lys Lys
1               5                   10                  15

Lys Lys Lys Lys Arg Gly Asp
        20

(2) INFORMATION FOR SEQ ID NO:10:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:10:

Lys Lys Lys Lys Lys Lys Lys Lys Lys Lys Lys Lys Lys Lys Lys Lys
1               5                   10                  15

Arg Gly Asp (2) INFORMATION FOR SEQ ID NO:11:

(i) SEQUENCE CHARACTERISTICS:

(A) LENGTH: 7 amino acids
(B) TYPE: amino acid
(C) STRANDEDNESS: Not Relevant
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:11:

Lys Phe Thr Ile Val Phe Cys
1               5

(2) INFORMATION FOR SEQ ID NO:12:

(i) SEQUENCE CHARACTERISTICS:
(A) LENGTH: 12 amino acids
(B) TYPE: amino acid
(C) STRANDEDNESS: Not Relevant
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:12:

Cys Gly Trp Gly Pro Lys Lys Lys Arg Lys Val Gly
1               5                   10

(2) INFORMATION FOR SEQ ID NO:13:

(i) SEQUENCE CHARACTERISTICS:
(A) LENGTH: 26 amino acids
(B) TYPE: amino acid
(C) STRANDEDNESS: Not Relevant
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:13:

Gly Gly Tyr Gly Pro Lys Lys Lys Arg Lys Val Gly Gly Gly Tyr
1               5                   10                  15

Gly Pro Lys Lys Lys Arg Lys Val Gly Gly
                20                  25

(2) INFORMATION FOR SEQ ID NO:14:

(i) SEQUENCE CHARACTERISTICS:
(A) LENGTH: 6 amino acids
(B) TYPE: amino acid
(C) STRANDEDNESS: Not Relevant
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:14:

Arg Gly Asp Ser Pro Cys
1               5

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:15:

Arg Glu Asp Val
1

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:16:

Arg Gly Asp Val
1

(2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:17:

Asp Glu Leu Pro Gln Leu Val Thr Leu Pro His Pro Asn Leu His Gly
1               5                   10                  15

Pro Glu Ile Leu Asp Val Pro Ser Thr
            20                  25

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:18:

Arg Gly Asp Asn
1

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:19:

Arg Gly Asp Met
1

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:20:

Arg Gly Asp Thr
1

(2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4
        (D) OTHER INFORMATION: /product= "OTHER"
            /note= "Xaa AT POSITION 4 CAN BE ANY AMINO ACID"

(xi) SEQUENCE DESCRIPTION: SEQ ID NO:21:

Arg Gly Asp Xaa
1

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:22:

Arg Gly Asp Ser
1

(2) INFORMATION FOR SEQ ID NO:23:

(i) SEQUENCE CHARACTERISTICS:
            (A) LENGTH: 4 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:23:

Arg Gly Asp Ala
1

(2) INFORMATION FOR SEQ ID NO:24:

(i) SEQUENCE CHARACTERISTICS:
            (A) LENGTH: 33 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "C AT POSITION 1 CAN BE ABSENT"

(ix) FEATURE:
            (A) NAME/KEY: Modified-site
            (B) LOCATION: 3
            (D) OTHER INFORMATION: /product= "OTHER"
                /note= "Xaa AT POSITION 3 CAN BE TYR OR TRP OR CAN BE
                ABSENT"

(ix) FEATURE:
            (A) NAME/KEY: Modified-site
            (B) LOCATION: 14..33
            (D) OTHER INFORMATION: /product= "OTHER"
                /note= "ANY OR ALL OF THE GLY AT POSITIONS 14 TO 33 CAN
                BE ABSENT"

(xi) SEQUENCE DESCRIPTION: SEQ ID NO:24:

Cys Gly Xaa Gly Pro Lys Lys Lys Arg Lys Val Gly Gly Gly Gly
1               5                   10                  15

Gly Gly Gly Gly Gly Gly Gly Gly Gly Gly Gly Gly Gly Gly Gly
            20                  25                  30

Gly (2) INFORMATION FOR SEQ ID NO:25:

(i) SEQUENCE CHARACTERISTICS:
            (A) LENGTH: 48 amino acids
            (B) TYPE: amino acid
            (C) STRANDEDNESS: Not Relevant (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                    /note= "Xaa AT POSITIONS 1-20 CAN BE ANY AMINO ACIDS AND
                    ANY OR ALL OF THESE AMINO ACIDS CAN BE ABSENT "

(ix) FEATURE:
            (A) NAME/KEY: Modified-site
            (B) LOCATION: 28
            (D) OTHER INFORMATION: /product= "OTHER"
                    /note= "Xaa AT POSITION 28 CAN BE TYR OR TRP OR CAN BE
                    ABSENT"

(ix) FEATURE:
            (A) NAME/KEY: Modified-site
            (B) LOCATION: 29..48
            (D) OTHER INFORMATION: /product= "OTHER"
                    /note= "Xaa AT POSITIONS 29-48 CAN BE ANY AMINO ACIDS OR
                    CAN BE ABSENT"

(xi) SEQUENCE DESCRIPTION: SEQ ID NO:25:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Pro Lys Lys Lys Arg Lys Val Xaa Xaa Xaa Xaa Xaa
        20                  25                  30

Xaa Xaa Xaa Xaa Xaa Xaa Xaa Xaa Xaa Xaa Xaa Xaa Xaa Xaa Xaa Xaa
        35                  40                  45

(2) INFORMATION FOR SEQ ID NO:26:

(i) SEQUENCE CHARACTERISTICS:
            (A) LENGTH: 90 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                    /note= "Xaa AT POSITIONS 1-20 CAN BE ANY AMINO ACIDS OR
                    ANY OF THESE AMINO ACIDS CAN BE ABSENT"

(ix) FEATURE:
            (A) NAME/KEY: Modified-site
            (B) LOCATION: 21
            (D) OTHER INFORMATION: /product= "OTHER"
                    /note= "CYS AT POSITON 21 CAN BE ABSENT"

(ix) FEATURE:
            (A) NAME/KEY: Modified-site
            (B) LOCATION: 22
            (D) OTHER INFORMATION: /product= "OTHER"
                    /note= "Xaa AT POSITION 22 CAN BE TYR OR TRP OR CAN BE
                    ABSENT"

(ix) FEATURE:
            (A) NAME/KEY: Modified-site
            (B) LOCATION: 23..42
            (D) OTHER INFORMATION: /product= "OTHER"
                    /note= "Xaa AT POSITIONS 23-42 CAN BE ANY AMINO ACIDS OR
                    ANY OF THESE AMINO ACIDS CAN BE ABSENT"

(ix) FEATURE:
            (A) NAME/KEY: Modified-site
            (B) LOCATION: 50
            (D) OTHER INFORMATION: /product= "OTHER"
                    /note= "CYS AT POSITION 50 CAN BE ABSENT"

```
      (ix) FEATURE:
           (A) NAME/KEY: Modified-site
           (B) LOCATION: 51..70
           (D) OTHER INFORMATION: /product= "OTHER"
               /note= "Xaa AT POSITIONS 51 TO 79 CAN BE ANY AMINO ACIDS
               OR ANY OF THESE AMINO ACIDS CAN BE ABSENT"

(ix) FEATURE:
           (A) NAME/KEY: Modified-site
           (B) LOCATION: 71..90
           (D) OTHER INFORMATION: /product= "OTHER"
               /note= "Xaa AT POSITIONS 71-90 CAN BE ANY CATIONIC AMINO
               ACIDS OR ANY OF THESE AMINO ACIDS CAN BE ABSENT"

(xi) SEQUENCE DESCRIPTION: SEQ ID NO:26:

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
            35                  40                  45

Val Cys Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa
                85                  90

(2) INFORMATION FOR SEQ ID NO:27:

(i) SEQUENCE CHARACTERISTICS:
           (A) LENGTH: 70 amino acids
           (B) TYPE: amino acid
           (C) STRANDEDNESS: Not Relevant
           (D) TOPOLOGY: linear (ii) MOLECULE TYPE: peptide (ix) FEATURE:
           (A) NAME/KEY: Modified-site
           (B) LOCATION: 1
           (D) OTHER INFORMATION: /product= "OTHER"
               /note= "CYS AT POSITION 1 CAN BE ABSENT"

(ix) FEATURE:
           (A) NAME/KEY: Modified-site
           (B) LOCATION: 2..21
           (D) OTHER INFORMATION: /product= "OTHER"
               /note= "Xaa AT POSITIONS 2-21 CAN BE ANY AMINO ACIDS OR
               ANY OF THESE AMNION ACIDS CAN BE ABSENT"

(ix) FEATURE:
           (A) NAME/KEY: Modified-site
           (B) LOCATION: 22
           (D) OTHER INFORMATION: /product= "OTHER"
               /note= "Xaa AT POSITION 22 CAN BE TYR OR TRP OR CAN BE
               ABSENT"

(ix) FEATURE:
           (A) NAME/KEY: Modified-site
           (B) LOCATION: 23..42
           (D) OTHER INFORMATION: /product= "OTHER"
               /note= "Xaa AT POSITIONS 23 TO 42 CAN BE ANY AMNIO ACIDS
               OR ANY OF THESE AMINO ACIDS CAN BE ABSENT"

(ix) FEATURE:
           (A) NAME/KEY: Modified-site
           (B) LOCATION: 50..69
           (D) OTHER INFORMATION: /product= "OTHER"
               /note= "Xaa AT POSITIONS 50 TO 69 CAN BE ANY AMINO ACIDS
               OR ANY OF THESE AMINO ACIDS CAN BE ABSENT"
```

(ix) FEATURE:
              (A) NAME/KEY: Modified-site
              (B) LOCATION: 70
              (D) OTHER INFORMATION: /product= "OTHER"
                  /note= "CYS AT POSITION 70 CAN BE ABSENT"

(xi) SEQUENCE DESCRIPTION: SEQ ID NO:27:

Cys Xaa Xaa Xaa Xaa Xaa Xaa Xaa Xaa Xaa Xaa Xaa Xaa Xaa Xaa
1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
        35                  40                  45

Val Xaa Xaa Xaa Xaa Xaa Xaa Xaa Xaa Xaa Xaa Xaa Xaa Xaa Xaa
    50                  55                  60

Xaa Xaa Xaa Xaa Xaa Cys
65                  70

(2) INFORMATION FOR SEQ ID NO:28:

(i) SEQUENCE CHARACTERISTICS:
              (A) LENGTH: 90 amino acids
              (B) TYPE: amino acid
              (C) STRANDEDNESS: Not Relevant
              (D) TOPOLOGY: linear (ii) MOLECULE TYPE: peptide (ix) FEATURE:
              (A) NAME/KEY: Modified-site
              (B) LOCATION: 1
              (D) OTHER INFORMATION: /product= "OTHER"
                  /note= "CYS AT POSITION 1 CAN BE ABSENT"

(ix) FEATURE:
              (A) NAME/KEY: Modified-site
              (B) LOCATION: 2..21
              (D) OTHER INFORMATION: /product= "OTHER"
                  /note= "Xaa AT POSITIONS 2-21 CAN BE ANY AMINO ACIDS OR
                  ANY OF THESE AMINO ACIDS CAN BE ABSENT"

(ix) FEATURE:
              (A) NAME/KEY: Modified-site
              (B) LOCATION: 22
              (D) OTHER INFORMATION: /product= "OTHER"
                  /note= "Xaa AT POSITION 22 CAN BE TYR OR TRP OR CAN BE
                  ABSENT"

(ix) FEATURE:
              (A) NAME/KEY: Modified-site
              (B) LOCATION: 23..42
              (D) OTHER INFORMATION: /product= "OTHER"
                  /note= "Xaa AT POSITIONS 23-42 CAN BE ANY AMINO ACIDS OR
                  CAN BE ABSENT"

(ix) FEATURE:
              (A) NAME/KEY: Modified-site
              (B) LOCATION: 50
              (D) OTHER INFORMATION: /product= "OTHER"
                  /note= "CYS AT POSITION 50 CAN BE ABSENT"

(ix) FEATURE:
              (A) NAME/KEY: Modified-site
              (B) LOCATION: 51..70
              (D) OTHER INFORMATION: /product= "OTHER"
                  /note= "Xaa AT POSITIONS 51 TO 70 CAN BE ANY AMINO ACIDS
                  AND CAN BE ABSENT"

(ix) FEATURE:
              (A) NAME/KEY: Modified-site
              (B) LOCATION: 71..90
              (D) OTHER INFORMATION: /product= "OTHER"

/note= "Xaa AT POSITIONS 71-90 CAN BE ANY CATIONIC AMINO
ACIDS OR CAN BE ABSENT"

(xi) SEQUENCE DESCRIPTION: SEQ ID NO:28:

```
Cys Xaa Xaa Xaa Xaa Xaa Xaa Xaa Xaa Xaa Xaa Xaa Xaa Xaa Xaa
1               5                  10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Pro Lys Lys Lys Arg Lys
            35                  40                  45

Val Cys Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa
                85                  90
```

(2) INFORMATION FOR SEQ ID NO:29:

(i) SEQUENCE CHARACTERISTICS:
      (A) LENGTH: 90 amino acids
      (B) TYPE: amino acid
      (C) STRANDEDNESS: Not Relevant
      (D) TOPOLOGY: linear (ii) MOLECULE TYPE: peptide (ix) FEATURE:
      (A) NAME/KEY: Modified-site
      (B) LOCATION: 1..20
      (D) OTHER INFORMATION: /product= "OTHER"
          /note= "Xaa AT POSITIONS 1-20 CAN BE ANY CATIONIC AMINO
          ACIDS OR CAN BE AB..."

(ix) FEATURE:
      (A) NAME/KEY: Modified-site
      (B) LOCATION: 21..40
      (D) OTHER INFORMATION: /product= "OTHER"
          /note= "Xaa AT POSITIONS 21 TO 40 CAN BE ANY AMINO ACIDS
          OR CAN BE ABSENT"

(ix) FEATURE:
      (A) NAME/KEY: Modified-site
      (B) LOCATION: 41
      (D) OTHER INFORMATION: /product= "OTHER"
          /note= "CYS AT POSITION 41 CAN BE ABSENT"

(ix) FEATURE:
      (A) NAME/KEY: Modified-site
      (B) LOCATION: 42
      (D) OTHER INFORMATION: /product= "OTHER"
          /note= "Xaa AT POSITION 42 CAN BE TYR OT TRP OR CAN BE
          ABSENT"

(ix) FEATURE:
      (A) NAME/KEY: Modified-site
      (B) LOCATION: 43..62
      (D) OTHER INFORMATION: /product= "OTHER"
          /note= "Xaa AT POSITIONS 43 TO 62 CAN BE ANY AMINO ACIDS
          OR CAN BE ABSENT"

(ix) FEATURE:
      (A) NAME/KEY: Modified-site
      (B) LOCATION: 70..89
      (D) OTHER INFORMATION: /product= "OTHER"
          /note= "Xaa AT POSITIONS 70 TO 89 CAN BE ANY AMINO ACIDS
          OR CAN BE ABSENT"

(ix) FEATURE:
      (A) NAME/KEY: Modified-site
      (B) LOCATION: 90
      (D) OTHER INFORMATION: /product= "OTHER"

/note= "CYS AT POSITION 90 CAN BE ABSENT"

(xi) SEQUENCE DESCRIPTION: SEQ ID NO:29:

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Cys Xaa Xaa Xaa Xaa Xaa Xaa
        35                  40                  45

Xaa Xaa Xaa Xaa Xaa Xaa Xaa Xaa Xaa Xaa Xaa Xaa Xaa Pro Lys
    50                  55                  60

Lys Lys Arg Lys Val Xaa Xaa Xaa Xaa Xaa Xaa Xaa Xaa Xaa Xaa
65                  70                  75                  80

Xaa Xaa Xaa Xaa Xaa Xaa Xaa Xaa Xaa Cys
            85                  90
```

(2) INFORMATION FOR SEQ ID NO:30:

(i) SEQUENCE CHARACTERISTICS:
        (A) LENGTH: 90 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACID OR CAN BE ABSENT"

(ix) FEATURE:
        (A) NAME/KEY: Modified-site
        (B) LOCATION: 21..40
        (D) OTHER INFORMATION: /product= "OTHER"
            /note= "Xaa AT POSITIONS 21 TO 40 CAN BE ANY AMINO ACIDS
            OR CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 42
        (D) OTHER INFORMATION: /product= "OTHER"
            /note= "Xaa AT POSITION 42 CAN BE TYR OR TRP OR CAN BE
            ABSENT"

(ix) FEATURE:
        (A) NAME/KEY: Modified-site
        (B) LOCATION: 43..62
        (D) OTHER INFORMATION: /product= "OTHER"
            /note= "Xaa AT POSITIONS 43 TO 62 CAN BE ANY AMINO ACIDS
            OR CAN
            BE ABSENT"

(ix) FEATURE:
        (A) NAME/KEY: Modified-site
        (B) LOCATION: 70
        (D) OTHER INFORMATION: /product= "OTHER"
            /note= "CYS AT POSITION 70 CAN BE ABSENT"

(ix) FEATURE:
        (A) NAME/KEY: Modified-site
        (B) LOCATION: 71..90
        (D) OTHER INFORMATION: /product= "OTHER"
            /note= "Xaa AT POSITIONS 71 TO 90 CAN BE ANY AMINO ACIDS

OR CAN BE ABSENT"

(xi) SEQUENCE DESCRIPTION: SEQ ID NO:30:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Cys Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Pro Lys
    50                  55                  60

Lys Lys Arg Lys Val Cys Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa
                85                  90

(2) INFORMATION FOR SEQ ID NO:31:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:31:

Arg Gly Asp Ser Pro
1               5

(2) INFORMATION FOR SEQ ID NO:32:

(i) SEQUENCE CHARACTERISTICS:
        (A) LENGTH: 69 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 42
        (D) OTHER INFORMATION: /product= "OTHER"
            /note= "GLY AT POSITION 42 CAN BE ABSENT"

(ix) FEATURE:
        (A) NAME/KEY: Modified-site
        (B) LOCATION: 48
        (D) OTHER INFORMATION: /product= "OTHER"

/note= "GLY AT POSITION 48 CAN BE ABSENT"

(ix) FEATURE:
(A) NAME/KEY: Modified-site
(B) LOCATION: 49
(D) OTHER INFORMATION: /product= "OTHER"
/note= "CYS AT POSITION 49 CAN BE ABSENT"

(ix) FEATURE:
(A) NAME/KEY: Modified-site
(B) LOCATION: 50..69
(D) OTHER INFORMATION: /product= "OTHER"
/note= "Xaa AT POSITIONS 50-69 CAN BE ANY AMINO ACIDS OR CAN BE ABSENT"

(xi) SEQUENCE DESCRIPTION: SEQ ID NO:32:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Gly Arg Gly Asp Ser Pro Gly
        35                  40                  45

Cys Xaa Xaa Xaa Xaa Xaa Xaa Xaa Xaa Xaa Xaa Xaa Xaa Xaa Xaa Xaa
50                  55                  60

Xaa Xaa Xaa Xaa Xaa
65
```

(2) INFORMATION FOR SEQ ID NO:33:

(i) SEQUENCE CHARACTERISTICS:
(A) LENGTH: 69 amino acids
(B) TYPE: amino acid
(C) STRANDEDNESS: Not Relevant
(D) TOPOLOGY: linear (ii) MOLECULE TYPE: peptide (ix) FEATURE:
(A) NAME/KEY: Modified-site
(B) LOCATION: 1..20
(D) OTHER INFORMATION: /product= "OTHER"
/note= "Xaa AT POSITIONS 1-20 CAN BE ANY AMINO ACIDS OR CAN BE ABSENT"

(ix) FEATURE:
(A) NAME/KEY: Modified-site
(B) LOCATION: 21
(D) OTHER INFORMATION: /product= "OTHER"
/note= "CYS AT POSITION 21 CAN BE ABSENT"

(ix) FEATURE:
(A) NAME/KEY: Modified-site
(B) LOCATION: 22
(D) OTHER INFORMATION: /product= "OTHER"
/note= "GLY AT POSITION 22 CAN BE ABSENT"

(ix) FEATURE:
(A) NAME/KEY: Modified-site
(B) LOCATION: 28
(D) OTHER INFORMATION: /product= "OTHER"
/note= "GLY AT POSITION 28 CAN BE ABSENT"

(ix) FEATURE:
(A) NAME/KEY: Modified-site
(B) LOCATION: 29
(D) OTHER INFORMATION: /product= "OTHER"
/note= "CYS AT POSITION 29 CAN BE ABSENT"

(ix) FEATURE:
(A) NAME/KEY: Modified-site
(B) LOCATION: 30..49
(D) OTHER INFORMATION: /product= "OTHER"
/note= "Xaa AT POSITIONS 30-49 CAN BE ANY AMINO ACIDS OR -continued

```
                CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50 -69 CAN BE ANY CATIONIC AMINO
            ACIDS"

(xi) SEQUENCE DESCRIPTION: SEQ ID NO:33:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Gly Arg Gly Asp Ser Pro Gly Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa
65

(2) INFORMATION FOR SEQ ID NO:34:

(i) SEQUENCE CHARACTERISTICS:
        (A) LENGTH: 69 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 42
        (D) OTHER INFORMATION: /product= "OTHER"
            /note= "GLY AT POSITION 42 CAN BE ABSENT"

(ix) FEATURE:
        (A) NAME/KEY: Modified-site
        (B) LOCATION: 48
        (D) OTHER INFORMATION: /product= "OTHER"
            /note= "GLY AT POSITION 48 CAN BE ABSENT"

(ix) FEATURE:
        (A) NAME/KEY: Modified-site
        (B) LOCATION: 49..68
        (D) OTHER INFORMATION: /product= "OTHER"
            /note= "Xaa AT POSITIONS 49-68 CAN BE ANY AMINO ACIDS OR
            CAN BE ABSENT"

(ix) FEATURE:
        (A) NAME/KEY: Modified-site
        (B) LOCATION: 69
```

(D) OTHER INFORMATION: /product= "OTHER"
                    /note= "CYS AT POSITION 69 CAN BE ABSENT"

(xi) SEQUENCE DESCRIPTION: SEQ ID NO:34:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Gly Arg Gly Asp Ser Pro Gly
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Cys
65

(2) INFORMATION FOR SEQ ID NO:35:

(i) SEQUENCE CHARACTERISTICS:
        (A) LENGTH: 69 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "CYS AT POSITION 1 CAN BE ABSENT"

(ix) FEATURE:
        (A) NAME/KEY: Modified-site
        (B) LOCATION: 2..21
        (D) OTHER INFORMATION: /product= "OTHER"
            /note= "Xaa AT POSITIONS 2-21 CAN BE ANY AMINO ACID OR
            CAN BE ABSENT"

(ix) FEATURE:
        (A) NAME/KEY: Modified-site
        (B) LOCATION: 22
        (D) OTHER INFORMATION: /product= "OTHER"
            /note= "GLY AT POSITION 22 CAN BE ABSENT"

(ix) FEATURE:
        (A) NAME/KEY: Modified-site
        (B) LOCATION: 28
        (D) OTHER INFORMATION: /product= "OTHER"
            /note= "GLY AT POSITION 28 CAN BE ABSENT"

(ix) FEATURE:
        (A) NAME/KEY: Modified-site
        (B) LOCATION: 29
        (D) OTHER INFORMATION: /product= "OTHER"
            /note= "CYS AT POSITION 29 CAN BE ABSENT"

(ix) FEATURE:
        (A) NAME/KEY: Modified-site
        (B) LOCATION: 30..49
        (D) OTHER INFORMATION: /product= "OTHER"
            /note= "Xaa AT POSITIONS 30-49 CAN BE ANY AMINO ACIDS OR
            CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY CATIONIC AMINO
            ACIDS OR CAN BE ABSENT"

(xi) SEQUENCE DESCRIPTION: SEQ ID NO:35:

Cys Xaa Xaa Xaa Xaa Xaa Xaa Xaa Xaa Xaa Xaa Xaa Xaa Xaa Xaa Xaa

```
 1               5              10              15
Xaa Xaa Xaa Xaa Xaa Gly Arg Gly Asp Ser Pro Gly Cys Xaa Xaa Xaa
                    20              25              30
Xaa Xaa Xaa Xaa Xaa Xaa Xaa Xaa Xaa Xaa Xaa Xaa Xaa Xaa Xaa Xaa
                35              40              45
Xaa Xaa Xaa Xaa Xaa Xaa Xaa Xaa Xaa Xaa Xaa Xaa Xaa Xaa Xaa Xaa
    50              55              60

Xaa Xaa Xaa Xaa Xaa
65
```

(2) INFORMATION FOR SEQ ID NO:36:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:36:

```
Arg Gly Asp Met Phe
 1               5
```

(2) INFORMATION FOR SEQ ID NO:37:

(i) SEQUENCE CHARACTERISTICS:
        (A) LENGTH: 49 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "GLY AT POSITION 22 CAN BE ABSENT"

(ix) FEATURE:
        (A) NAME/KEY: Modified-site
        (B) LOCATION: 28
        (D) OTHER INFORMATION: /product= "OTHER"
            /note= "GLY AT POSITION 28 CAN BE ABSENT"

(ix) FEATURE:
        (A) NAME/KEY: Modified-site
        (B) LOCATION: 29
        (D) OTHER INFORMATION: /product= "OTHER"
            /note= "CYS AT POSITION 29 CAN BE ABSENT"

(ix) FEATURE:
        (A) NAME/KEY: Modified-site
        (B) LOCATION: 30..49
        (D) OTHER INFORMATION: /product= "OTHER"
            /note= "Xaa AT POSITIONS 30-49 CAN BE ANY AMINO ACIDS OR
            CAN BE ABSENT"

(xi) SEQUENCE DESCRIPTION: SEQ ID NO:37:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Gly Arg Gly Asp Met Phe Gly Cys Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa (2) INFORMATION FOR SEQ ID NO:38:

(i) SEQUENCE CHARACTERISTICS:
        (A) LENGTH: 47 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "CYS AT POSITION 1 CAN BE ABSENT"

(ix) FEATURE:
        (A) NAME/KEY: Modified-site
        (B) LOCATION: 2..21
        (D) OTHER INFORMATION: /product= "OTHER"
            /note= "Xaa AT POSITIONS 2-21 CAN BE ANY AMINO ACIDS OR
            CAN BE ABSENT"

(ix) FEATURE:
        (A) NAME/KEY: Modified-site
        (B) LOCATION: 27..46
        (D) OTHER INFORMATION: /product= "OTHER"
            /note= "Xaa AT POSITIONS 27-46 CAN BE ANY AMINO ACIDS OR
            CAN BE ABSENT"

(ix) FEATURE:
        (A) NAME/KEY: Modified-site
        (B) LOCATION: 47
        (D) OTHER INFORMATION: /product= "OTHER"
            /note= "CYS AT POSITION 47 CAN BE ABSENT"

(xi) SEQUENCE DESCRIPTION: SEQ ID NO:38:

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Arg Gly Asp Met Phe Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Cys
        35                  40                  45

(2) INFORMATION FOR SEQ ID NO:39:

(i) SEQUENCE CHARACTERISTICS:
        (A) LENGTH: 69 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

```
      (ix) FEATURE:
            (A) NAME/KEY: Modified-site
            (B) LOCATION: 21..40
            (D) OTHER INFORMATION: /product= "OTHER"
                /note= "Xaa AT POSITIONS 21-40 CAN BE ANY AMINO ACIDS OR
                CAN BE ABSENT"

(ix) FEATURE:
            (A) NAME/KEY: Modified-site
            (B) LOCATION: 41
            (D) OTHER INFORMATION: /product= "OTHER"
                /note= "CYS AT POSITION 41 CAN BE ABSENT"

(ix) FEATURE:
            (A) NAME/KEY: Modified-site
            (B) LOCATION: 42
            (D) OTHER INFORMATION: /product= "OTHER"
                /note= "GLY AT POSITION 42 CAN BE ABSENT"

(ix) FEATURE:
            (A) NAME/KEY: Modified-site
            (B) LOCATION: 48
            (D) OTHER INFORMATION: /product= "OTHER"
                /note= "GLY AT POSITION 48 CAN BE ABSENT"

(ix) FEATURE:
            (A) NAME/KEY: Modified-site
            (B) LOCATION: 49..68
            (D) OTHER INFORMATION: /product= "OTHER"
                /note= "Xaa AT POSITIONS 49-68 CAN BE ANY AMINO ACIDS OR
                CAN BE ABSENT"

(ix) FEATURE:
            (A) NAME/KEY: Modified-site
            (B) LOCATION: 69
            (D) OTHER INFORMATION: /product= "OTHER"
                /note= "CYS AT POSITION 69 CAN BE ABSENT"

(xi) SEQUENCE DESCRIPTION: SEQ ID NO:39:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Cys Gly Arg Gly Asp Met Phe Gly
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Cys
65

(2) INFORMATION FOR SEQ ID NO:40:

(i) SEQUENCE CHARACTERISTICS:
            (A) LENGTH: 69 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 2..21
            (D) OTHER INFORMATION: /product= "OTHER"
                /note= "Xaa AT POSITIONS 2-21 CAN BE ANY AMINO ACIDS OR
                CAN BE ABSENT"
```

(ix) FEATURE:
            (A) NAME/KEY: Modified-site
            (B) LOCATION: 22
            (D) OTHER INFORMATION: /product= "OTHER"
                /note= "GLY AT POSITION 22 CAN BE ABSENT"

(ix) FEATURE:
            (A) NAME/KEY: Modified-site
            (B) LOCATION: 28
            (D) OTHER INFORMATION: /product= "OTHER"
                /note= "GLY AT POSITION 28 CAN BE ABSENT"

(ix) FEATURE:
            (A) NAME/KEY: Modified-site
            (B) LOCATION: 29
            (D) OTHER INFORMATION: /product= "OTHER"
                /note= "CYS AT POSITION 29 CAN BE ABSENT"

(ix) FEATURE:
            (A) NAME/KEY: Modified-site
            (B) LOCATION: 30..49
            (D) OTHER INFORMATION: /product= "OTHER"
                /note= "Xaa AT POSITIONS 30-49 CAN BE ANY AMINO ACIDS OR
                CAN BE ABSENT"

(ix) FEATURE:
            (A) NAME/KEY: Modified-site
            (B) LOCATION: 50..69
            (D) OTHER INFORMATION: /product= "OTHER"
                /note= "Xaa AT POSITIONS 50-69 CAN BE ANY CATIONIC AMINO
                ACIDS OR CAN BE ABSENT"

(xi) SEQUENCE DESCRIPTION: SEQ ID NO:40:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Gly Arg Gly Asp Met Phe Gly Cys Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

(2) INFORMATION FOR SEQ ID NO:41:

(i) SEQUENCE CHARACTERISTICS:
         (A) LENGTH: 69 amino acids
         (B) TYPE: amino acid
         (C) STRANDEDNESS: Not Relevant
         (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa AT POSITIONS 1-20 CAN BE ANY CATIONIC AMINO
             ACIDS OR CAN BE AB..."

(ix) FEATURE:
         (A) NAME/KEY: Modified-site
         (B) LOCATION: 21..40
         (D) OTHER INFORMATION: /product= "OTHER"
             /note= "Xaa AT POSITIONS 21-40 CAN BE ANY AMINO ACIDS OR
             CAN BE ABSENT"

(ix) FEATURE:
         (A) NAME/KEY: Modified-site
         (B) LOCATION: 41
         (D) OTHER INFORMATION: /product= "OTHER"
             /note= "CYS AT POSITION 41 CAN BE ABSENT"

(ix) FEATURE:
    (A) NAME/KEY: Modified-site
    (B) LOCATION: 42
    (D) OTHER INFORMATION: /product= "OTHER"
        /note= "GLY AT POSITION 42 CAN BE ABSENT"

(ix) FEATURE:
    (A) NAME/KEY: Modified-site
    (B) LOCATION: 48
    (D) OTHER INFORMATION: /product= "OTHRE"
        /note= "GLY AT POSITION 48 CAN BE ABSENT"

(ix) FEATURE:
    (A) NAME/KEY: Modified-site
    (B) LOCATION: 49
    (D) OTHER INFORMATION: /product= "OTHER"
        /note= "CYS AT POSITION 49 CAN BE ABSENT"

(ix) FEATURE:
    (A) NAME/KEY: Modified-site
    (B) LOCATION: 50..69
    (D) OTHER INFORMATION: /product= "OTHER"
        /note= "Xaa AT POSITIONS 50-69 CAN BE ANY AMINO ACIDS OR
        CAN BE ABSENT"

(xi) SEQUENCE DESCRIPTION: SEQ ID NO:41:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Cys Gly Arg Gly Asp Met Phe Gly
            35                  40                  45

Cys Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

(2) INFORMATION FOR SEQ ID NO:42:

(i) SEQUENCE CHARACTERISTICS:
        (A) LENGTH: 69 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "GLY AT POSITION 22 CAN BE ABSENT"

(ix) FEATURE:
        (A) NAME/KEY: Modified-site
        (B) LOCATION: 28
        (D) OTHER INFORMATION: /product= "OTHER"
            /note= "GLY AT POSITION 28 CAN BE ABSENT"

(ix) FEATURE:
            (A) NAME/KEY: Modified-site
            (B) LOCATION: 29
            (D) OTHER INFORMATION: /product= "OTHER"
                /note= "CYS AT POSITION 29 CAN BE ABSENT"

(ix) FEATURE:
            (A) NAME/KEY: Modified-site
            (B) LOCATION: 30..49
            (D) OTHER INFORMATION: /product= "OTHER"
                /note= "Xaa AT POSITIONS 30-49 CAN BE ANY AMINO ACIDS OR
                CAN BE ABSENT"

(ix) FEATURE:
            (A) NAME/KEY: Modified-site
            (B) LOCATION: 50..69
            (D) OTHER INFORMATION: /product= "OTHER"
                /note= "Xaa AT POSITIONS 50-69 CAN BE ANY CATIONIC AMINO
                ACIDS OR CAN BE ABSENT"

(xi) SEQUENCE DESCRIPTION: SEQ ID NO:42:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Gly Arg Gly Asp Met Phe Gly Cys Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa
65

(2) INFORMATION FOR SEQ ID NO:43:

(i) SEQUENCE CHARACTERISTICS:
            (A) LENGTH: 67 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 2..21
            (D) OTHER INFORMATION: /product= "OTHER"
                /note= "Xaa AT POSITIONS 2-21 CAN BE ANY AMINO ACIDS OR
                CAN BE ABSENT"

(ix) FEATURE:
            (A) NAME/KEY: Modified-site
            (B) LOCATION: 47..66
            (D) OTHER INFORMATION: /product= "OTHER"
                /note= "Xaa AT POSITIONS 47-66 CAN BE ANY AMINO ACIDS OR
                CAN BE ABSENT"

(ix) FEATURE:
            (A) NAME/KEY: Modified-site
            (B) LOCATION: 67
            (D) OTHER INFORMATION: /product= "OTHER"
                /note= "CYS AT POSITION 67 CAN BE ABSENT"

(xi) SEQUENCE DESCRIPTION: SEQ ID NO:43:

Cys Xaa Xaa Xaa Xaa Xaa Xaa Xaa Xaa Xaa Xaa Xaa Xaa Xaa Xaa Xaa
1               5                   10                  15

```
Xaa Xaa Xaa Xaa Xaa Asp Glu Leu Pro Gln Leu Val Thr Leu Pro His
            20                  25                  30

Pro Asn Leu His Gly Pro Glu Ile Leu Asp Val Pro Ser Thr Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Cys
65
```

(2) INFORMATION FOR SEQ ID NO:44:

(i) SEQUENCE CHARACTERISTICS:
        (A) LENGTH: 87 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
        ACID OR CAN BE ABSENT"

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
        CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 67..86
        (D) OTHER INFORMATION: /product= "OTHER"
            /note= "Xaa AT POSITIONS 67-86 CAN BE ANY AMINO ACIDS OR
        CAN BE ABSENT"

(ix) FEATURE:
        (A) NAME/KEY: Modified-site
        (B) LOCATION: 87
        (D) OTHER INFORMATION: /product= "OTHER"
            /note= "CYS AT POSITION 87 CAN BE ABSENT"

(xi) SEQUENCE DESCRIPTION: SEQ ID NO:44:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Asp Glu Leu Pro Gln Leu Val
            35                  40                  45

Thr Leu Pro His Pro Asn Leu His Gly Pro Glu Ile Leu Asp Val Pro
    50                  55                  60

Ser Thr Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Cys
            85
```

(2) INFORMATION FOR SEQ ID NO:45:

(i) SEQUENCE CHARACTERISTICS:
  (A) LENGTH: 87 amino acids
  (B) TYPE: amino acid
  (C) STRANDEDNESS: Not Relevant
  (D) TOPOLOGY: linear (ii) MOLECULE TYPE: peptide (ix) FEATURE:
  (A) NAME/KEY: Modified-site
  (B) LOCATION: 1..20
  (D) OTHER INFORMATION: /product= "OTHER"
      /note= "Xaa AT POSITIONS 1-20 CAN BE ANY CATIONIC AMINO
      ACIDS OR CAN BE AB..."

(ix) FEATURE:
  (A) NAME/KEY: Modified-site
  (B) LOCATION: 21..40
  (D) OTHER INFORMATION: /product= "OTHER"
      /note= "Xaa AT POSITIONS 21-40 CAN BE ANY AMINO ACIDS OR
      CAN BE ABSENT"

(ix) FEATURE:
  (A) NAME/KEY: Modified-site
  (B) LOCATION: 41
  (D) OTHER INFORMATION: /product= "OTHER"
      /note= "CYS AT POSTION 41 CAN BE ABSENT"

(ix) FEATURE:
  (A) NAME/KEY: Modified-site
  (B) LOCATION: 67
  (D) OTHER INFORMATION: /product= "OTHER"
      /note= "CYS AT POSITION 67 CAN BE ABSENT"

(ix) FEATURE:
  (A) NAME/KEY: Modified-site
  (B) LOCATION: 68..87
  (D) OTHER INFORMATION: /product= "OTHER"
      /note= "Xaa AT POSITIONS 68-87 CAN BE ANY AMINO ACIDS OR
      CAN BE ABSENT"

(xi) SEQUENCE DESCRIPTION: SEQ ID NO:45:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Asp Glu Leu Pro Gln Leu Val
        35                  40                  45

Thr Leu Pro His Pro Asn Leu His Gly Pro Glu Ile Leu Asp Val Pro
        50                  55                  60

Ser Thr Cys Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
            85
```

(2) INFORMATION FOR SEQ ID NO:46:

(i) SEQUENCE CHARACTERISTICS:
  (A) LENGTH: 87 amino acids
  (B) TYPE: amino acid
  (C) STRANDEDNESS: Not Relevant
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /product= "OTHER"
      /note= "CYS AT POSITION 1 CAN BE ABSENT"

(ix) FEATURE:

(A) NAME/KEY: Modified-site
         (B) LOCATION: 2..21
         (D) OTHER INFORMATION: /product= "OTHER"
             /note= "Xaa AT POSITIONS 2-21 CAN BE ANY AMINO ACID OR
             CAN BE ABSENT"

(ix) FEATURE:
         (A) NAME/KEY: Modified-site
         (B) LOCATION: 47
         (D) OTHER INFORMATION: /product= "OTHER"
             /note= "CYS AT POSITION 47 CAN BE ABSENT"

(ix) FEATURE:
         (A) NAME/KEY: Modified-site
         (B) LOCATION: 48..67
         (D) OTHER INFORMATION: /product= "OTHER"
             /note= "Xaa AT POSITIONS 48-67 CAN BE ANY AMINO ACIDS OR
             CAN BE ABSENT"

(ix) FEATURE:
         (A) NAME/KEY: Modified-site
         (B) LOCATION: 68..87
         (D) OTHER INFORMATION: /product= "OTHER"
             /note= "Xaa AT POSITIONS 68-87 CAN BE ANY CATIONIC AMINO
             ACIDS OR CAN BE ABSENT"

(xi) SEQUENCE DESCRIPTION: SEQ ID NO:46:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Asp Glu Leu Pro Gln Leu Val Thr Leu Pro His
                20                  25                  30

Pro Asn Leu His Gly Pro Glu Ile Leu Asp Val Pro Ser Thr Cys Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
            85

(2) INFORMATION FOR SEQ ID NO:47:

(i) SEQUENCE CHARACTERISTICS:
         (A) LENGTH: 87 amino acids
         (B) TYPE: amino acid
         (C) STRANDEDNESS: Not Relevant
         (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa AT POSITIONS 1-20 CAN BE ANY AMINO ACIDS OR
             CAN BE ABSENT"

(ix) FEATURE:
         (A) NAME/KEY: Modified-site
         (B) LOCATION: 21
         (D) OTHER INFORMATION: /product= "OTHER"
             /note= "CYS AT POSITION 21 CAN BE ABSENT"

(ix) FEATURE:
         (A) NAME/KEY: Modified-site
         (B) LOCATION: 47
         (D) OTHER INFORMATION: /product= "OTHER"
             /note= "CYS AT POSITION 47 CAN BE ABSENT"

(ix) FEATURE:
         (A) NAME/KEY: Modified-site
         (B) LOCATION: 48..67

(D) OTHER INFORMATION: /product= "OTHER"
                /note= "Xaa AT POSITIONS 48-67 CAN BE ANY AMINO ACIDS OR
                CAN BE ABSENT"

(ix) FEATURE:
            (A) NAME/KEY: Modified-site
            (B) LOCATION: 68..87
            (D) OTHER INFORMATION: /product= "OTHER"
                /note= "Xaa AT POSITIONS 68-87 CAN BE ANY CATIONIC AMNIO
                ACIDS OR CAN BE ABSENT"

(xi) SEQUENCE DESCRIPTION: SEQ ID NO:47:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Asp Glu Leu Pro Gln Leu Val Thr Leu Pro His
            20                  25                  30

Pro Asn Leu His Gly Pro Glu Ile Leu Asp Val Pro Ser Thr Cys Xaa
            35                  40                  45

Xaa Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
                85

(2) INFORMATION FOR SEQ ID NO:48:

(i) SEQUENCE CHARACTERISTICS:
            (A) LENGTH: 8 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:48:

Glu Ile Leu Asp Val Pro Ser Thr
1               5

(2) INFORMATION FOR SEQ ID NO:49:

(i) SEQUENCE CHARACTERISTICS:
            (A) LENGTH: 50 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 21
            (D) OTHER INFORMATION: /product= "OTHER"
                /note= "Xaa AT POSITIONS 2-21 CAN BE ANY AMINO ACIDS OR
                CAN BE ABSENT"

(ix) FEATURE:
            (A) NAME/KEY: Modified-site
            (B) LOCATION: 30..49
            (D) OTHER INFORMATION: /product= "OTHER"
                /note= "Xaa AT POSITIONS 30-49 CAN BE ANY AMINO ACIDS OR
                CAN BE ABSENT"

(ix) FEATURE:

(A) NAME/KEY: Modified-site
                    (B) LOCATION: 50
                    (D) OTHER INFORMATION: /product= "OTHER"
                        /note= "CYS AT POSITION 50 CAN BE ABSENT"

(xi) SEQUENCE DESCRIPTION: SEQ ID NO:49:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Glu Ile Leu Asp Val Pro Ser Thr Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Cys
    50

(2) INFORMATION FOR SEQ ID NO:50:

(i) SEQUENCE CHARACTERISTICS:
        (A) LENGTH: 70 amino acids
        (B) TYPE: amino acid
        (C) STRANDEDNESS: Not Relevant
        (D) TOPOLOGY: linear (ii) MOLECULE TYPE: peptide (ix) FEATURE:
         (A) NAME/KEY: Modified-site
         (B) LOCATION: 1..20
         (D) OTHER INFORMATION: /product= "OTHER"
             /note= "Xaa AT POSITIONS 1-20 CAN BE ANY CATIONIC AMINO
             ACIDS OR CAN BE AB..."

(ix) FEATURE:
         (A) NAME/KEY: Modified-site
         (B) LOCATION: 21..40
         (D) OTHER INFORMATION: /product= "OTHER"
             /note= "Xaa AT POSITIONS 21-40 CAN BE ANY AMINO ACIDS OR
             CAN BE ABSENT"

(ix) FEATURE:
         (A) NAME/KEY: Modified-site
         (B) LOCATION: 41
         (D) OTHER INFORMATION: /product= "OTHER"
             /note= "CYS AT POSITION 41 CAN BE ABSENT"

(ix) FEATURE:
         (A) NAME/KEY: Modified-site
         (B) LOCATION: 50
         (D) OTHER INFORMATION: /product= "OTHER"
             /note= "CYS AT POSITION 50 CAN BE ABSENT"

(ix) FEATURE:
         (A) NAME/KEY: Modified-site
         (B) LOCATION: 51..70
         (D) OTHER INFORMATION: /product= "OTHER"
             /note= "Xaa AT POSITIONS 51-70 CAN BE ANY AMINO ACIDS OR
             CAN BE ABSENT"

(xi) SEQUENCE DESCRIPTION: SEQ ID NO:50:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Glu Ile Leu Asp Val Pro Ser
        35                  40                  45

Thr Cys Xaa Xaa Xaa Xaa Xaa Xaa Xaa Xaa Xaa Xaa Xaa Xaa Xaa
    50                  55                  60

Xaa Xaa Xaa Xaa Xaa Xaa
65                  70

(2) INFORMATION FOR SEQ ID NO:51:

(i) SEQUENCE CHARACTERISTICS:
        (A) LENGTH: 70 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 70
        (D) OTHER INFORMATION: /product= "OTHER"
            /note= "CYS AT POSITION 70 CAN BE ABSENT"

(xi) SEQUENCE DESCRIPTION: SEQ ID NO:51:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Cys Glu Ile Leu Asp Val Pro Ser
        35                  40                  45

Thr Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Cys
65                  70
```

(2) INFORMATION FOR SEQ ID NO:52:

(i) SEQUENCE CHARACTERISTICS:
        (A) LENGTH: 70 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "CYS AT POSITION 1 CAN BE ABSENT"

(ix) FEATURE:
        (A) NAME/KEY: Modified-site
        (B) LOCATION: 2..21
        (D) OTHER INFORMATION: /product= "OTHER"
            /note= "Xaa AT POSITIONS 2-21 CAN BE ANY AMINO ACIDS OR
            CAN BE ABSENT"

(ix) FEATURE:
        (A) NAME/KEY: Modified-site
        (B) LOCATION: 30
        (D) OTHER INFORMATION: /product= "OTHER"
            /note= "CYS AT POSITION 30 CAN BE ABSENT"

(ix) FEATURE:
        (A) NAME/KEY: Modified-site
        (B) LOCATION: 31..50
        (D) OTHER INFORMATION: /product= "OTHER"
            /note= "Xaa AT POSITIONS 31-50 CAN BE ANY AMINO ACIDS OR
            CAN BE ABSENT"

(ix) FEATURE:
        (A) NAME/KEY: Modified-site
        (B) LOCATION: 51..70
        (D) OTHER INFORMATION: /product= "OTHER"
            /note= "Xaa AT POSITIONS 51-70 AN BE ANY CATIONIC AMINO
            ACIDS OR CAN BE AB..."

(xi) SEQUENCE DESCRIPTION: SEQ ID NO:52:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Glu Ile Leu Asp Val Pro Ser Thr Cys Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
65                  70

(2) INFORMATION FOR SEQ ID NO:53:

(i) SEQUENCE CHARACTERISTICS:
        (A) LENGTH: 70 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 30
        (D) OTHER INFORMATION: /product= "OTHER"
            /note= "CYS AT POSITION 50 CAN BE ABSENT"

(ix) FEATURE:
        (A) NAME/KEY: Modified-site
        (B) LOCATION: 31..50
        (D) OTHER INFORMATION: /product= "OTHER"
            /note= "Xaa AT POSITIONS 31-50 CAN BE ANY AMINO ACIDS OR

```
                    CAN BE ABSENT"

(ix) FEATURE:
            (A) NAME/KEY: Modified-site
            (B) LOCATION: 51..70
            (D) OTHER INFORMATION: /product= "OTHER"
                /note= "Xaa AT POSITIONS 51-70 CAN BE ANY CATIONIC AMINO
                ACIDS OR CAN BE ABSENT"

(xi) SEQUENCE DESCRIPTION: SEQ ID NO:53:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Glu Ile Leu Asp Val Pro Ser Thr Cys Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
65                  70

(2) INFORMATION FOR SEQ ID NO:54:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:54:

Lys Phe Thr Ile Val Phe
1               5

(2) INFORMATION FOR SEQ ID NO:55:

(i) SEQUENCE CHARACTERISTICS:
            (A) LENGTH: 48 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "CYS AT POSITION 1 CAN BE ABSENT"

(ix) FEATURE:
            (A) NAME/KEY: Modified-site
            (B) LOCATION: 2..21
            (D) OTHER INFORMATION: /product= "OTHER"
                /note= "Xaa AT POSITIONS 2-21 CAN BE ANY AMINO ACIDS OR
                CAN BE ABSENT"

(ix) FEATURE:
            (A) NAME/KEY: Modified-site
            (B) LOCATION: 28..47
            (D) OTHER INFORMATION: /product= "OTHER"
                /note= "Xaa AT POSITIONS 28-47 CAN BE ANY AMINO ACIDS OR
                CAN BE ABSENT"

(ix) FEATURE:
            (A) NAME/KEY: Modified-site
            (B) LOCATION: 48
            (D) OTHER INFORMATION: /product= "OTHER"
                /note= "CYS AT POSITION 48 CAN BE ABSENT"
```

(xi) SEQUENCE DESCRIPTION: SEQ ID NO:55:

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Lys Phe Thr Ile Val Phe Xaa Xaa Xaa Xaa Xaa
                20                  25                  30

Xaa Xaa Xaa Xaa Xaa Xaa Xaa Xaa Xaa Xaa Xaa Xaa Xaa Xaa Cys
        35                  40                  45

(2) INFORMATION FOR SEQ ID NO:56:

(i) SEQUENCE CHARACTERISTICS:
        (A) LENGTH: 68 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY CATIONIC AMINO
            ACIDS OR CAN BE AB..."

(ix) FEATURE:
        (A) NAME/KEY: Modified-site
        (B) LOCATION: 21..40
        (D) OTHER INFORMATION: /product= "OTHER"
            /note= "Xaa AT POSITIONS 21-40 CAN BE ANY AMINO ACIDS OR
            CAN BE ABSENT"

(ix) FEATURE:
        (A) NAME/KEY: Modified-site
        (B) LOCATION: 41
        (D) OTHER INFORMATION: /product= "OTHER"
            /note= "CYS AT POSITION 41 CAN BE ABSENT"

(ix) FEATURE:
        (A) NAME/KEY: Modified-site
        (B) LOCATION: 48
        (D) OTHER INFORMATION: /product= "OTHER"
            /note= "CYS AT POSITION 48 CAN BE ABSENT"

(ix) FEATURE:
        (A) NAME/KEY: Modified-site
        (B) LOCATION: 49..68
        (D) OTHER INFORMATION: /product= "OTHER"
            /note= "Xaa AT POSITIONS 49-68 CAN BE ANY AMINO ACIDS OR
            CAN BE ABSENT"

(xi) SEQUENCE DESCRIPTION: SEQ ID NO:56:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Cys Lys Phe Thr Ile Val Phe Cys
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa
65

(2) INFORMATION FOR SEQ ID NO:57:

(i) SEQUENCE CHARACTERISTICS:
        (A) LENGTH: 68 amino acids
        (B) TYPE: amino acid
        (C) STRANDEDNESS: Not Relevant (D) TOPOLOGY: linear (ii) MOLECULE TYPE: peptide (ix) FEATURE:
                (A) NAME/KEY: Modified-site
                (B) LOCATION: 1..20
                (D) OTHER INFORMATION: /product= "OTHER"
                    /note= "Xaa AT POSITIONS 1-20 CAN BE ANY CATIONIC AMINO
                    ACID OR CAN BE ABSENT"

(ix) FEATURE:
                (A) NAME/KEY: Modified-site
                (B) LOCATION: 21..40
                (D) OTHER INFORMATION: /product= "OTHER"
                    /note= "Xaa AT POSITIONS 21-40 CAN BE ANY AMINO ACIDS OR
                    CAN BE ABSENT"

(ix) FEATURE:
                (A) NAME/KEY: Modified-site
                (B) LOCATION: 41
                (D) OTHER INFORMATION: /product= "OTHER"
                    /note= "CYS AT POSITION 41 CAN BE ABSENT"

(ix) FEATURE:
                (A) NAME/KEY: Modified-site
                (B) LOCATION: 48..67
                (D) OTHER INFORMATION: /product= "OTHER"
                    /note= "Xaa AT POSITIONS 48-67 CAN BE ANY AMINO ACIDS OR
                    CAN BE ABSENT"

(ix) FEATURE:
                (A) NAME/KEY: Modified-site
                (B) LOCATION: 68
                (D) OTHER INFORMATION: /product= "OTHER"
                    /note= "CYS AT POSITION 68 CAN BE ABSENT"

(xi) SEQUENCE DESCRIPTION: SEQ ID NO:57:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Lys Phe Thr Ile Val Phe Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Cys
65

(2) INFORMATION FOR SEQ ID NO:58:

(i) SEQUENCE CHARACTERISTICS:
                (A) LENGTH: 68 amino acids
                (B) TYPE: amino acid
                (C) STRANDEDNESS: Not Relevant
                (D) TOPOLOGY: linear (ii) MOLECULE TYPE: peptide (ix) FEATURE:
                (A) NAME/KEY: Modified-site
                (B) LOCATION: 1
                (D) OTHER INFORMATION: /product= "OTHER"
                    /note= "CYS AT POSITION 1 CAN BE ABSENT"

(ix) FEATURE:
                (A) NAME/KEY: Modified-site
                (B) LOCATION: 2..21
                (D) OTHER INFORMATION: /product= "OTHER"
                    /note= "Xaa AT POSITIONS 2-21 CAN BE ANY AMINO ACIDS OR
                    CAN BE ABSENT"

(ix) FEATURE:

(A) NAME/KEY: Modified-site
              (B) LOCATION: 28
              (D) OTHER INFORMATION: /product= "OTHER"
                  /note= "CYS AT POSITION 28 CAN BE ABSENT"

(ix) FEATURE:
              (A) NAME/KEY: Modified-site
              (B) LOCATION: 29..48
              (D) OTHER INFORMATION: /product= "OTHER"
                  /note= "Xaa AT POSITIONS 29-48 CAN BE ANY AMNINO ACIDS OR
                  CAN BE ABSENT"

(ix) FEATURE:
              (A) NAME/KEY: Modified-site
              (B) LOCATION: 49..68
              (D) OTHER INFORMATION: /product= "OTHER"
                  /note= "Xaa AT POSITIONS 49-68 CAN BE ANY CATIONIC AMINO
                  ACIDS OR CAN BE ABSENT"

(xi) SEQUENCE DESCRIPTION: SEQ ID NO:58:

Cys Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa
65

(2) INFORMATION FOR SEQ ID NO:59:

(i) SEQUENCE CHARACTERISTICS:
              (A) LENGTH: 68 amino acids
              (B) TYPE: amino acid
              (C) STRANDEDNESS: Not Relevant
              (D) TOPOLOGY: linear (ii) MOLECULE TYPE: peptide (ix) FEATURE:
              (A) NAME/KEY: Modified-site
              (B) LOCATION: 1..20
              (D) OTHER INFORMATION: /product= "OTHER"
                  /note= "Xaa AT POSITIONS 1-20 CAN BE ANY AMINO ACIDS OR
                  CAN BE ABSENT"

(ix) FEATURE:
              (A) NAME/KEY: Modified-site
              (B) LOCATION: 21
              (D) OTHER INFORMATION: /product= "OTHER"
                  /note= "CYS AT POSITION 21 CAN BE ABSENT"

(ix) FEATURE:
              (A) NAME/KEY: Modified-site
              (B) LOCATION: 28
              (D) OTHER INFORMATION: /product= "OTHER"
                  /note= "CYS AT POSITION 28 CAN BE ABSENT"

(ix) FEATURE:
              (A) NAME/KEY: Modified-site
              (B) LOCATION: 29..48
              (D) OTHER INFORMATION: /product= "OTHER"
                  /note= "Xaa AT POSITIONS 29-48 CAN BE ANY AMINO ACIDS OR
                  CAN BE ABSENT"

(ix) FEATURE:
              (A) NAME/KEY: Modified-site
              (B) LOCATION: 49..68
              (D) OTHER INFORMATION: /product= "OTHER"
                  /note= "Xaa AT POSITIONS 49-68 CAN BE ANY CATIONIC AMINO
                  ACIDS OR CAN BE ABSENT"

(xi) SEQUENCE DESCRIPTION: SEQ ID NO:59:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa Xaa
                20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa
65

(2) INFORMATION FOR SEQ ID NO:60:

(i) SEQUENCE CHARACTERISTICS:
        (A) LENGTH: 95 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR OR TRP OR CAN BE
            ABSENT"

(ix) FEATURE:
        (A) NAME/KEY: Modified-site
        (B) LOCATION: 23..42
        (D) OTHER INFORMATION: /product= "OTHER"
            /note= "Xaa AT POSITIONS 23-42 ANC BE ANY AMINO ACIDS OR
            CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 75
        (D) OTHER INFORMATION: /product= "OTHER"
            /note= "CYS AT POSITION 75 CAN BE ABSENT"

(ix) FEATURE:
        (A) NAME/KEY: Modified-site
        (B) LOCATION: 76..95
        (D) OTHER INFORMATION: /product= "OTHER"
            /note= "Xaa AT POSITIONS 76-95 CAN BE ANY AMINO ACIDS OR
            CAN BE ABSENT"

(xi) SEQUENCE DESCRIPTION: SEQ ID NO:60:

Xaa Xaa Xaa Xaa Xaa Xaa Xaa Xaa Xaa Xaa Xaa Xaa Xaa Xaa Xaa Xaa

```
   1               5                  10                  15
Xaa Xaa Xaa Xaa Cys Xaa Xaa Xaa Xaa Xaa Xaa Xaa Xaa Xaa
               20                  25                  30

Xaa Xaa Xaa Xaa Xaa Xaa Xaa Xaa Xaa Pro Lys Lys Arg Lys
       35                  40                  45

Val Xaa Xaa Xaa Xaa Xaa Xaa Xaa Xaa Xaa Xaa Xaa Xaa Xaa
   50                  55                  60

Xaa Xaa Xaa Xaa Xaa Arg Gly Asp Met Phe Cys Xaa Xaa Xaa Xaa Xaa
 65                  70                  75                  80

Xaa Xaa Xaa Xaa Xaa Xaa Xaa Xaa Xaa Xaa Xaa Xaa Xaa Xaa
               85                  90                  95
```

(2) INFORMATION FOR SEQ ID NO:61:

(i) SEQUENCE CHARACTERISTICS:
        (A) LENGTH: 95 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22..41
        (D) OTHER INFORMATION: /product= "OTHER"
            /note= "Xaa AT POSITIONS 22-41 CAN BE ANY AMINO ACIDS OR CAN BE ABSENT"

(ix) FEATURE:
        (A) NAME/KEY: Modified-site
        (B) LOCATION: 42
        (D) OTHER INFORMATION: /product= "OTHER"
            /note= "Xaa AT POSITION 42 CAN BE TYR OR TRP OR CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR CAN BE ABSENT"

(ix) FEATURE:
        (A) NAME/KEY: Modified-site
        (B) LOCATION: 75
        (D) OTHER INFORMATION: /product= "OTHER"
            /note= "CYS AT POSITION 75 CAN BE ABSENT"

(ix) FEATURE:
        (A) NAME/KEY: Modified-site
        (B) LOCATION: 76..95
        (D) OTHER INFORMATION: /product= "OTHER"
            /note= "Xaa AT POSITIONS 76-95 CAN BE ANY AMINO ACIDS OR CAN BE ABSENT"

(xi) SEQUENCE DESCRIPTION: SEQ ID NO:61:

```
Xaa Xaa Xaa Xaa Xaa Xaa Xaa Xaa Xaa Xaa Xaa Xaa Xaa Xaa Xaa Xaa
 1               5                  10                  15
```

```
Xaa Xaa Xaa Xaa Cys Xaa Xaa Xaa Xaa Xaa Xaa Xaa Xaa Xaa
            20              25                  30

Xaa Xaa Xaa Xaa Xaa Xaa Xaa Xaa Xaa Pro Lys Lys Arg Lys
        35              40              45

Val Xaa Xaa Xaa Xaa Xaa Xaa Xaa Xaa Xaa Xaa Xaa Xaa Xaa
    50              55              60

Xaa Xaa Xaa Xaa Xaa Arg Gly Asp Met Phe Cys Xaa Xaa Xaa Xaa
65              70              75                      80

Xaa Xaa Xaa Xaa Xaa Xaa Xaa Xaa Xaa Xaa Xaa Xaa Xaa Xaa Xaa
            85              90                  95
```

(2) INFORMATION FOR SEQ ID NO:62:

(i) SEQUENCE CHARACTERISTICS:
        (A) LENGTH: 96 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
        CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR OR TRP OR CAN BE
        ABSENT"

(ix) FEATURE:
        (A) NAME/KEY: Modified-site
        (B) LOCATION: 23..42
        (D) OTHER INFORMATION: /product= "OTHER"
            /note= "Xaa AT POSITIONS 23-42 CAN BE ANY AMINO ACIDS OR
        CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OF
        CAN BE1 ABSENT"

(ix) FEATURE:
        (A) NAME/KEY: Modified-site
        (B) LOCATION: 76
        (D) OTHER INFORMATION: /product= "OTHER"
            /note= "CYS AT POSITION 76 CAN BE ABSENT"

(ix) FEATURE:
        (A) NAME/KEY: Modified-site
        (B) LOCATION: 77..96
        (D) OTHER INFORMATION: /product= "OTHER"
            /note= "Xaa AT POSITIONS 77-96 CAN BE ANY AMINO ACIDS OR
        CAN BE ABSENT"

(xi) SEQUENCE DESCRIPTION: SEQ ID NO:62:

```
Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Cys Xaa Xaa Xaa Xaa Xaa Xaa Xaa Xaa Xaa Xaa
            20              25              30

Xaa Xaa Xaa Xaa Xaa Xaa Xaa Xaa Xaa Xaa Pro Lys Lys Lys Arg Lys
        35                  40                  45

Val Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Gly Arg Gly Asp Ser Pro Cys Xaa Xaa Xaa Xaa
65              70                  75                  80

Xaa Xaa Xaa Xaa Xaa Xaa Xaa Xaa Xaa Xaa Xaa Xaa Xaa Xaa Xaa
            85                  90                  95
```

(2) INFORMATION FOR SEQ ID NO:63:

(i) SEQUENCE CHARACTERISTICS:
        (A) LENGTH: 95 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACID OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR OR TRP OR CAN BE
            ABSENT"

(ix) FEATURE:
        (A) NAME/KEY: Modified-site
        (B) LOCATION: 23..42
        (D) OTHER INFORMATION: /product= "OTHER"
            /note= "Xaa AT POSITION 23-42 CAN BE ANY AMINO ACIDS OR
            CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 75
        (D) OTHER INFORMATION: /product= "OTHER"
            /note= "CYS AT POSITION 75 CAN BE ABSENT"

(ix) FEATURE:
        (A) NAME/KEY: Modified-site
        (B) LOCATION: 76..95
        (D) OTHER INFORMATION: /product= "OTHER"
            /note= "Xaa AT POSITIONS 76-95 CAN BE ANY AMINO ACIDS OR
            CAN BE ABSENT"

(xi) SEQUENCE DESCRIPTION: SEQ ID NO:63:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa
```

```
                     20                  25                  30
Xaa Xaa Xaa Xaa Xaa Xaa Xaa Xaa Xaa Pro Lys Lys Lys Arg Lys
             35                  40                  45

Val Xaa Xaa Xaa Xaa Xaa Xaa Xaa Xaa Xaa Xaa Xaa Xaa Xaa Xaa
     50                  55                  60

Xaa Xaa Xaa Xaa Xaa Arg Gly Asp Ser Pro Cys Xaa Xaa Xaa Xaa
 65                  70                  75                  80

Xaa Xaa Xaa Xaa Xaa Xaa Xaa Xaa Xaa Xaa Xaa Xaa Xaa Xaa
             85                  90                  95
```

(2) INFORMATION FOR SEQ ID NO:64:

(i) SEQUENCE CHARACTERISTICS:
        (A) LENGTH: 117 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACID OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 28
        (D) OTHER INFORMATION: /product= "OTHER"
            /note= "CYS AT POSITION 28 CAN BE ABSENT"

(ix) FEATURE:
        (A) NAME/KEY: Modified-site
        (B) LOCATION: 29..48
        (D) OTHER INFORMATION: /product= "OTHER"
            /note= "Xaa AT POSITIONS 29-48 CAN BE ANY AMINO ACIDS OR
            CAN BE ABSENT"

(ix) FEATURE:
        (A) NAME/KEY: Modified-site
        (B) LOCATION: 49
        (D) OTHER INFORMATION: /product= "OTHER"
            /note= "CYS AT POSITION 49 CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACIDS OR
            CAN BE ABSENT"

(ix) FEATURE:
        (A) NAME/KEY: Modified-site
        (B) LOCATION: 70
        (D) OTHER INFORMATION: /product= "OTHER"
            /note= "Xaa AT POSITION 70 CAN BE TYR OR TRP OR CAN BE
            ABSENT"

(ix) FEATURE:
        (A) NAME/KEY: Modified-site
        (B) LOCATION: 71..90
        (D) OTHER INFORMATION: /product= "OTHER"
            /note= "Xaa AT POSITIONS 71-90 CAN BE ANY AMINO ACIDS OR
            CAN BE ABSENT"

(ix) FEATURE:

(A) NAME/KEY: Modified-site
            (B) LOCATION: 98..117
            (D) OTHER INFORMATION: /product= "OTHER"
                /note= "Xaa AT POSITIONS 98-117 CAN BE ANY AMINO ACIDS OR
                CAN BE ABSENT"

(xi) SEQUENCE DESCRIPTION: SEQ ID NO:64:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Cys Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Pro Lys Lys Lys Arg Lys
            85                  90                  95

Val Xaa Xaa Xaa Xaa Xaa Xaa Xaa Xaa Xaa Xaa Xaa Xaa Xaa Xaa
            100                 105                 110

Xaa Xaa Xaa Xaa Xaa
        115

(2) INFORMATION FOR SEQ ID NO:65:

(i) SEQUENCE CHARACTERISTICS:
        (A) LENGTH: 97 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 28
        (D) OTHER INFORMATION: /product= "OTHER"
            /note= "CYS AT POSITION 28 CAN BE ABSENT"

(ix) FEATURE:
        (A) NAME/KEY: Modified-site
        (B) LOCATION: 29..48
        (D) OTHER INFORMATION: /product= "OTHER"
            /note= "Xaa AT POSITIONS 29-48 CAN BE ANY AMINO ACIDS OR
            CAN BE ABSENT"

(ix) FEATURE:
        (A) NAME/KEY: Modified-site
        (B) LOCATION: 49
        (D) OTHER INFORMATION: /product= "OTHER"
            /note= "CYS AT POSITION 49 CAN BE ABSENT"

(ix) FEATURE:
        (A) NAME/KEY: Modified-site
        (B) LOCATION: 50..69
        (D) OTHER INFORMATION: /product= "OTHER"

/note= "Xaa AT POSITIONS 50-69 CAN BE ANY AMINO ACIDS OR
CAN BE ABSENT"

(ix) FEATURE:
    (A) NAME/KEY: Modified-site
    (B) LOCATION: 70
    (D) OTHER INFORMATION: /product= "OTHER"
        /note= "Xaa AT POSITION 70 CAN BE TYR OR TRP OR CAN BE
        ABSENT"

(ix) FEATURE:
    (A) NAME/KEY: Modified-site
    (B) LOCATION: 78..97
    (D) OTHER INFORMATION: /product= "OTHER"
        /note= "Xaa AT POSITIONS 78-97 CAN BE ANY AMINO ACIDS OR
        CAN BE ABSENT"

(xi) SEQUENCE DESCRIPTION: SEQ ID NO:65:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Cys Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Pro Lys Lys Lys Arg Lys Val Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa
```

(2) INFORMATION FOR SEQ ID NO:66:

(i) SEQUENCE CHARACTERISTICS:
        (A) LENGTH: 99 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22
        (D) OTHER INFORMATION: /product= "OTHER"
            /note= "Xaa AT POSITION 22 CAN BE TYR, TRP OR CAN BE
            ABSENT"

(ix) FEATURE:
        (A) NAME/KEY: Modified-site
        (B) LOCATION: 23..42
        (D) OTHER INFORMATION: /product= "OTHER"
            /note= "Xaa AT POSITIONS 23-42 CAN BE ANY AMINO ACIDS OR
            CAN BE ABSENT"

(ix) FEATURE:
        (A) NAME/KEY: Modified-site

-continued (B) LOCATION: 51..70
            (D) OTHER INFORMATION: /product= "OTHER"
                /note= "Xaa AT POSITIONS 51-70 CAN BE ANY AMINO ACIDS OR
                CAN BE ABSENT"

(ix) FEATURE:
            (A) NAME/KEY: Modified-site
            (B) LOCATION: 79
            (D) OTHER INFORMATION: /product= "OTHER"
                /note= "CYS AT POSITION 79 CAN BE ABSENT"

(ix) FEATURE:
            (A) NAME/KEY: Modified-site
            (B) LOCATION: 80..99
            (D) OTHER INFORMATION: /product= "OTHER"
                /note= "Xaa FROM 80-99 CAN BE ANY AMINO ACIDS OR CAN BE
                ABSENT"

(xi) SEQUENCE DESCRIPTION: SEQ ID NO:66:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa
            20                  25                  30

Xaa Xaa Xaa Xaa Xaa Xaa Xaa Xaa Xaa Gly Pro Lys Lys Lys Arg
        35                  40                  45

Lys Val Xaa Xaa Xaa Xaa Xaa Xaa Xaa Xaa Xaa Xaa Xaa Xaa Xaa
    50                  55                  60

Xaa Xaa Xaa Xaa Xaa Xaa Glu Ile Leu Asp Val Ser Pro Thr Cys Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa (2) INFORMATION FOR SEQ ID NO:67:

(i) SEQUENCE CHARACTERISTICS:
            (A) LENGTH: 78 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                /note= "Xaa FROM 1-20 CAN BE ANY AMINO ACIDS OR CAN BE
                ABSENT"

(ix) FEATURE:
            (A) NAME/KEY: Modified-site
            (B) LOCATION: 21
            (D) OTHER INFORMATION: /product= "OTHER"
                /note= "CYS AT POSITION 21 CAN BE ABSENT"

(ix) FEATURE:
            (A) NAME/KEY: Modified-site
            (B) LOCATION: 22
            (D) OTHER INFORMATION: /product= "OTHER"
                /note= "Xaa AT POSITION 22 CAN BE TYR, TRP OR CAN BE
                ABSENT"

(ix) FEATURE:
            (A) NAME/KEY: Modified-site
            (B) LOCATION: 30..49
            (D) OTHER INFORMATION: /product= "OTHER"
                /note= "Xaa AT POSITIONS 30-49 CAN BE ANY AMINO ACIDS OR
                CAN BE ABSENT"

(ix) FEATURE:

(A) NAME/KEY: Modified-site
            (B) LOCATION: 58
            (D) OTHER INFORMATION: /product= "OTHER"
                /note= "CYS AT POSITION 58 CAN BE ABSENT"

(ix) FEATURE:
            (A) NAME/KEY: Modified-site
            (B) LOCATION: 59..78
            (D) OTHER INFORMATION: /product= "OTHER"
                /note= "Xaa AT POSITIONS 59-78 CAN BE ANY AMINO ACIDS OR
                CAN BE ABSENT"

(xi) SEQUENCE DESCRIPTION: SEQ ID NO:67:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Pro Lys Lys Lys Arg Lys Val Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Glu Ile Leu Asp Val Ser Pro Thr Cys Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa
65                  70                  75

(2) INFORMATION FOR SEQ ID NO:68:

(i) SEQUENCE CHARACTERISTICS:
            (A) LENGTH: 77 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                /note= "Xaa AT POSITIONS 1-20 CAN BE ANY AMINO ACID OR
                CAN BE ABSENT"

(ix) FEATURE:
            (A) NAME/KEY: Modified-site
            (B) LOCATION: 21
            (D) OTHER INFORMATION: /product= "OTHER"
                /note= "CYS AT POSITION 21 CAN BE ABSENT"

(ix) FEATURE:
            (A) NAME/KEY: Modified-site
            (B) LOCATION: 28
            (D) OTHER INFORMATION: /product= "OTHER"
                /note= "CYS AT POSITION 28 CAN BE ABSENT"

(ix) FEATURE:
            (A) NAME/KEY: Modified-site
            (B) LOCATION: 29..48
            (D) OTHER INFORMATION: /product= "OTHER"
                /note= "Xaa AT POSITION 29-48 CAN BE ANY AMINO ACID OR
                CAN BE ABSENT"

(ix) FEATURE:
            (A) NAME/KEY: Modified-site
            (B) LOCATION: 57
            (D) OTHER INFORMATION: /product= "OTHER"
                /note= "CYS AT POSITION 57 CAN BE ABSENT"

(ix) FEATURE:
            (A) NAME/KEY: Modified-site
            (B) LOCATION: 58..77
            (D) OTHER INFORMATION: /product= "OTHER"
                /note= "Xaa AT POSITIONS 58-77 CAN BE ANY AMINO ACIDS OR
                CAN BE ABSENT"

(xi) SEQUENCE DESCRIPTION: SEQ ID NO:68:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa
                20                  25                  30

Xaa Xaa Xaa Xaa Xaa Xaa Xaa Xaa Xaa Xaa Xaa Xaa Xaa Xaa Xaa
                35                  40                  45

Glu Ile Leu Asp Val Pro Ser Thr Cys Xaa Xaa Xaa Xaa Xaa Xaa
            50                  55                  60

Xaa Xaa Xaa Xaa Xaa Xaa Xaa Xaa Xaa Xaa Xaa Xaa
65                  70                  75

(2) INFORMATION FOR SEQ ID NO:69:

(i) SEQUENCE CHARACTERISTICS:
      (A) LENGTH: 93 amino acids
      (B) TYPE: amino acid
      (C) STRANDEDNESS: Not Relevant
      (D) TOPOLOGY: linear (ii) MOLECULE TYPE: peptide (ix) FEATURE:
      (A) NAME/KEY: Modified-site
      (B) LOCATION: 1..20
      (D) OTHER INFORMATION: /product= "OTHER"
          /note= "Xaa AT POSITIONS 1-20 CAN BE ANY AMINO ACIDS OR
          CAN BE ABSENT"

(ix) FEATURE:
      (A) NAME/KEY: Modified-site
      (B) LOCATION: 21
      (D) OTHER INFORMATION: /product= "OTHER"
          /note= "Xaa AT POSITION 21 CAN BE TYR, TRP OR CAN BE
          ABSENT"

(ix) FEATURE:
      (A) NAME/KEY: Modified-site
      (B) LOCATION: 22..41
      (D) OTHER INFORMATION: /product= "OTHER"
          /note= "Xaa AT POSITIONS 22-41 CAN BE ANY AMINO ACIDS OR
          CAN BE ABSENT"

(ix) FEATURE:
      (A) NAME/KEY: Modified-site
      (B) LOCATION: 49..68
      (D) OTHER INFORMATION: /product= "OTHER"
          /note= "Xaa AT POSITIONS 49-68 CAN BE ANY AMINO ACIDS OR
          CAN BE ABSENT"

(ix) FEATURE:
      (A) NAME/KEY: Modified-site
      (B) LOCATION: 74..93
      (D) OTHER INFORMATION: /product= "OTHER"
          /note= "Xaa AT POSITIONS 74-93 CAN BE ANY AMINO ACIDS OR
          CAN BE ABSENT"

(xi) SEQUENCE DESCRIPTION: SEQ ID NO:69:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Pro Lys Lys Arg Lys Val
                35                  40                  45

Xaa Xaa Xaa Xaa Xaa Xaa Xaa Xaa Xaa Xaa Xaa Xaa Xaa Xaa Xaa
                50                  55                  60

Xaa Xaa Xaa Xaa Arg Gly Asp Met Phe Xaa Xaa Xaa Xaa Xaa Xaa Xaa
65                  70                  75                  80

```
Xaa Xaa Xaa Xaa Xaa Xaa Xaa Xaa Xaa Xaa Xaa Xaa Xaa
                85                  90
```

(2) INFORMATION FOR SEQ ID NO:70:

(i) SEQUENCE CHARACTERISTICS:
        (A) LENGTH: 94 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa AT POSITIONS 1-20 CAN BE ANY AMINO ACIDS OR
            CAN BE ABSENT"

(ix) FEATURE:
        (A) NAME/KEY: Modified-site
        (B) LOCATION: 21
        (D) OTHER INFORMATION: /product= "OTHER"
            /note= "CYS AT POSITION 21 CAN BE ABSENT"

(ix) FEATURE:
        (A) NAME/KEY: Modified-site
        (B) LOCATION: 22..41
        (D) OTHER INFORMATION: /product= "OTHER"
            /note= "Xaa AT POSITIONS 22-41 CAN BE ANY AMINO ACIDS OR
            CAN BE ABSENT"

(ix) FEATURE:
        (A) NAME/KEY: Modified-site
        (B) LOCATION: 42
        (D) OTHER INFORMATION: /product= "OTHER"
            /note= "Xaa AT POSITION 42 CAN BE ANY AMINO ACID OR CAN
            BE ABSENT"

(ix) FEATURE:
        (A) NAME/KEY: Modified-site
        (B) LOCATION: 50..69
        (D) OTHER INFORMATION: /product= "OTHER"
            /note= "Xaa AT POSITIONS 50-69 CAN BE ANY AMINO ACID OR
            CAN BE ABSENT"

(ix) FEATURE:
        (A) NAME/KEY: Modified-site
        (B) LOCATION: 75..94
        (D) OTHER INFORMATION: /product= "OTHER"
            /note= "Xaa AT POSITIONS 75-94 CAN BE ANY AMINO ACIDS OR
            CAN BE ABSENT"

(xi) SEQUENCE DESCRIPTION: SEQ ID NO:70:

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Pro Lys Lys Lys Arg Lys
            35                  40                  45

Val Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Arg Gly Asp Met Phe Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90
```

(2) INFORMATION FOR SEQ ID NO:71:

(i) SEQUENCE CHARACTERISTICS:
            (A) LENGTH: 94 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                /note= "Xaa CAN BE ANY AMINO ACID OR CAN BE ABSENT"

(ix) FEATURE:
            (A) NAME/KEY: Modified-site
            (B) LOCATION: 21
            (D) OTHER INFORMATION: /product= "OTHER"
                /note= "Xaa CAN BE TYR, TRP OR CAN BE ABSENT"

(ix) FEATURE:
            (A) NAME/KEY: Modified-site
            (B) LOCATION: 22..41
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site
            (B) LOCATION: 49..68
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site
            (B) LOCATION: 75..94
            (D) OTHER INFORMATION: /product= "OTHER"
                /note= "Xaa CAN BE ANY AMINO ACIDS OR CAN BE ABSENT"

(xi) SEQUENCE DESCRIPTION: SEQ ID NO:71:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Pro Lys Lys Lys Arg Lys Val
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Gly Arg Gly Asp Ser Pro Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
            85                  90

(2) INFORMATION FOR SEQ ID NO:72:

(i) SEQUENCE CHARACTERISTICS:
            (A) LENGTH: 94 amino acids
            (B) TYPE: amino acid
            (C) STRANDEDNESS: Not Relevant
            (D) TOPOLOGY: linear (ii) MOLECULE TYPE: peptide (ix) FEATURE:
            (A) NAME/KEY: Modified-site
            (B) LOCATION: 1..20
            (D) OTHER INFORMATION: /product= "OTHER"
                /note= "Xaa CAN BE ANY AMINO ACIDS OR CAN BE ABSENT"

(ix) FEATURE:
            (A) NAME/KEY: Modified-site
            (B) LOCATION: 21
            (D) OTHER INFORMATION: /product= "OTHER"

/note= "CYS CAN BE ABSENT"

(ix) FEATURE:
        (A) NAME/KEY: Modified-site
        (B) LOCATION: 22
        (D) OTHER INFORMATION: /product= "OTHER"
            /note= "Xaa CAN BE TYR, TRP OR CAN BE ABSENT"

(ix) FEATURE:
        (A) NAME/KEY: Modified-site
        (B) LOCATION: 23..42
        (D) OTHER INFORMATION: /product= "OTHER"
            /note= "Xaa CAN BE ANY AMINO ACIDS OR CAN BE ABSENT"

(ix) FEATURE:
        (A) NAME/KEY: Modified-site
        (B) LOCATION: 50..69
        (D) OTHER INFORMATION: /product= "OTHER"
            /note= "Xaa CAN BE ANY AMINO ACIDS OR CAN BE ABSENT"

(ix) FEATURE:
        (A) NAME/KEY: Modified-site
        (B) LOCATION: 75..94
        (D) OTHER INFORMATION: /product= "OTHER"
            /note= "Xaa CAN BE ANY AMINO ACIDS OR CAN BE ABSENT"

(xi) SEQUENCE DESCRIPTION: SEQ ID NO:72:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Pro Lys Lys Lys Arg Lys
            35                  40                  45

Val Xaa Xaa Xaa Xaa Xaa Xaa Xaa Xaa Xaa Xaa Xaa Xaa Xaa Xaa
    50                  55                  60

Xaa Xaa Xaa Xaa Xaa Arg Gly Asp Ser Pro Xaa Xaa Xaa Xaa Xaa
65                  70                  75                  80

Xaa Xaa Xaa Xaa Xaa Xaa Xaa Xaa Xaa Xaa Xaa Xaa Xaa Xaa
                85                  90

(2) INFORMATION FOR SEQ ID NO:73:

(i) SEQUENCE CHARACTERISTICS:
        (A) LENGTH: 116 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "other"
            /note= "Xaa CAN BE ANY AMINO ACID OR CAN BE ABSENT"

(ix) FEATURE:
        (A) NAME/KEY: Modified-site
        (B) LOCATION: 27
        (D) OTHER INFORMATION: /product= "OTHER"
            /note= "CYS CAN BE ABSENT"

(ix) FEATURE:
        (A) NAME/KEY: Modified-site
        (B) LOCATION: 28..47
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 48
        (D) OTHER INFORMATION: /product= "OTHER"

-continued

```
                      /note= "CYS CAN BE ABSENT"

(ix) FEATURE:
                (A) NAME/KEY: Modified-site
                (B) LOCATION: 49..68
                (D) OTHER INFORMATION: /product= "OTHER"
                    /note= "Xaa CAN BE ANY AMINO ACID OR CAN BE ABSENT"

(ix) FEATURE:
                (A) NAME/KEY: Modified-site
                (B) LOCATION: 69
                (D) OTHER INFORMATION: /product= "OTHER"
                    /note= "Xaa AT POSITION 69 CAN BE TYR, TRP, OR CAN BE
                    ABSENT"

(ix) FEATURE:
                (A) NAME/KEY: Modified-site
                (B) LOCATION: 70..89
                (D) OTHER INFORMATION: /product= "OTHER"
                    /note= "Xaa CAN BE ANY AMINO ACIDS OR CAN BE ABSENT"

(ix) FEATURE:
                (A) NAME/KEY: Modified-site
                (B) LOCATION: 97..116
                (D) OTHER INFORMATION: /product= "OTHER"
                    /note= "Xaa CAN BE ANY AMINO ACID OR CAN BE ABSENT"

(xi) SEQUENCE DESCRIPTION: SEQ ID NO:73:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Lys Phe Thr Ile Val Phe Cys Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Cys
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Pro Lys Lys Lys Arg Lys Val
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa
        115

(2) INFORMATION FOR SEQ ID NO:74:

(i) SEQUENCE CHARACTERISTICS:
                (A) LENGTH: 97 amino acids
                (B) TYPE: amino acid
                (C) STRANDEDNESS: Not Relevant
                (D) TOPOLOGY: linear (ii) MOLECULE TYPE: peptide (ix) FEATURE:
                (A) NAME/KEY: Modified-site
                (B) LOCATION: 1..20
                (D) OTHER INFORMATION: /product= "OTHER"
                    /note= "Xaa CAN BE ANY AMINO ACID OR CAN BE ABSENT"

(ix) FEATURE:
                (A) NAME/KEY: Modified-site
                (B) LOCATION: 21
                (D) OTHER INFORMATION: /product= "OTHER"
                    /note= "CYS CAN BE ABSENT"

(ix) FEATURE:
                (A) NAME/KEY: Modified-site
                (B) LOCATION: 28
```

(D) OTHER INFORMATION: /product= "OTHER"
    /note= "CYS CAN BE ABSENT"

(ix) FEATURE:
    (A) NAME/KEY: Modified-site
    (B) LOCATION: 29..48
    (D) OTHER INFORMATION: /product= "OTHER"
        /note= "Xaa CAN BE ANY AMINO ACID OR CAN BE ABSENT"

(ix) FEATURE:
    (A) NAME/KEY: Active-site
    (B) LOCATION: 49
    (D) OTHER INFORMATION: /product= "OTHER"
        /note= "CYS CAN BE ABSENT"

(ix) FEATURE:
    (A) NAME/KEY: Modified-site
    (B) LOCATION: 50..69
    (D) OTHER INFORMATION: /product= "OTHER"
        /note= "Xaa CAN BE ANY AMINO ACID OR CAN BE ABSENT"

(ix) FEATURE:
    (A) NAME/KEY: Modified-site
    (B) LOCATION: 70
    (D) OTHER INFORMATION: /product= "OTHER"
        /note= "Xaa CAN BE TYR, TRP OR CAN BE ABSENT"

(ix) FEATURE:
    (A) NAME/KEY: Modified-site
    (B) LOCATION: 78..97
    (D) OTHER INFORMATION: /product= "OTHER"
        /note= "Xaa CAN BE ANY AMINO ACID OR CAN BE ABSENT"

(xi) SEQUENCE DESCRIPTION: SEQ ID NO:74:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Lys Phe Thr Ile Val Phe Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Cys Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Pro Lys Lys Lys Arg Lys Val Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa (2) INFORMATION FOR SEQ ID NO:75:

(i) SEQUENCE CHARACTERISTICS:
        (A) LENGTH: 97 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 21
        (D) OTHER INFORMATION: /product= "OTHER"
            /note= "Xaa CAN BE TYR, TRP OR CAN BE ABSENT"

(ix) FEATURE:

(A) NAME/KEY: Modified-site
                    (B) LOCATION: 22..41
                    (D) OTHER INFORMATION: /product= "other"
                        /note= "Xaa CAN BE ANY AMINO ACID OR CAN BE ABSENT"

(ix) FEATURE:
                    (A) NAME/KEY: Modified-site
                    (B) LOCATION: 50..69
                    (D) OTHER INFORMATION: /product= "OTHER"
                        /note= "Xaa CAN BE ANY AMINO ACID OR CAN BE ABSENT"

(ix) FEATURE:
                    (A) NAME/KEY: Modified-site
                    (B) LOCATION: 78..97
                    (D) OTHER INFORMATION: /product= "OTHER"
                        /note= "Xaa CAN BE ANY AMINO ACID OR CAN BE ABSENT"

(xi) SEQUENCE DESCRIPTION: SEQ ID NO:75:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Gly Pro Lys Lys Lys Arg Lys
            35                  40                  45

Val Xaa Xaa Xaa Xaa Xaa Xaa Xaa Xaa Xaa Xaa Xaa Xaa Xaa Xaa
50                  55                  60

Xaa Xaa Xaa Xaa Xaa Glu Ile Leu Asp Val Ser Pro Thr Xaa Xaa Xaa
65                  70                  75              80

Xaa Xaa Xaa Xaa Xaa Xaa Xaa Xaa Xaa Xaa Xaa Xaa Xaa Xaa Xaa
            85                  90                  95

Xaa (2) INFORMATION FOR SEQ ID NO:76:

(i) SEQUENCE CHARACTERISTICS:
                (A) LENGTH: 77 amino acids
                (B) TYPE: amino acid
                (C) STRANDEDNESS: Not Relevant
                (D) TOPOLOGY: linear (ii) MOLECULE TYPE: peptide (ix) FEATURE:
                (A) NAME/KEY: Modified-site
                (B) LOCATION: 1..20
                (D) OTHER INFORMATION: /product= "OTHER"
                    /note= "Xaa CAN BE ANY AMINO ACIDS OR CAN BE ABSENT"

(ix) FEATURE:
                (A) NAME/KEY: Modified-site
                (B) LOCATION: 21
                (D) OTHER INFORMATION: /product= "OTHER"
                    /note= "CYS CAN BE ABSENT"

(ix) FEATURE:
                (A) NAME/KEY: Modified-site
                (B) LOCATION: 22
                (D) OTHER INFORMATION: /product= "OTHER"
                    /note= "Xaa CAN BE TYR, TRP OR CAN BE ABSENT"

(ix) FEATURE:
                (A) NAME/KEY: Modified-site
                (B) LOCATION: 30..49
                (D) OTHER INFORMATION: /product= "OTHER"
                    /note= "Xaa CAN BE ANY AMINO ACID OR CAN BE ABSENT"

(ix) FEATURE:
                (A) NAME/KEY: Modified-site
                (B) LOCATION: 58..77
                (D) OTHER INFORMATION: /product= "OTHER"
                    /note= "Xaa CAN BE ANY AMINO ACID OR CAN BE ABSENT"

(xi) SEQUENCE DESCRIPTION: SEQ ID NO:76:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Cys Xaa Pro Lys Lys Arg Lys Val Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Glu Ile Leu Asp Val Ser Pro Thr Xaa Xaa Xaa Xaa Xaa Xaa
    50                  55                  60

Xaa Xaa Xaa Xaa Xaa Xaa Xaa Xaa Xaa Xaa Xaa Xaa Xaa
65                  70                  75

(2) INFORMATION FOR SEQ ID NO:77:

(i) SEQUENCE CHARACTERISTICS:
        (A) LENGTH: 75 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 27
        (D) OTHER INFORMATION: /product= "OTHER"
            /note= "CYS CAN BE ABSENT"

(ix) FEATURE:
        (A) NAME/KEY: Modified-site
        (B) LOCATION: 28..47
        (D) OTHER INFORMATION: /product= "OTHER"
            /note= "Xaa CAN BE ANY AMINO ACID AND CAN BE ABSENT"

(ix) FEATURE:
        (A) NAME/KEY: Modified-site
        (B) LOCATION: 56..75
        (D) OTHER INFORMATION: /product= "OTHER"
            /note= "Xaa CAN BE ANY AMINO ACID OR CAN BE ABSENT"

(xi) SEQUENCE DESCRIPTION: SEQ ID NO:77:

Xaa Xaa Xaa Xaa Xaa Xaa Xaa Xaa Xaa Xaa Xaa Xaa Xaa Xaa Xaa
1               5                   10                  15

Xaa Xaa Xaa Xaa Lys Phe Thr Ile Val Phe Cys Xaa Xaa Xaa Xaa
                20                  25                  30

Xaa Xaa Xaa Xaa Xaa Xaa Xaa Xaa Xaa Xaa Xaa Xaa Xaa Xaa Glu
            35                  40                  45

Ile Leu Asp Val Pro Ser Thr Xaa Xaa Xaa Xaa Xaa Xaa Xaa Xaa
    50                  55                  60

Xaa Xaa Xaa Xaa Xaa Xaa Xaa Xaa Xaa Xaa Xaa
65                  70                  75

(2) INFORMATION FOR SEQ ID NO:78:

(i) SEQUENCE CHARACTERISTICS:
        (A) LENGTH: 70 amino acids
        (B) TYPE: amino acid
        (C) STRANDEDNESS: Not Relevant
        (D) TOPOLOGY: circular (ii) MOLECULE TYPE: peptide (ix) FEATURE:
    (A) NAME/KEY: Modified-site
    (B) LOCATION: 1..20
    (D) OTHER INFORMATION: /product= "OTHER"
        /note= "Xaa CAN BE ANY CATIONIC AMINO ACIDS OR CAN BE
        ABSENT"

(ix) FEATURE:
    (A) NAME/KEY: Modified-site
    (B) LOCATION: 21..40
    (D) OTHER INFORMATION: /product= "OTHER"
        /note= "Xaa CAN BE ANY AMINO ACIDS OR CAN BE ABSENT"

(ix) FEATURE:
    (A) NAME/KEY: Modified-site
    (B) LOCATION: 51..70
    (D) OTHER INFORMATION: /product= "OTHER"
        /note= "Xaa CAN BE ANY AMINO ACIDS OR CAN BE ABSENT"

(xi) SEQUENCE DESCRIPTION: SEQ ID NO:78:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys Glu Ile Leu Asp Val Pro Ser
        35                  40                  45

Thr Cys Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa
65                  70

(2) INFORMATION FOR SEQ ID NO:79:

(i) SEQUENCE CHARACTERISTICS:
        (A) LENGTH: 71 amino acids
        (B) TYPE: amino acid
        (C) STRANDEDNESS: Not Relevant
        (D) TOPOLOGY: circular (ii) MOLECULE TYPE: peptide (ix) FEATURE:
        (A) NAME/KEY: Modified-site
        (B) LOCATION: 1..20
        (D) OTHER INFORMATION: /product= "OTHER"
            /note= "Xaa CAN BE ANY CATIONIC AMINO ACID OR CAN BE
            ABSENT"

(ix) FEATURE:
        (A) NAME/KEY: Modified-site
        (B) LOCATION: 21..40
        (D) OTHER INFORMATION: /product= "OTHER"
            /note= "Xaa CAN BE ANY AMINO ACID OR CAN BE ABSENT"

(ix) FEATURE:
        (A) NAME/KEY: Modified-site
        (B) LOCATION: 52..71
        (D) OTHER INFORMATION: /product= "OTHER"
            /note= "Xaa CAN BE ANY AMINO ACID OR CAN BE ABSENT"

(xi) SEQUENCE DESCRIPTION: SEQ ID NO:79:

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Cys His Ala Ile Arg Gly Asp Thr
        35                  40                  45

-continued

```
Phe Ala Cys Xaa Xaa Xaa Xaa Xaa Xaa Xaa Xaa Xaa Xaa Xaa Xaa
    50                  55                  60
Xaa Xaa Xaa Xaa Xaa Xaa Xaa
65                  70
```

(2) INFORMATION FOR SEQ ID NO:80:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 14
        (D) OTHER INFORMATION: /product= "OTHER"
            /note= "G AT POSITION 14 CAN BE ABSENT"

(xi) SEQUENCE DESCRIPTION: SEQ ID NO:80:

```
Gly Lys Phe Thr Ile Val Phe Asp Asp Asp Asp Asp Asp Gly
1               5                   10
```

(2) INFORMATION FOR SEQ ID NO:81:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:81:

```
Lys Phe Thr Ile Val Phe Gly Gly Gly Leu Phe Glu Ala Ile Ala Glu
1               5                   10                  15
Phe Ile Glu Gly Gly Trp Glu Gly Leu Ile Glu Gly
                20                  25
```

(2) INFORMATION FOR SEQ ID NO:82:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:82:

```
Gly Leu Phe Glu Ala Ile Ala Glu Phe Ile Glu Gly Gly Trp Glu Gly
1               5                   10                  15
Leu Ile Glu Gly Cys Lys Phe Thr Ile Val Phe
                20                  25
```

(2) INFORMATION FOR SEQ ID NO:83:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:83:

```
Cys Gly Tyr Gly Gly Gly Gly Gly Pro Lys Lys Lys Arg Lys Val
1               5                   10                  15

Gly Gly Gly Leu Phe Glu Ala Ile Ala Glu Phe Ile Glu Gly Gly Trp
            20                  25                  30

Glu Gly Leu Ile Glu Gly
        35
```

(2) INFORMATION FOR SEQ ID NO:84:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:84:

```
Gly Leu Phe Glu Ala Ile Ala Glu Phe Ile Glu Gly Gly Trp Glu Gly
1               5                   10                  15

Leu Ile Glu Gly Gly Gly Tyr Gly Gly Gly Gly Gly Pro Lys Lys
            20                  25                  30

Lys Arg Lys Val Gly Gly
        35
```

(2) INFORMATION FOR SEQ ID NO:85:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:85:

```
Lys Phe Thr Thr Ile Val Phe Cys Gly Tyr Gly Pro Lys Lys Lys Arg
1               5                   10                  15

Lys Val Gly Gly
        20
```

(2) INFORMATION FOR SEQ ID NO:86:

(i) SEQUENCE CHARACTERISTICS:
        (A) LENGTH: 19 amino acids (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:86:

Cys Gly Tyr Gly Pro Lys Lys Lys Arg Lys Val Gly Gly Lys Phe Thr
1               5                   10                  15

Ile Val Phe (2) INFORMATION FOR SEQ ID NO:87:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 30
        (D) OTHER INFORMATION: /product= "OTHER"
            /note= "G AT POSITION 30 CAN BE ABSENT"

(xi) SEQUENCE DESCRIPTION: SEQ ID NO:87:

Lys Lys Lys Lys Lys Lys Lys Lys Lys Lys Lys Lys Lys Lys Lys
1               5                   10                  15

Gly Lys Phe Thr Ile Val Phe Asp Asp Asp Asp Asp Gly
            20                  25                  30

(2) INFORMATION FOR SEQ ID NO:88:

(i) SEQUENCE CHARACTERISTICS:
        (A) LENGTH: 44 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:88:

Lys Lys Lys Lys Lys Lys Lys Lys Lys Lys Lys Lys Lys Lys Lys
1               5                   10                  15

Lys Phe Thr Ile Val Phe Gly Gly Gly Leu Phe Glu Ala Ile Ala Glu
            20                  25                  30

Phe Ile Glu Gly Gly Trp Glu Gly Leu Ile Glu Gly
        35                  40

(2) INFORMATION FOR SEQ ID NO:89:

(i) SEQUENCE CHARACTERISTICS:
        (A) LENGTH: 43 amino acids
        (B) TYPE: amino acid
        (C) STRANDEDNESS: Not Relevant (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:89:

Lys Lys Lys Lys Lys Lys Lys Lys Lys Lys Lys Lys Lys Lys Lys Lys
1               5                   10                  15

Gly Leu Phe Glu Ala Ile Ala Glu Phe Ile Glu Gly Gly Trp Glu Gly
            20                  25                  30

Leu Ile Glu Gly Cys Lys Phe Thr Ile Val Phe
        35                  40

(2) INFORMATION FOR SEQ ID NO:90:

(i) SEQUENCE CHARACTERISTICS:
        (A) LENGTH: 54 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:90:

Lys Lys Lys Lys Lys Lys Lys Lys Lys Lys Lys Lys Lys Lys Lys Lys
1               5                   10                  15

Gly Leu Phe Glu Ala Ile Ala Glu Phe Ile Glu Gly Gly Trp Glu Gly
            20                  25                  30

Leu Ile Glu Gly Gly Gly Tyr Gly Gly Gly Gly Gly Pro Lys Lys
        35                  40                  45

Lys Arg Lys Val Gly Gly
    50

(2) INFORMATION FOR SEQ ID NO:91:

(i) SEQUENCE CHARACTERISTICS:
        (A) LENGTH: 36 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:91:

Lys Lys Lys Lys Lys Lys Lys Lys Lys Lys Lys Lys Lys Lys Lys Lys
1               5                   10                  15

Lys Phe Thr Thr Ile Val Phe Cys Gly Tyr Gly Pro Lys Lys Lys Arg
            20                  25                  30

Lys Val Gly Gly
        35

(2) INFORMATION FOR SEQ ID NO:92:

(i) SEQUENCE CHARACTERISTICS:
        (A) LENGTH: 37 amino acids

```
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:92:

Lys Lys Lys Lys Lys Lys Lys Lys Lys Lys Lys Lys Lys Lys Lys
1               5                  10                  15

Gly Gly Cys Gly Tyr Gly Pro Lys Lys Lys Arg Lys Val Gly Gly Lys
            20                  25                  30

Phe Thr Ile Val Phe
        35

(2) INFORMATION FOR SEQ ID NO:93:

(i) SEQUENCE CHARACTERISTICS:
            (A) LENGTH: 56 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:93:

Lys Lys Lys Lys Lys Lys Lys Lys Lys Lys Lys Lys Lys Lys Lys
1               5                  10                  15

Gly Gly Cys Gly Tyr Gly Gly Gly Gly Gly Pro Lys Lys Lys Arg
            20                  25                  30

Lys Val Gly Gly Gly Leu Phe Glu Ala Ile Ala Glu Phe Ile Glu Gly
        35                  40                  45

Gly Trp Glu Gly Leu Ile Glu Gly
    50                  55

(2) INFORMATION FOR SEQ ID NO:94:

(i) SEQUENCE CHARACTERISTICS:
            (A) LENGTH: 24 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:94:

Ser Ser Asp Asp Glu Ala Thr Ala Asp Ser Gln His Ser Thr Pro Pro
1               5                  10                  15

Lys Lys Lys Arg Lys Val Gly Gly
            20

(2) INFORMATION FOR SEQ ID NO:95:

(i) SEQUENCE CHARACTERISTICS:
            (A) LENGTH: 40 amino acids
            (B) TYPE: amino acid
```

(C) STRANDEDNESS: Not Relevant
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:95:

```
Lys Lys Lys Lys Lys Lys Lys Lys Lys Lys Lys Lys Lys Lys Lys
1               5                  10                  15

Ser Ser Asp Asp Glu Ala Thr Ala Asp Ser Gln His Ser Thr Pro Pro
                20                  25                  30

Lys Lys Lys Arg Lys Val Gly Gly
        35                  40
```

(2) INFORMATION FOR SEQ ID NO:96:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:96:

```
Met Ser Tyr Tyr His His His His His His Asp Tyr Asp Ile Pro Thr
1               5                  10                  15

Thr Glu Asn Leu Tyr Phe Gln Gly Ser
                20                  25
```

(2) INFORMATION FOR SEQ ID NO:97:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:97:

```
Met Ser Tyr Tyr His His His His His His Asp Tyr Asp Ile Pro Thr
1               5                  10                  15

Thr Glu Asn Leu Tyr Phe Gln Gly Ser Gly Tyr Gly Pro Lys Lys Lys
                20                  25                  30

Arg Lys Val Gly Gly
        35
```

(2) INFORMATION FOR SEQ ID NO:98:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:98:

```
Met Ser Tyr Tyr His His His His His His Asp Tyr Asp Ile Pro Thr
1               5                   10                  15

Thr Glu Asn Leu Tyr Phe Gln Ser Lys Phe Thr Ile Val Phe
            20                  25                  30
```

(2) INFORMATION FOR SEQ ID NO:99:

(i) SEQUENCE CHARACTERISTICS:
        (A) LENGTH: 44 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:99:

```
Met Ser Tyr Tyr His His His His His His Asp Tyr Asp Ile Pro Thr
1               5                   10                  15

Thr Glu Asn Leu Tyr Phe Gln Ser Gly Leu Phe Glu Ala Ile Ala Glu
            20                  25                  30

Phe Ile Glu Gly Gly Trp Glu Gly Leu Ile Glu Gly
            35                  40
```

(2) INFORMATION FOR SEQ ID NO:100:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:100:

```
Met Ser Tyr Tyr His His His His His His Asp Tyr Asp Ile Pro Thr
1               5                   10                  15

Thr Glu Asn Leu Tyr Phe Gln Ser Arg Gly Asp Ser Pro Cys
            20                  25                  30
```

(2) INFORMATION FOR SEQ ID NO:101:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:101:

```
Met Ser Tyr Tyr His His His His His
1               5                   10
```

(2) INFORMATION FOR SEQ ID NO:102:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:102:

```
Met Ser Tyr Tyr His His His His His His Gly Tyr Gly Pro Lys Lys
1               5                   10                  15

Lys Arg Lys Val Gly Gly
            20
```

(2) INFORMATION FOR SEQ ID NO:103:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:103:

```
Met Ser Tyr Tyr His His His His His His Lys Phe Thr Ile Val Phe
1               5                   10                  15
```

(2) INFORMATION FOR SEQ ID NO:104:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:104:

```
Met Ser Tyr Tyr His His His His His His Gly Leu Phe Glu Ala Ile
1               5                   10                  15

Ala Glu Phe Ile Glu Gly Gly Trp Glu Gly Leu Ile Glu Gly
            20                  25                  30
```

(2) INFORMATION FOR SEQ ID NO:105:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide -continued

```
    (iii) HYPOTHETICAL: NO (iv) ANTI-SENSE: NO (xi) SEQUENCE DESCRIPTION: SEQ ID NO:105:

Met Ser Tyr Tyr His His His His His His Arg Gly Asp Ser Pro Cys
1               5                   10                  15

(2) INFORMATION FOR SEQ ID NO:106:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:106:

His His His His His His
1               5

(2) INFORMATION FOR SEQ ID NO:107:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:107:

Gly Gly Gly Gly Gly Tyr Gly Pro Lys Lys Lys Arg Lys Val Gly Gly
1               5                   10                  15

(2) INFORMATION FOR SEQ ID NO:108:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:108:

Gly Gly Tyr Gly Pro Lys Lys Lys Arg Lys Val Gly
1               5                   10

(2) INFORMATION FOR SEQ ID NO:109:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear
```

(ii) MOLECULE TYPE: peptide (iii) HYPOTHETICAL: NO (iv) ANTI-SENSE: NO (xi) SEQUENCE DESCRIPTION: SEQ ID NO:109:

Gly Cys Gly Tyr Gly Pro Lys Lys Lys Arg Lys Val Gly Gly
1               5                   10

(2) INFORMATION FOR SEQ ID NO:110:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:110:

Gly Gly Arg Gly Asp Met Phe Gly Gly
1               5

(2) INFORMATION FOR SEQ ID NO:111:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:111:

Gly Tyr Gly Pro Lys Lys Lys Arg Lys Val Gly Gly Gly Gly Gly Arg
1               5                   10                  15

Gly Asp Met Phe Gly Gly
            20

(2) INFORMATION FOR SEQ ID NO:112:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:112:

Gly Leu Phe Gly Ala Ile Ala Gly Phe Ile Glu Asn Gly Trp Glu Gly
1               5                   10                  15

Met Ile Asp Gly
            20

(2) INFORMATION FOR SEQ ID NO:113:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:113:

Gly Leu Phe Gly Ala Ile Ala Gly Phe Ile Glu Asn Gly Trp Glu Gly
1               5                   10                  15

Leu Ile Glu Gly
            20

(2) INFORMATION FOR SEQ ID NO:114:

(i) SEQUENCE CHARACTERISTICS:
            (A) LENGTH: 20 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:114:

Gly Leu Phe Lys Ala Ile Ala Lys Phe Ile Lys Gly Gly Trp Lys Gly
1               5                   10                  15

Leu Ile Lys Gly
            20

(2) INFORMATION FOR SEQ ID NO:115:

(i) SEQUENCE CHARACTERISTICS:
            (A) LENGTH: 12 amino acids
            (B) TYPE: amino acid
            (C) STRANDEDNESS:
            (D) TOPOLOGY: Not Relevant (ii) MOLECULE TYPE: peptide (iii) HYPOTHETICAL: NO (iv) ANTI-SENSE: NO (xi) SEQUENCE DESCRIPTION: SEQ ID NO:115:

Gly Tyr Gly Pro Lys Lys Lys Arg Lys Val Gly Gly
1               5                   10

(2) INFORMATION FOR SEQ ID NO:116:

(i) SEQUENCE CHARACTERISTICS:
            (A) LENGTH: 31 amino acids
            (B) TYPE: amino acid
            (C) STRANDEDNESS: Not Relevant
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:116:

Lys Lys Lys Lys Lys Lys Lys Lys Lys Lys Lys Lys Lys Lys Lys Lys
1               5                   10                  15
Gly Gly Cys Gly Tyr Gly Pro Lys Lys Lys Arg Lys Val Gly Gly
            20                  25                  30

(2) INFORMATION FOR SEQ ID NO:117:

(i) SEQUENCE CHARACTERISTICS:
        (A) LENGTH: 36 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:117:

Lys Lys Lys Lys Lys Lys Lys Lys Lys Lys Lys Lys Lys Lys Lys Lys
1               5                   10                  15
Cys Gly Tyr Gly Pro Lys Lys Lys Arg Lys Val Gly Gly Gly Gly Arg
            20                  25                  30
Gly Asp Ser Pro
        35

(2) INFORMATION FOR SEQ ID NO:118:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:118:

Lys Lys Lys Lys Lys Lys Lys Lys Lys Lys Lys Lys Lys Lys Lys Lys
1               5                   10                  15
Gly Gly Arg Gly Asp Ser Pro Cys Gly
            20                  25

(2) INFORMATION FOR SEQ ID NO:119:

(i) SEQUENCE CHARACTERISTICS:
        (A) LENGTH: 25 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:119:

Gly Arg Gly Asp Ser Pro Cys Gly Gly Lys Lys Lys Lys Lys Lys Lys
1               5                   10                  15
Lys Lys Lys Lys Lys Lys Lys Lys Lys
            20                  25

-continued (2) INFORMATION FOR SEQ ID NO:120:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:120:

```
Cys Gly Tyr Gly Pro Lys Lys Lys Arg Lys Val Gly Gly Gly Gly Arg
1               5                   10                  15
Gly Asp Ser Pro Cys Gly
            20
```